(12) United States Patent
Torrens-Jover et al.

(10) Patent No.: US 9,611,229 B2
(45) Date of Patent: Apr. 4, 2017

(54) 1,2,3-TRIAZOLE-4-AMINE DERIVATIVES FOR THE TREATMENT OF SIGMA RECEPTOR RELATED DISEASES AND DISORDERS

(71) Applicant: LABORATORIOS DEL DR. ESTEVE S.A., Barcelona (ES)

(72) Inventors: Antoni Torrens-Jover, Terrassa (ES); Ute Christmann, Castelldefels (ES); Josè-Luis Diaz-Fernández, Manresa (ES); Carmen Almansa-Rosales, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/759,280

(22) PCT Filed: Jan. 7, 2014

(86) PCT No.: PCT/EP2014/000012
§ 371 (c)(1),
(2) Date: Jul. 6, 2015

(87) PCT Pub. No.: WO2014/106622
PCT Pub. Date: Jul. 10, 2014

(65) Prior Publication Data
US 2015/0353510 A1    Dec. 10, 2015

(30) Foreign Application Priority Data

Jan. 7, 2013  (EP) .................................... 13382002

(51) Int. Cl.
*C07D 249/04* (2006.01)
*C07D 249/06* (2006.01)
*C07D 295/185* (2006.01)
*C07F 7/10* (2006.01)
*C07D 401/12* (2006.01)

(52) U.S. Cl.
CPC ......... *C07D 249/04* (2013.01); *C07D 249/06* (2013.01); *C07D 295/185* (2013.01); *C07D 401/12* (2013.01); *C07F 7/10* (2013.01)

(58) Field of Classification Search
CPC .................................................. C07D 249/04
See application file for complete search history.

(56) References Cited

U.S. PATENT DOCUMENTS 8,193,223 B2   6/2012  Jagerovc
8,410,159 B2   4/2013  Cuberes-Altisent

FOREIGN PATENT DOCUMENTS

EP   1829867   9/2007
EP   1921071   5/2008

OTHER PUBLICATIONS

Cobos, 2008, Currenty Neuropharmacology, vol. 6, p. 344-366.*
International Search Report for PCT/EP2014/000012 of Feb. 12, 2014.

* cited by examiner

*Primary Examiner* — Rebecca Anderson
*Assistant Examiner* — Karen Cheng
(74) *Attorney, Agent, or Firm* — Hueschen and Sage

(57) ABSTRACT

The present invention relates to new 1,2,3-triazole-amine derivatives, having affinity for sigma receptors, especially sigma-1 receptor, as well as to the process for the preparation thereof, to compositions comprising them, and to their use as medicaments for the treatment of sigma receptor related diseases and disorders.

14 Claims, No Drawings

1,2,3-TRIAZOLE-4-AMINE DERIVATIVES FOR THE TREATMENT OF SIGMA RECEPTOR RELATED DISEASES AND DISORDERS

BACKGROUND AND PRIOR ART

The search for new therapeutic agents has been greatly aided in recent years by better understanding of the structure of proteins and other biomolecules associated with target diseases. One important class of these proteins are the sigma (σ) receptors, cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as SKF 10047, (+)-cyclazocine, and (+)-pentazocine and also for some narcoleptics such as haloperidol.

The term "sigma receptor(s)" as used in this application refers to proteinaceous molecules, containing (a) binding site(s), which molecules functionally differ from opioid, NMDA, dopaminergic, and other known neurotransmitter or hormone receptor families (G. Ronsisvalle et al. Pure Appl. Chem. 73, 1499-1509 (2001)). The sigma receptor has at least two subtypes, which may be discriminated by stereoselective isomers of pharmacoactive drugs. SKF 10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (e.g. central nervous system, ovary, testicle, placenta, adrenal gland, spleen, liver, kidney, gastrointestinal tract) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. The sigma-1 receptor is of great interest in pharmacology in view of its possible physiological role in processes related to analgesia, anxiety, addiction, amnesia, depression, schizophrenia, stress, neuroprotection, psychosis and mood disorders (Kaiser et al (1991) Neurotransmissions 7 (1): 1-5; Walker, J. M. et al, Pharmacological Reviews, 1990, 42, 355; Bowen W. D. (2000) Pharmaceutica Acta Helvetiae 74: 211-218; and Hayashi, T. et al, Drugs of the Future 2009, 34 (2), 137).

The Sigma-2 receptor is also expressed in numerous adult mammal tissues (e.g. nervous system, immune system, endocrine system, liver, kidney). Sigma-2 receptors can be components in a new apoptosis signaling pathway that may play an important role in regulating cell proliferation or in cell development. This pathway seems to consist of Sigma-2 receptors joined to intracellular membranes, located in organelles storing calcium, such as the endoplasmic reticulum and mitochondria, which also have the ability to release calcium from these organelles. The calcium signals can be used in the signaling pathway for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplastic agents for the treatment of cancer. In fact, Sigma-2 receptor agonists have been observed to induce apoptosis in mammary tumor cell lines resistant to common antineoplastic agents that induce DNA damage. In addition, agonists of Sigma-2 receptors enhance the cytotoxic effects of these antineoplastic agents at concentrations at which the agonist is not cytotoxic. Thus, agonists of Sigma-2 receptors can be used as antineoplastic agents at doses inducing apoptosis or at sub-toxic doses in combination with other antineoplasic agents to revert the resistance to the drug, thereby allowing the use of lower doses of the antineoplastic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Different sigma receptor ligands have been reported.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO2008055932 deals with 1,2,4-triazole compounds having good activity towards sigma receptors.

WO2008/055933 deals with 1,2,3-triazole compounds having good activity towards sigma receptors.

WO2009071657 also reports tricyclic triazolic compounds having good activity towards sigma receptors.

Although, some triazole derivatives with therapeutic activity have been disclosed in the prior art, none of these references disclose the 1,2,3-triazole-4-amine derivatives of the present invention. In addition none of these references suggest that 1,2,3-triazole-4-amine derivatives can be active towards sigma receptors.

There is still a need to find compounds having pharmacological activity towards the sigma receptor, being both effective and selective, and having good "drugability" properties, i.e. good pharmaceutical properties related to administration, distribution, metabolism and excretion.

Surprisingly, the authors of the present invention have observed that 1,2,3-triazole-4-amine derivative compounds with general formula (I) show very good affinity for Sigma receptors. These compounds are therefore particularly suitable as pharmacologically active agents in medicaments for the prophylaxis and/or treatment of disorders or diseases related to Sigma receptors.

The present invention relates to new 1,2,3-triazole-amine derivatives, having affinity for sigma receptors, especially sigma-1 receptor, as well as to the process for the preparation thereof, to compositions comprising them, and to their use as medicaments for the treatment of sigma receptor related diseases and disorders.

One aspect of the present invention relates to 1,2,3-triazole-4-amine derivatives of general formula (I):

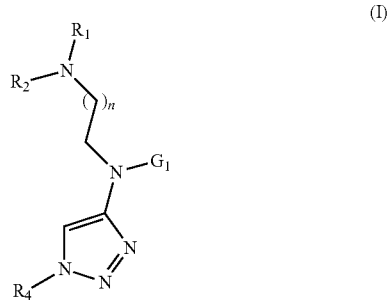

wherein:
$G_1$ is selected from the group consisting of a hydrogen atom; a linear or branched, saturated or unsaturated, substituted or unsubstituted aliphatic radical; a substituted or unsubstituted aryl group which is optionally condensed to other, substituted or unsubstituted, mono- or polycyclic ring systems; a —(C=O)—$R_5$ group; a —(SO)$_2$—$R_6$ group; a —C=Z—NH—$R_8$ group;
$R_1$ and $R_2$, identical or different, are selected from the group consisting of a hydrogen atom; a linear or branched, saturated or unsaturated, substituted or unsubstituted aliphatic radical;
or
$R_1$ and $R_2$ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;
$R_4$ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system;
$R_5$ is selected from the group consisting of a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;
$R_6$ is selected from the group consisting of a linear or branched, saturated or unsaturated, substituted or unsubstituted aliphatic radical; a substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system;
Z is selected from S or O;
$R_8$ is a linear or branched, saturated or unsaturated, substituted or unsubstituted aliphatic radical;
n is 1, 2, 3, or 4;
optionally as of one of the stereoisomers, preferably enantiomers or diastereomers, a racemate or as a mixture of at least two of the stereoisomers, preferably enantiomers and/or diastereomers, in any mixing ratio, or a corresponding salt thereof, or a corresponding solvate thereof.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor and Francis (April 2002).

In the context of this invention, alkyl radical or group is understood as meaning saturated and unsaturated, linear or branched hydrocarbons, which can be unsubstituted or mono- or polysubstituted. Thus unsaturated alkyl is understood to encompass alkenyl and alkynyl groups, like e.g. —CH=CH—CH$_3$ or —C≡C—CH$_3$, while saturated alkyl encompasses e.g. —CH$_3$ and —CH$_2$—CH$_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-C2-, C3-, C4-, or C5-alkyl, $C_{1-6}$-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In the context of this invention aliphatic group or radical includes alkyl (saturated), alkenyl (unsaturated alkyl) and alkynyl (unsaturated alkyl) and thus is synonymous for: saturated or unsaturated alkyl (see above).

In the context of the invention an alkoxy group is an alkyl (carbon and hydrogen chain) group singular bonded to oxygen (R—O). Preferred alkoxy groups are methoxy ($CH_3O$—), ethoxy ($C_2H_5O$—), propoxy ($C_3H_7O$—), or butoxy ($C_4H_9O$—).

In the context of this invention cycloalkyl radical or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. However, mono- or polyunsaturated, preferably monounsaturated, cycloalkyls also in particular fall under the term cycloalkyl as long as the cycloalkyl is not an aromatic system. The alkyl and cycloalkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl. Particularly preferred alkyls are methyl, ethyl, propyl, butyl, and tert-butyl.

Particularly preferred cycloalkyls are cyclopropane, cyclohexyl, and adamantyl.

In the context of this invention alkyl-cycloalkyl is understood as meaning a cycloalkyl group (see above) being connected to another atom through an alkyl group (see above), whereas the alkyl is always saturated and linear or branched always refers to the alkyl.

In connection with alkyl or aliphatic group—unless defined otherwise—the term substituted in the context of this invention is understood as meaning replacement of at least one hydrogen radical by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl; "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH=CH—$CHCl_2$.

Preferred substituents are halogen, substituted or unsubstituted $C_{1-6}$-alkyl, a saturated or unsaturated, linear or branched, substituted or unsubstituted —O—$C_{1-6}$-alkyl (alkoxy).

Very preferred substituents are fluoro, chloro, methyl, ethanone.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{1-4}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-6}$ is to be understood as meaning —$CH_2$—$CH_2$—$CH_2$—$CH_2$— and —$CH_2$—$CH_2$—$CH_2$—$CH_2$—$CH_2$—, etc.

An aryl radical or group is understood as meaning ring systems with at least one aromatic ring but without heteroatoms even in only one of the rings. Examples are phenyl, naphthyl, fluoranthenyl, fluorenyl, tetralinyl or indanyl, radicals, which can be unsubstituted or monosubstituted or polysubstituted.

Particularly preferred aryls are phenyl and naphthyl.

In the context of this invention alkyl-aryl is understood as meaning an aryl group (see above) being connected to another atom through an alkyl-group (see above), whereas the alkyl is always saturated and linear or branched always refers to the alkyl. A preferred alkyl-aryl group is benzyl.

A heterocyclyl radical or group is understood as meaning heterocyclic ring systems, saturated or unsaturated ring which contains one or more heteroatoms from the group consisting of nitrogen, oxygen and/or sulfur in the ring and can also be mono- or polysubstituted. Examples which may be mentioned from the group of heteroaryls are furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole, quinazoline, further heterocycles according to the invention are pyran, pyrrolidine, piperazine, piperidine, imidazole, thiazole, morpholine, azepane; and oxazepane.

Particularly preferred heterocyclyl radicals are pyrrolidine, piperazine, piperidine, morpholine, azepane; and oxazepane.

In the context of this invention alkyl-heterocylyl is understood as meaning a heterocyclyl group (see above) being connected to another atom through an alkyl group (see above), whereas the alkyl is always saturated and linear or branched always refers to the alkyl.

In connection with aryl or alkyl-aryl, cycloalkyl or alkyl-cycloalkyl, heterocyclyl or alkyl-heterocyclyl, substituted is understood—unless defined otherwise—as meaning substitution of the ring-system of the aryl or alkyl-aryl, cycloalkyl or alkyl-cycloalkyl; heterocyclyl or alkyl-heterocyclyl by OH, SH, =O, halogen (F, Cl, Br, I), CN, $NO_2$, COOH;

$NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl.

Preferred substituents are halogen, substituted or unsubstituted $C_{1-6}$-alkyl, a saturated or unsaturated, linear or branched, substituted or unsubstituted —O—$C_{1-6}$-alkyl (alkoxy).

Very preferred substituents are fluoro, chloro, methyl, ethanone.

The term "ring system" according to the present invention refers to ring systems comprising saturated or unsaturated or aromatic carbocyclic ring systems which contain optionally at least one heteroatom selected from N, O or S as ring member and which are substituted or unsubstituted. Said ring systems may be condensed to other carbocyclic ring systems such as aryl groups, heterocyclyl groups, cycloalkyl groups, etc.

The term "condensed" according to the present invention means that a ring or ring-system is attached to another ring or ring-system, whereby the terms "annulated" or "annelated" are also used by those skilled in the art to designate this kind of attachment.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention it is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of:

hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor and Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50 percent, more preferably above 70 percent, most preferably above 90 percent. In a preferred embodiment it is above 95 percent of the compound of formula (I) or, or of its salts, solvates or prodrugs.

The term "pharmacological tool" refers to the property of compounds of the invention through which they are particularly selective ligands for Sigma receptors which implies that compound of formula (I), described in this invention, can be used as a model for testing other compounds as sigma ligands, ex. a radiactive ligands being replaced, and can also be used for modeling physiological actions related to sigma receptors.

A preferred embodiment of the invention relates to 1,2, 3-triazole-4-amine derivatives of general formula (I), wherein $G_1$ is selected from the group consisting of a hydrogen atom; a linear or branched, saturated or unsaturated, substituted or unsubstituted $C_{1-4}$ alkyl radical; an substituted or unsubstituted, at least six membered aryl group; a —(C═O)—$R_5$ group; a —(SO)$_2$—$R_6$ group; a —C═Z—NH—$R_8$ group;

and wherein $R_5$, $R_6$, Z and $R_8$ are as defined herein.

Another preferred embodiment of the invention relates to 1,2,3-triazole-4-amine derivatives of general formula (I), wherein $R_5$ is selected from the group consisting of a linear or branched, saturated or unsaturated, substituted or unsubstituted $C_{1-4}$ alkyl radical; an substituted or unsubstituted, $C_3$-$C_6$ cycloalkyl group; an substituted or unsubstituted, at least six-membered aryl group;

$R_6$ is selected from the group consisting of a linear or branched, saturated or unsaturated, substituted or unsubstituted $C_{1-4}$ alkyl radical; an substituted or unsubstituted, at least six-membered aryl group;

Z is selected from S or O;

wherein $R_8$ is a linear or branched, saturated or unsaturated, substituted or unsubstituted $C_{1-4}$ alkyl radical.

An even more preferred embodiment of the invention relates to 1,2,3-triazole-4-amine derivatives of general formula (I), wherein $G_1$ is selected from the group consisting of a hydrogen atom; a substituted or unsubstituted ethyl group; a substituted or unsubstituted propyl group; a substituted or unsubstituted benzyl group; a —(C=O)—$R_5$ group; a —(SO)$_2$—$R_6$ group; a —C=Z—NH—$R_8$ group; and $R_5$ is selected from the group consisting of a substituted or unsubstituted methyl group; a substituted or unsubstituted tert-butyl group; a substituted or unsubstituted cyclopropane group; a substituted or unsubstituted cyclohexyl group; a substituted or unsubstituted phenyl group; wherein the substituents are selected from halogen;

$R_6$ is selected from the group consisting of a substituted or unsubstituted methyl group; a substituted or unsubstituted phenyl group; wherein the substituents are selected from halogen;

Z is selected from S or O;

$R_8$ is a linear or branched, saturated or unsaturated, substituted or unsubstituted $C_{1-4}$ alkyl radical.

Another preferred embodiment of the invention relates to 1,2,3-triazole-4-amine derivatives of general formula (I), wherein $R_1$ and $R_2$, identical or different, are selected from the group consisting of a hydrogen atom; a linear or branched, saturated or unsaturated, substituted or unsubstituted $C_{1-4}$ alkyl radical;

or $R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with an substituted or unsubstituted mono- or polycyclic ring system, wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, $C_3$-$C_6$ cycloalkyl;

preferably $R_1$ and $R_2$, identical or different, are selected from the group consisting of a hydrogen atom; a linear or branched, substituted or unsubstituted ethyl group;

or $R_1$ and $R_2$ form together with the bridging nitrogen atom to which they are attached a substituted or unsubstituted heterocyclyl group, selected from the group consisting of a pyrrolidine group, a piperazine group, a piperidine group, a morpholine group, an azepane group or an oxazepane group, the heterocyclyl group being unsubstituted or substituted, wherein the substituents are selected from the group consisting of a methyl group, an ethanone group, a fluoro group, a chloro group or a cyclohexyl group.

Another preferred embodiment of the invention relates to 1,2,3-triazole-4-amine derivatives of general formula (I), wherein $R_4$ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted at least six membered aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group is at least six membered and may be substituted or unsubstituted and/or condensed with a mono- or polycyclic ring system; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen.

Another preferred embodiment of the invention relates to 1,2,3-triazole-4-amine derivatives of general formula (I), wherein $R_4$ is selected from the group consisting of a substituted or unsubstituted cyclohexyl group; an substituted or unsubstituted adamantyl group; a substituted or unsubstituted phenyl group; a substituted or unsubstituted benzyl group; a substituted or unsubstituted naphtalene group; wherein the substituents are selected from fluoro and chloro.

Another very preferred embodiment of the invention relates to 1,2,3-triazole-4-amine derivatives of general formula (I), wherein n is 1 or 2.

An even more preferred embodiment of the invention relates to 1,2,3-triazole-4-amine derivatives of general formula (I), wherein $G_1$ is selected from the group consisting of a hydrogen atom; a linear or branched, saturated or unsaturated, substituted or unsubstituted $C_{1-4}$ alkyl radical; an substituted or unsubstituted, at least six membered, aryl group; a —(C=O)—$R_5$ group; a —(SO)$_2$—$R_6$ group; a —C=Z—NH—$R_8$ group;

$R_1$ and $R_2$, identical or different, are selected from the group consisting of a hydrogen atom; a linear or branched, saturated or unsaturated, substituted or unsubstituted $C_{1-4}$ alkyl radical;

or $R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with a substituted or unsubstituted mono- or polycyclic ring system; wherein the heteroatom is selected from the group consisting of N, S, O; the heterocyclyl group and/or mono- or polycyclic ring system being unsubstituted or substituted; wherein the substituents are selected from the group consisting of $C_1$-$C_4$ alkyl, $C_1$-$C_4$ alkoxy, halogen, $C_3$-$C_6$ cycloalkyl;

$R_4$ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted at least six membered aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group is at least six membered and may be substituted or unsubstituted and/or condensed with a mono- or polycyclic ring system; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen;

$R_5$ is selected from the group consisting of a linear or branched, saturated or unsaturated, substituted or unsubstituted $C_{1-4}$ alkyl radical; an substituted or unsubstituted, $C_3$-$C_6$ cycloalkyl group; an substituted or unsubstituted, at least six-membered aryl group;

$R_6$ is selected from the group consisting of a linear or branched, saturated or unsaturated, substituted or unsubstituted $C_{1-4}$ alkyl radical; an substituted or unsubstituted, at least six-membered aryl group;

Z is selected from S or O;

wherein $R_8$ is a linear or branched, saturated or unsaturated, substituted or unsubstituted $C_{1-4}$ alkyl radical.

An even more preferred embodiment of the invention relates to 1,2,3-triazole-4-amine derivatives of general formula (I), wherein $G_1$ is selected from the group consisting of a hydrogen atom; an substituted or unsubstituted ethyl group; a substituted or unsubstituted propyl group; a substituted or unsubstituted benzyl group; a —(C=O)—$R_5$ group; a —(SO)$_2$—$R_6$ group; a —C=Z—NH—$R_8$ group; wherein the substituents are selected from chloro;

$R_1$ and $R_2$, are a substituted or unsubstituted ethyl group;

or $R_1$ and $R_2$ form together with the bridging nitrogen atom to which they are attached a heterocyclyl group selected from the group consisting of a pyrrolidine group, a piperazine group, a piperidine group, a morpholine group, an azepane group, an oxazepane group; the heterocyclyl group being unsubstituted or substituted; wherein the substituents are selected from the group consisting of a methyl group, an ethanone group, a fluoro, a chloro or a cyclohexyl group;

$R_4$ is selected from the group consisting of a substituted or unsubstituted cyclohexyl group, an substituted or unsubstituted adamantyl group, a substituted or unsubstituted phenyl group, a substituted or unsubstituted benzyl group, a substituted or unsubstituted naphtalene group; wherein the substituents are selected from fluoro and chloro;

$R_5$ is selected from the group consisting of a methyl group; a tert-butyl group; a cyclopropane group; a cyclohexyl group; a phenyl group;

$R_6$ is selected from the group consisting of a methyl group; a substituted phenyl group; wherein the substituent is chloro, Z is S, $R_8$ is propyl;

n is 1 or 2.

A very much preferred embodiment of the invention relates to 1,2,3-triazole-4-amine derivatives of general formula (I), wherein $G_1$ is selected from the group consisting of a hydrogen atom; an ethyl group; a propyl group; a substituted or unsubstituted benzyl group; a —(C=O)—$R_5$ group; a —(SO)$_2$—$R_6$ group; a —C=Z—NH—$R_8$ group; wherein the substituents are selected from chloro;

$R_1$ and $R_2$, are an ethyl group;

or $R_1$ and $R_2$ form together with the bridging nitrogen atom to which they are attached a heterocyclyl group selected from the group consisting of a pyrrolidin group, a piperazine group, a piperidine group, a morpholine group, an azepane group; an oxazepane group; the heterocyclyl group being unsubstituted or substituted; wherein the substituents are selected from the group consisting of a methyl group, an ethanone group, a fluoro group, a chloro group or a cyclohexyl group;

$R_4$ is selected from the group consisting of a cyclohexyl group, an adamantyl group; a substituted or unsubstituted phenyl group; a substituted or unsubstituted benzyl group; a naphtalene group; wherein the substituents are selected from fluor and chloro;

$R_5$ is selected from the group consisting of a methyl group; a tert-butyl group; a cyclopropane group; a cyclohexyl group; an phenyl group;

$R_6$ is selected from the group consisting of a methyl group; a substituted phenyl group; wherein the substituent is chloro;

Z is S;

$R_8$ is propyl;

n is 1 or 2.

The following items also form part of the present invention:

Item 1) Another aspect of the invention relates to 1,2,3,-triazole-4-amine derivatives of general formula (I), wherein the compound has a structure of general formula (Ia):

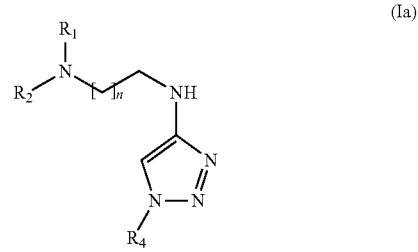

wherein $R_1$ and $R_2$, identical or different, are selected from the group consisting of a hydrogen atom; a linear or branched, saturated or unsaturated, substituted or unsubstituted aliphatic radical;

or $R_1$ and $R_2$ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;

$R_4$ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; an substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system;

n is 1, 2, 3, or 4;

optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 2) A preferred embodiment of the invention relates to 1,2,3,-triazole-4-amine derivatives of general formula (I), wherein the compound has a structure of general formula (Ia):

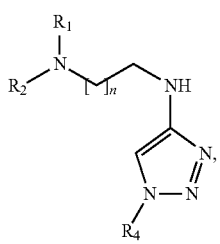

(Ia)

according to item 1),
wherein
$R_1$ and $R_2$, identical or different, are selected from the group consisting of a hydrogen atom; a linear or branched, saturated or unsaturated, substituted or unsubstituted $C_{1-4}$ alkyl radical;
or
$R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with an substituted or unsubstituted mono- or polycyclic ring system; wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, $C_3$-$C_6$ cycloalkyl;
preferably
$R_1$ and $R_2$, identical or different, are selected from the group consisting of a hydrogen atom; a linear or branched, substituted or unsubstituted ethyl group;
or
$R_1$ and $R_2$ form together with the bridging nitrogen atom to which they are attached a substituted or unsubstituted heterocyclyl group, selected from the group consisting of a pyrrolidine group, a piperazine group, a piperidine group, a morpholine group, an azepane group or an oxazepane group; the heterocyclyl group being unsubstituted or substituted, wherein the substituents are selected from the group consisting of a methyl group, an ethanone group, a fluoro group, a chloro group or a cyclohexyl group.

Item 3) Another preferred embodiment of the invention relates to 1,2,3,-triazole-4-amine derivatives of general formula (I), wherein the compound has a structure of general formula (Ia):

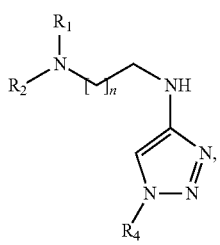

(Ia)

according to any of items 1) or 2),
wherein
$R_4$ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted at least six membered aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group is at least six membered and may be substituted or unsubstituted and/or condensed with a mono- or polycyclic ring system; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen.

Item 4) Another preferred embodiment of the invention relates to 1,2,3,-triazole-4-amine derivatives of general formula (I), wherein the compound has a structure of general formula (Ia):

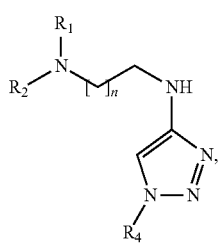

(Ia)

according to any of items 1) through 3),
wherein
$R_4$ is selected from the group consisting of a substituted or unsubstituted cyclohexyl group; an substituted or unsubstituted adamantyl group; a substituted or unsubstituted phenyl group; a substituted or unsubstituted benzyl group; a substituted or unsubstituted naphtalene group; wherein the substituents are selected from fluoro and chloro.

Item 5) Another preferred embodiment of the invention relates to 1,2,3,-triazole-4-amine derivatives of general formula (I), wherein the compound has a structure of general formula (Ia):

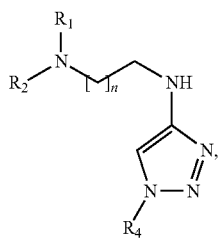

(Ia)

according to any of items 1) through 4),
wherein
n is 1 or 2.

Item 6) Another preferred embodiment of the invention relates to 1,2,3,-triazole-4-amine derivatives of general formula (I), wherein the compound has a structure of general formula (Ia):

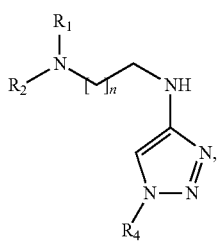

(Ia)

according to any of items 1) through 3) and 5),
wherein
R₁ and R₂, identical or different, are selected from the group consisting of a hydrogen atom; a linear or branched, saturated or unsaturated, substituted or unsubstituted $C_{1-4}$ alkyl radical;
or
R₁ and R₂ form together with the bridging nitrogen atom to which they are attached a mono-cyclic, substituted or unsubstituted, at least one heteroatom containing $C_5$-$C_7$ heterocyclyl group, which is optionally condensed with a substituted or unsubstituted mono- or polycyclic ring system; wherein the heteroatom is selected from the group consisting of N, S, O; the heterocyclyl group and/or mono- or polycyclic ring system being unsubstituted or substituted; wherein the substituents are selected from the group consisting of $C_1$-$C_4$ alkyl, $C_1$-$C_4$ alkoxy, halogen, $C_3$-$C_6$ cycloalkyl;
R₄ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted, at least six membered aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group is at least six membered and may be substituted or unsubstituted and/or condensed with a mono- or polycyclic ring system; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen.

Item 7) Another preferred embodiment of the invention relates to 1,2,3,-triazole-4-amine derivatives of general formula (I), wherein the compound has a structure of general formula (Ia):

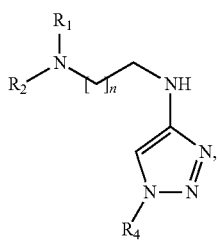

(Ia)

according to any of items 1) through 6),
wherein
R₁ and R₂, are an ethyl group;
or
R₁ and R₂ form together with the bridging nitrogen atom to which they are attached a heterocyclyl group selected from the group consisting of a pyrrolidin group, a piperazine group, a piperidine group, a morpholine group, an azepane group, an oxazepane group; the heterocyclyl group being unsubstituted or substituted; wherein the substituents are selected from the group consisting of a methyl group, an ethanone group, a fluoro, a chloro or a cyclohexyl group;
R₄ is selected from the group consisting of a cyclohexyl group; an adamantyl group; a substituted or unsubstituted phenyl group, a substituted or unsubstituted benzyl group, a naphtalene group; wherein the substituents are selected from fluoro and chloro,
n is 1 or 2.

Item 8) Another aspect of the invention relates to 1,2,3,-triazole-4-amine derivatives of general formula (I), wherein the compound has a structure of general formula (Ib):

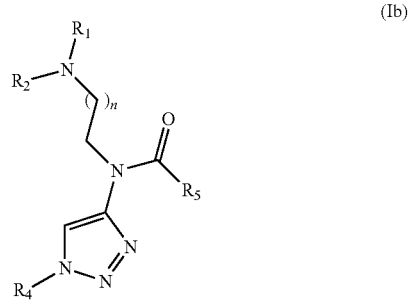

(Ib)

wherein
R₁ and R₂, identical or different, are selected from the group consisting of a hydrogen atom; a linear or branched, saturated or unsaturated, substituted or unsubstituted aliphatic radical;
or
R₁ and R₂ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;
R₄ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; an substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system;
R₅ is selected from the group consisting of a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;

n is 1, 2, 3, or 4;

optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 9) A preferred embodiment of the invention relates to 1,2,3,-triazole-4-amine derivatives of general formula (I), wherein the compound has a structure of general formula (Ib):

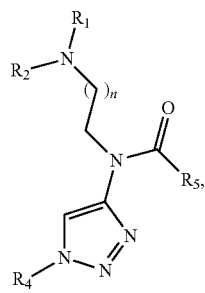

(Ib)

according to item 8),
wherein
$R_1$ and $R_2$ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;
$R_4$ is selected from the group consisting of a a substituted or unsubstituted cycloalkyl group which is optionally condensed to other, substituted or unsubstituted, mono- or polycyclic ring systems; an substituted or unsubstituted aryl group which is optionally condensed to other, substituted or unsubstituted, mono- or polycyclic ring systems; a branched or unbranched, saturated, substituted or unsubstituted alkyl-aryl group in which the aryl group may be substituted or unsubstituted and/or condensed with a mono- or polycyclic ring system;
$R_5$ is selected from the group consisting of a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems;
n is 1, 2, 3, or 4;
optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 10) Another preferred embodiment of the invention relates to 1,2,3,-triazole-4-amine derivatives of general formula (I), wherein the compound has a structure of general formula (Ib):

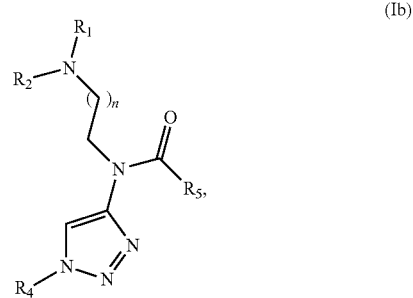

(Ib)

according to items 8) or 9),
wherein
$R_5$ is selected from the group consisting of a linear or branched, saturated or unsaturated, substituted or unsubstituted $C_{1-4}$ alkyl radical; an substituted or unsubstituted, $C_3$-$C_6$ cycloalkyl group; an substituted or unsubstituted, at least six-membered aryl group.

Item 11) Another preferred embodiment of the invention relates to 1,2,3,-triazole-4-amine derivatives of general formula (I), wherein the compound has a structure of general formula (Ib):

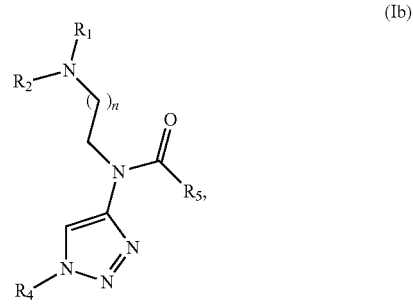

(Ib)

according to any of items 8) through 10),
wherein
$R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with an substituted or unsubstituted mono- or polycyclic ring system; wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, $C_3$-$C_6$ cycloalkyl;
preferably
$R_1$ and $R_2$ form together with the bridging nitrogen atom to which they are attached a substituted or unsubstituted heterocyclyl group, selected from the group consisting of a pyrrolidine group, a piperazine group, a piperidine group, a morpholine group, an azepane group or an oxazepane group; the heterocyclyl group being unsubstituted or substituted, wherein the substituents are selected from the group consisting of a fluoro group, a chloro group.

Item 12) Another preferred embodiment of the invention relates to 1,2,3,-triazole-4-amine derivatives of general formula (I), wherein the compound has a structure of general formula (Ib):

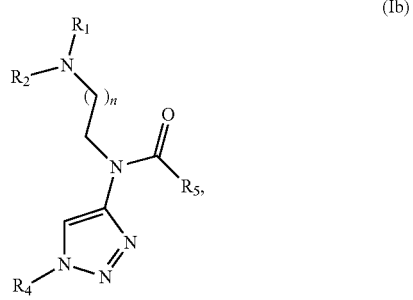

(Ib)

according to any of items 8) through 11),
wherein
$R_4$ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted at least six membered aryl group which is optionally condensed to other, substituted or unsubstituted, mono- or polycyclic ring systems; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen.

Item 13) Another preferred embodiment of the invention relates to 1,2,3,-triazole-4-amine derivatives of general formula (I), wherein the compound has a structure of general formula (Ib):

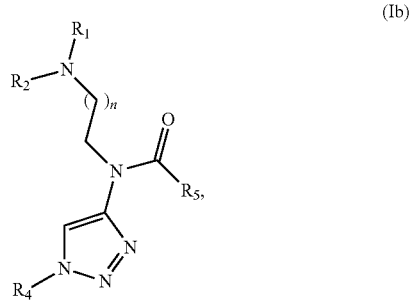

(Ib)

according to any of items 8) through 12),
wherein
$R_4$ is selected from the group consisting of a substituted or unsubstituted adamantyl group; a substituted or unsubstituted phenyl group; a substituted or unsubstituted benzyl group; wherein the substituents are selected from fluoro and chloro.

Item 14) Another preferred embodiment of the invention relates to 1,2,3,-triazole-4-amine derivatives of general formula (I), wherein the compound has a structure of general formula (Ib):

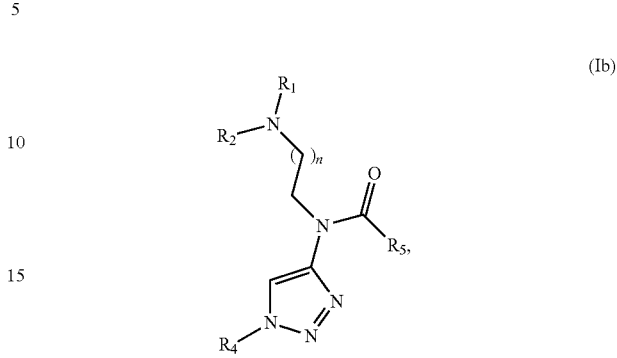

(Ib)

according to any of items 8) through 13),
wherein
n is 1 or 2.

Item 15) Another preferred embodiment of the invention relates to 1,2,3,-triazole-4-amine derivatives of general formula (I), wherein the compound has a structure of general formula (Ib):

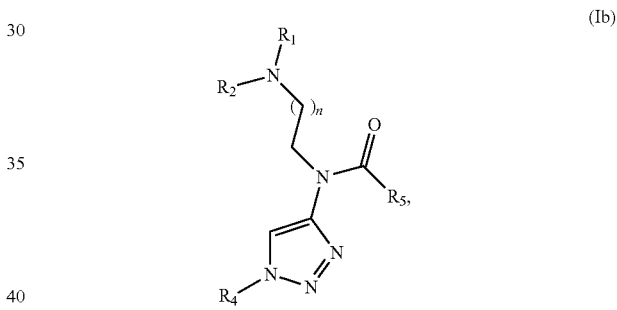

(Ib)

according to any of items 8) through 12) and 14),
wherein
$R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with a substituted or unsubstituted mono- or polycyclic ring system; wherein the heteroatom is selected from the group consisting of N, S, O; the heterocyclyl group and/or mono- or polycyclic ring system being unsubstituted or substituted; wherein the substituents are selected from the group consisting of $C_1$-$C_4$ alkyl, $C_1$-$C_4$ alkoxy, halogen, $C_3$-$C_6$ cycloalkyl;
$R_4$ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted at least six membered aryl group which is optionally condensed to other, substituted or unsubstituted, mono- or polycyclic ring systems; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen;

$R_5$ is selected from the group consisting of a linear or branched, saturated or unsaturated, substituted or unsubstituted $C_{1-4}$ alkyl radical; an substituted or unsubstituted, $C_3$-$C_6$ cycloalkyl group; an substituted or unsubstituted, at least six-membered aryl group.

Item 16) Another preferred embodiment of the invention relates to 1,2,3,-triazole-4-amine derivatives of general formula (I), wherein the compound has a structure of general formula (Ib):

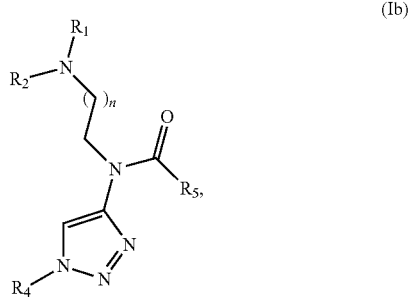

according to any of items 8) through 15),
wherein
$R_1$ and $R_2$ form together with the bridging nitrogen atom to which they are attached a a morpholine group;
$R_4$ is selected from the group consisting of an adamantyl group; a substituted phenyl group, a substituted benzyl group, a naphtalene group; wherein the substituents are selected from chloro;
$R_5$ is selected from the group consisting of a methyl group; a tert-butyl group; a cyclopropane group; a cyclohexyl group; a phenyl group;
n is 1.

Item 17) Another aspect of the invention relates to 1,2,3,-triazole-4-amine derivatives of general formula (I), wherein the compound has a structure of general formula (Ic):

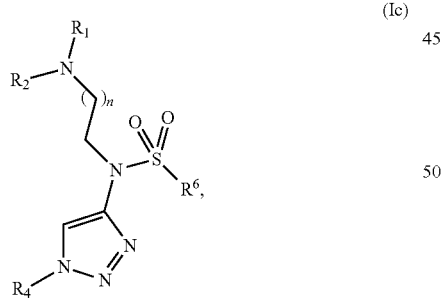

wherein:
$R_1$ and $R_2$, identical or different, are selected from the group consisting of a hydrogen atom; a linear or branched, saturated or unsaturated, substituted or unsubstituted aliphatic radical;
or
$R_1$ and $R_2$ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;

$R_4$ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; an substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system;
$R_6$ is selected from the group consisting of a linear or branched, saturated or unsaturated, substituted or unsubstituted aliphatic radical; a substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system;
n is 1, 2, 3, or 4;
optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 18) Another aspect of the invention relates to 1,2,3,-triazole-4-amine derivatives of general formula (I), wherein the compound has a structure of general formula (Ic):

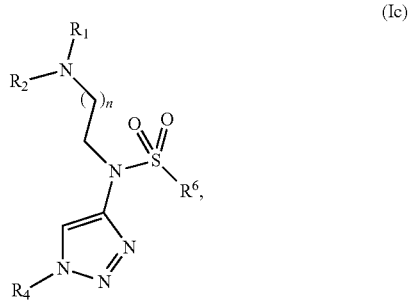

according to item 17),
wherein
$R_1$ and $R_2$ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;
$R_4$ is selected from the group consisting of a substituted or unsubstituted aryl group which is optionally condensed to other, substituted or unsubstituted, mono- or polycyclic ring systems;
$R_6$ is selected from the group consisting of a linear or branched, saturated or unsaturated, substituted or unsubstituted aliphatic radical; a substituted or unsubstituted aryl group which is optionally condensed to other, substituted or unsubstituted, mono- or polycyclic ring systems;
n is 1, 2, 3, or 4;

optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 19) A preferred embodiment of the invention relates to 1,2,3,-triazole-4-amine derivatives of general formula (I), wherein the compound has a structure of general formula (Ic):

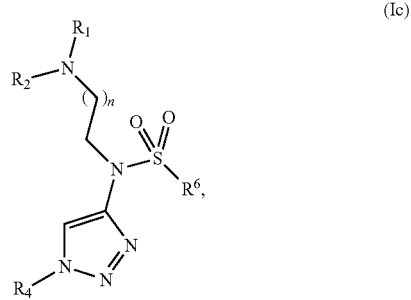

according to items 17) or 18),
wherein
$R_6$ is selected from the group consisting of a linear or branched, saturated or unsaturated, substituted or unsubstituted $C_{1-4}$ alkyl radical; an substituted or unsubstituted, at least six-membered aryl group;
preferably
$R_6$ is selected from the group consisting of a substituted or unsubstituted methyl group; a substituted or unsubstituted phenyl group; wherein the substituents are selected from halogen.

Item 20) Another preferred embodiment of the invention relates to 1,2,3,-triazole-4-amine derivatives of general formula (I), wherein the compound has a structure of general formula (Ic):

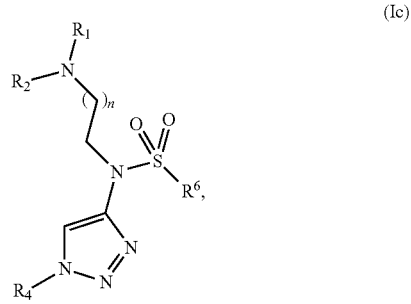

according to any of items 17) through 19),
wherein
$R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with an substituted or unsubstituted mono- or polycyclic ring system; wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, $C_3$-$C_6$ cycloalkyl;

preferably
$R_1$ and $R_2$ form together with the bridging nitrogen atom to which they are attached a substituted or unsubstituted heterocyclyl group, selected from the group consisting of a pyrrolidine group, a piperazine group, a piperidine group, a morpholine group, an azepane group or an oxazepane group; the heterocyclyl group being unsubstituted or substituted, wherein the substituents are selected from the group consisting of a fluoro group or a chloro group.

Item 21) Another preferred embodiment of the invention relates to 1,2,3,-triazole-4-amine derivatives of general formula (I), wherein the compound has a structure of general formula (Ic):

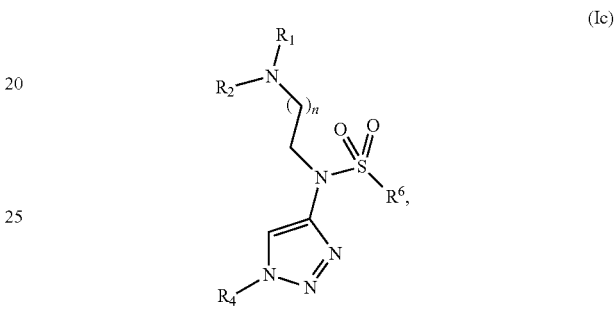

according to any of items 17) through 20),
wherein
$R_4$ is selected from the group consisting of a substituted or unsubstituted aryl group which is optionally condensed to other, substituted or unsubstituted, mono- or polycyclic ring systems; wherein the substituents are selected from halogen.

Item 22) Another preferred embodiment of the invention relates to 1,2,3,-triazole-4-amine derivatives of general formula (I), wherein the compound has a structure of general formula (Ic):

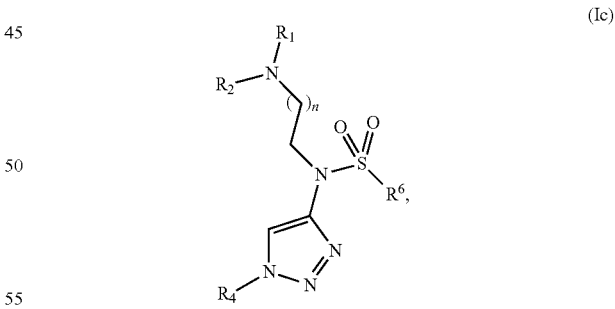

according to any of items 17) through 21),
wherein
$R_4$ is a substituted or unsubstituted phenyl group; wherein the substituents are chloro.

Item 23) Another preferred embodiment of the invention relates to 1,2,3,-triazole-4-amine derivatives of general formula (I), wherein the compound has a structure of general formula (Ic):

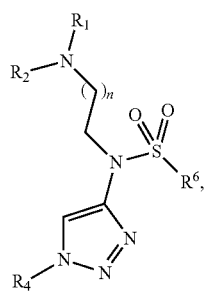

according to any of items 17) through 22),
wherein
n is 1 or 2.

Item 24) Another preferred embodiment of the invention relates to 1,2,3,-triazole-4-amine derivatives of general formula (I), wherein the compound has a structure of general formula (Ic):

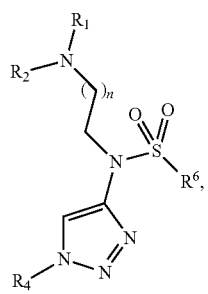

according to any of items 17) through 21) and 23),
wherein $R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with a substituted or unsubstituted mono- or polycyclic ring system; wherein the heteroatom is selected from the group consisting of N, S, O; the heterocyclyl group and/or mono- or polycyclic ring system being unsubstituted or substituted; wherein the substituents are selected from the group consisting of $C_1$-$C_4$ alkyl, $C_1$-$C_4$ alkoxy, halogen, $C_3$-$C_6$ cycloalkyl;

$R_4$ is a substituted or unsubstituted, at least six membered aryl group which is optionally condensed to other, substituted or unsubstituted, mono- or polycyclic ring systems; wherein the substituents are selected from halogen;

$R_6$ is selected from the group consisting of a linear or branched, saturated or unsaturated, substituted or unsubstituted $C_{1-4}$ alkyl radical; an substituted or unsubstituted, at least six-membered aryl group.

Item 25) Another preferred embodiment of the invention relates to 1,2,3,-triazole-4-amine derivatives of general formula (I), wherein the compound has a structure of general formula (Ic):

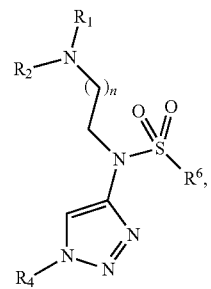

according to any of items 17) through 24),
wherein $R_1$ and $R_2$ form together with the bridging nitrogen atom to which they are attached a morpholine group;

$R_4$ is a substituted phenyl group, wherein the substituents are chloro;

$R_6$ is selected from the group consisting of a methyl group; a substituted phenyl group; wherein the substituents are chloro;

n is 1.

Item 26) Another aspect of the invention relates to 1,2,3,-triazole-4-amine derivatives of general formula (I), wherein the compound has a structure of general formula (Id):

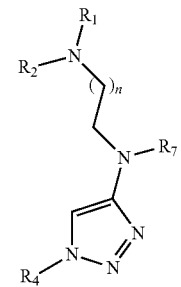

wherein
$R_7$ is selected from the group consisting of a hydrogen atom; a linear or branched, saturated or unsaturated, substituted or unsubstituted aliphatic radical; an substituted or unsubstituted aryl group which is optionally condensed to other, substituted or unsubstituted, mono- or polycyclic ring systems;

$R_1$ and $R_2$, identical or different, are selected from the group consisting of a hydrogen atom; a linear or branched, saturated or unsaturated, substituted or unsubstituted aliphatic radical;
or
$R_1$ and $R_2$ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;

$R_4$ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; an substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system;

n is 1, 2, 3, or 4;

optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 27) A preferred embodiment of the invention relates to 1,2,3,-triazole-4-amine derivatives of general formula (I), wherein the compound has a structure of general formula (Id):

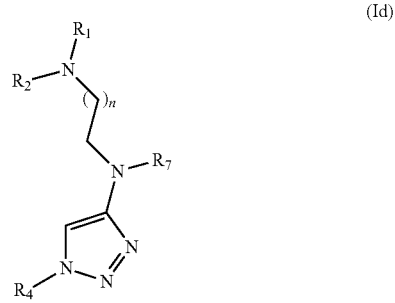

according to item 26), wherein:

$R_7$ is selected from the group consisting of a linear or branched, saturated or unsaturated, substituted or unsubstituted $C_{1-4}$ alkyl radical; an substituted or unsubstituted, at least six membered aryl group;

preferably $R_7$ is selected from the group consisting of a substituted or unsubstituted ethyl group; a substituted or unsubstituted propyl group; a substituted or unsubstituted benzyl group.

Item 28) Another preferred embodiment of the invention relates to 1,2,3,-triazole-4-amine derivatives of general formula (I), wherein the compound has a structure of general formula (Id):

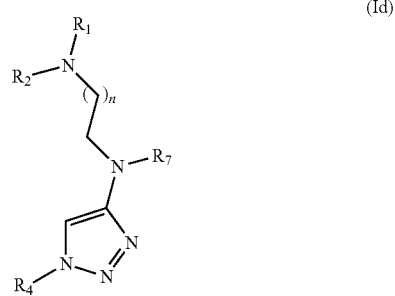

according to items 26) or 27), wherein $R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with an substituted or unsubstituted mono- or polycyclic ring system; wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, $C_3$-$C_6$ cycloalkyl;

preferably $R_1$ and $R_2$ form together with the bridging nitrogen atom to which they are attached a substituted or unsubstituted heterocyclyl group, selected from the group consisting of a pyrrolidine group, a piperazine group, a piperidine group, a morpholine group, an azepane group or an oxazepane group; the heterocyclyl group being unsubstituted or substituted, wherein the substituents are selected from the group consisting of a fluoro group or a chloro group.

Item 29) Another preferred embodiment of the invention relates to 1,2,3,-triazole-4-amine derivatives of general formula (I), wherein the compound has a structure of general formula (Id):

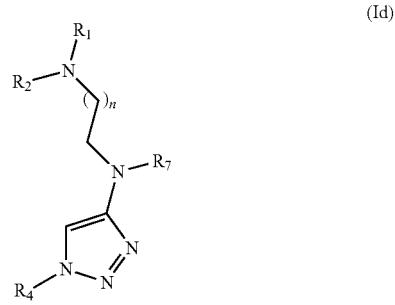

according to any of items 26) through 28), wherein $R_4$ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted at least six membered aryl group which is optionally condensed to other, substituted or unsubstituted, mono- or polycyclic ring systems; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen.

Item 30) Another preferred embodiment of the invention relates to 1,2,3,-triazole-4-amine derivatives of general formula (I), wherein the compound has a structure of general formula (Id):

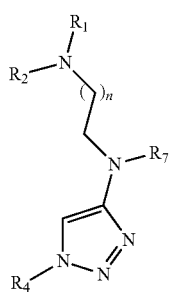

(Id)

according to any of items 26) through 29),
wherein
$R_4$ is selected from the group consisting of a substituted or unsubstituted cyclohexyl group; an substituted or unsubstituted adamantyl group; a substituted or unsubstituted phenyl group; a substituted or unsubstituted benzyl group; a substituted or unsubstituted naphtalene group; wherein the substituents are selected from fluoro and chloro.

Item 31) Another preferred embodiment of the invention relates to 1,2,3,-triazole-4-amine derivatives of general formula (I), wherein the compound has a structure of general formula (Id):

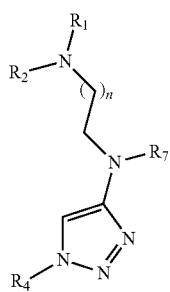

(Id)

according to any of items 26) through 30),
wherein
n is 1 or 2.

Item 32) Another preferred embodiment of the invention relates to 1,2,3,-triazole-4-amine derivatives of general formula (I), wherein the compound has a structure of general formula (Id):

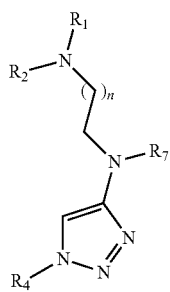

(Id)

according to any of items 26) through 29) and 31),
wherein
$R_7$ is selected from the group consisting of a hydrogen atom; a linear or branched, saturated or unsaturated, substituted or unsubstituted $C_{1-4}$ alkyl radical; an substituted or unsubstituted, at least six membered aryl group;

$R_1$ and $R_2$ form together with the bridging nitrogen atom to which they are attached a mono-cyclic, substituted or unsubstituted, at least one heteroatom containing $C_5$-$C_7$ heterocyclyl group, which is optionally condensed with a substituted or unsubstituted mono- or polycyclic ring system; wherein the heteroatom is selected from the group consisting of N, S, O; the heterocyclyl group and/or mono- or polycyclic ring system being unsubstituted or substituted; wherein the substituents are selected from the group consisting of $C_1$-$C_4$ alkyl, $C_1$-$C_4$ alkoxy, halogen, $C_3$-$C_6$ cycloalkyl;

$R_4$ is selected from the group consisting of an substituted or unsubstituted $C_6$-$C_{10}$ cycloalkyl group, which is optionally condensed to other, substituted or unsubstituted, mono- or polycyclic ring systems; an substituted or unsubstituted at least six membered aryl group which is optionally condensed to other, substituted or unsubstituted, mono- or polycyclic ring systems; a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen.

Item 33) Another preferred embodiment of the invention relates to 1,2,3,-triazole-4-amine derivatives of general formula (I), wherein the compound has a structure of general formula (Id):

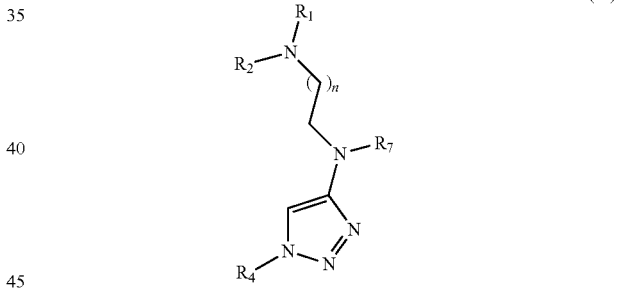

(Id)

according to any of items 26) through 32),
wherein
$R_7$ is selected from the group consisting of an ethyl group; a propyl group; a substituted benzyl group; wherein the substituents are selected from chloro;

$R_1$ and $R_2$ form together with the bridging nitrogen atom to which they are attached a heterocyclyl group selected from the group consisting of a piperidine group, a morpholine group;

$R_4$ is selected from the group consisting of an adamantyl group; a substituted phenyl group, a substituted or unsubstituted benzyl group, wherein the substituents are selected from chloro;

n is 1 or 2.

Item 34) Another aspect of the invention relates to 1,2,3,-triazole-4-amine derivatives of general formula (I), wherein the compound has a structure of general formula (Ie):

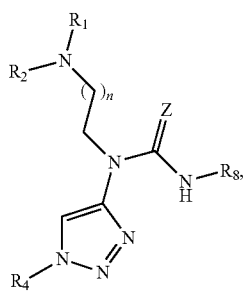

wherein
R₁ and R₂, identical or different, are selected from the group consisting of a hydrogen atom; a linear or branched, saturated or unsaturated, substituted or unsubstituted aliphatic radical;
or
R₁ and R₂ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;

R₄ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; an substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkylaryl group in which the aryl group may be substituted or unsubstituted and/or condensed with a mono- or polycyclic ring system;

Z is selected from S or O;
R₈ is a linear or branched, saturated or unsaturated, substituted or unsubstituted aliphatic radical;
n is 1, 2, 3, or 4;
optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 35) A preferred embodiment of the invention relates to 1,2,3,-triazole-4-amine derivatives of general formula (I), wherein the compound has a structure of general formula (Ie):

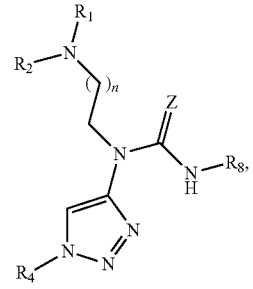

according to item 34),
wherein
R₁ and R₂ form together with the bridging nitrogen atom to which they are attached an at least mono-cyclic, substituted or unsubstituted, at least one heteroatom containing heterocyclyl group which is optionally condensed with a substituted or unsubstituted mono- or polycyclic ring system;
R₄ is selected from the group consisting of a hydrogen atom; a linear or branched, saturated or unsaturated, substituted or unsubstituted aliphatic radical; an substituted or unsubstituted aryl group which is optionally condensed to other, substituted or unsubstituted, mono- or polycyclic ring systems;
Z is selected from S or O;
R₈ is a linear or branched, saturated or unsaturated, substituted or unsubstituted aliphatic radical;
n is 1, 2, 3, or 4;
optionally as one of the stereoisomers, preferably enantiomers or diastereomers, a racemate or as of a mixture of at least two of the stereoisomers, preferably enantiomers and/or diastereomers, in any mixing ratio, or a corresponding salt thereof, or a corresponding solvate thereof.

Item 36) Another preferred embodiment of the invention relates to 1,2,3,-triazole-4-amine derivatives of general formula (I), wherein the compound has a structure of general formula (Ie):

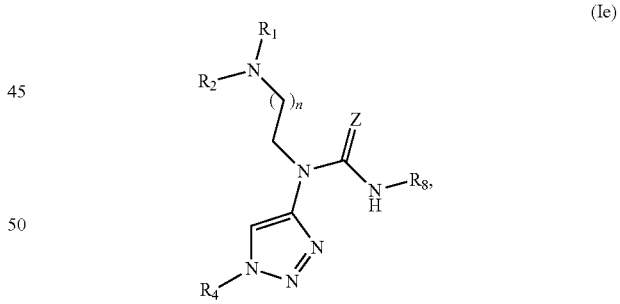

according to items 34) or 35),
wherein
Z is selected from S or O;
R₈ is a linear or branched, saturated or unsaturated, substituted or unsubstituted C₁₋₄ alkyl radical;
more preferably
Z is selected from S or O;
R₈ is a linear or branched, saturated or unsaturated, substituted or unsubstituted C₁₋₄ alkyl radical.

Item 37) Another preferred embodiment of the invention relates to 1,2,3,-triazole-4-amine derivatives of general formula (I), wherein the compound has a structure of general formula (Ie):

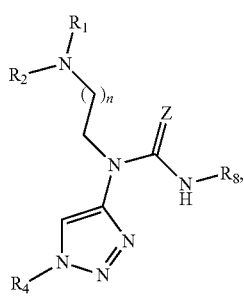

(Ie)

according to any of items 34) through 36),
wherein
R₁ and R₂ form together with the bridging nitrogen atom to which they are attached a mono-cyclic, substituted or unsubstituted, at least one heteroatom containing $C_5$-$C_7$ heterocyclyl group, which is optionally condensed with an substituted or unsubstituted mono- or polycyclic ring system; wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, $C_3$-$C_6$ cycloalkyl;
preferably
R₁ and R₂ form together with the bridging nitrogen atom to which they are attached a substituted or unsubstituted heterocyclyl group, selected from the group consisting of a pyrrolidine group, a piperazine group, a piperidine group, a morpholine group, an azepane group or an oxazepane group; the heterocyclyl group being unsubstituted or substituted, wherein the substituents are selected from the group consisting of a methyl group, an ethanone group, a fluoro group, a chloro group or a cyclohexyl group.

Item 38) Another preferred embodiment of the invention relates to 1,2,3,-triazole-4-amine derivatives of general formula (I), wherein the compound has a structure of general formula (Ie):

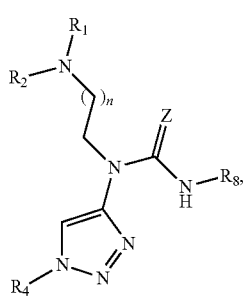

(Ie)

according to any of items 34) through 37),
wherein
R₄ is selected from the group consisting of a linear or branched, saturated or unsaturated, substituted or unsubstituted aliphatic radical; an substituted or unsubstituted aryl group which is optionally condensed to other, substituted or unsubstituted, mono- or polycyclic ring systems.

Item 39) Another preferred embodiment of the invention relates to 1,2,3,-triazole-4-amine derivatives of general formula (I), wherein the compound has a structure of general formula (Ie):

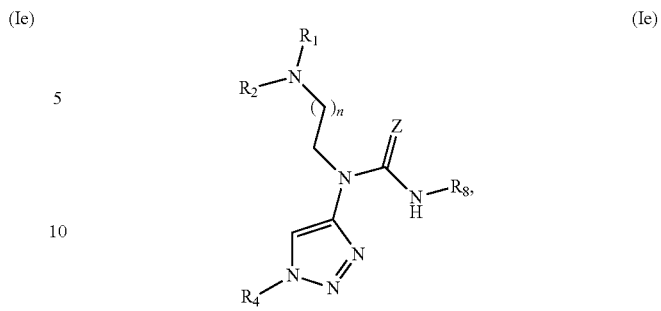

(Ie)

according to any of items 34) through 38),
wherein
R₄ is selected from the group consisting of a substituted or unsubstituted aryl group; wherein the substituents are selected from halogen.

Item 40) Another preferred embodiment of the invention relates to 1,2,3,-triazole-4-amine derivatives of general formula (I), wherein the compound has a structure of general formula (Ie):

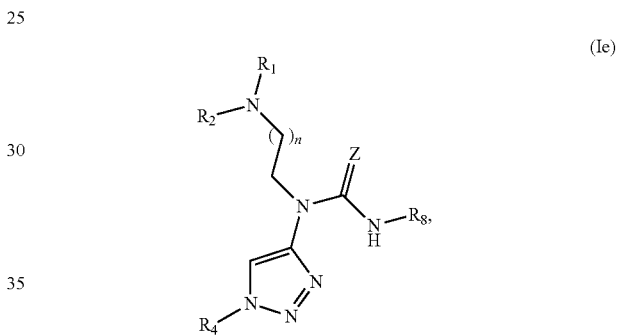

(Ie)

according to any of items 34) through 39),
wherein
n is 1 or 2.

Item 41) Another preferred embodiment of the invention relates to 1,2,3,-triazole-4-amine derivatives of general formula (I), wherein the compound has a structure of general formula (Ie):

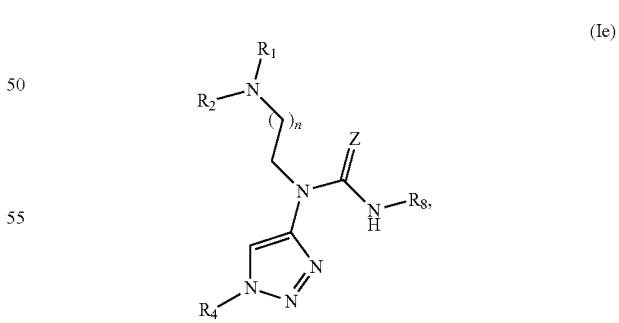

(Ie)

according to any of items 34) through 40),
wherein
R₁ and R₂ form together with the bridging nitrogen atom to which they are attached a mono-cyclic, substituted or unsubstituted, at least one heteroatom containing $C_5$-$C_7$ heterocyclyl group, which is optionally condensed with a substituted or unsubstituted mono- or polycyclic ring system; wherein the heteroatom is selected from the group consisting of N, S, O; the heterocyclyl group and/or mono- or polycyclic ring system being unsubstituted or substituted; wherein the substituents are selected from the group consisting of $C_1$-$C_4$ alkyl, $C_1$-$C_4$ alkoxy, halogen, $C_3$-$C_6$ cycloalkyl;

$R_4$ is selected from the group consisting of an substituted or unsubstituted, at least six membered aryl group which is optionally condensed to other, substituted or unsubstituted, mono- or polycyclic ring systems; wherein the substituents are selected from halogen;

Z is selected from S or O;

$R_8$ is a linear or branched, saturated or unsaturated, substituted or unsubstituted $C_{1-4}$ alkyl radical.

Item 42) Another preferred embodiment of the invention relates to 1,2,3,-triazole-4-amine derivatives of general formula (I), wherein the compound has a structure of general formula (Ie):

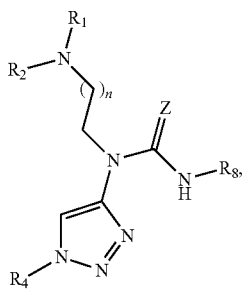

(Ie)

according to any of items 34) through 41),
wherein
$R_1$ and $R_2$ form together with the bridging nitrogen atom to which they are attached a morpholine group;
$R_4$ is a substituted phenyl group; wherein the substituents are chloro;
Z is S,
$R_8$ is propyl;
n is 1.

As can be seen above compounds according to general formulae (Ia), (Ib), (Ic), (Id) and (Ie) are compounds falling into the group of compounds according to general formula (I) as defined herein. Therefore, any teaching and/or mentioning and/or aspect and/or embodiment of the present invention relating to compounds of general formula (I) also equally applies to compounds according to general formulae (Ia), (Ib), (Ic), (Id) and (Ie).

The most preferred embodiment of the invention relates to 1,2,3-triazole-4-amine derivatives of general formula (I), wherein the derivative is selected from the group consisting of

[1] 1-(4-(2-(1-(3,4-dichlorobenzyl)-1H-1,2,3-triazol-4-ylamino)ethyl)piperazin-1-yl)ethanone hydrochloride
[2] 1-(3,4-dichlorophenyl)-N-(2-(piperidin-1-yl)ethyl)-1H-1,2,3-triazol-4-amine hydrochloride
[3] 1-(2,4-dichlorophenyl)-N-(2-(piperidin-1-yl)ethyl)-1H-1,2,3-triazol-4-amine hydrochloride
[4] 1-benzyl-N-(2-(piperidin-1-yl)ethyl)-1H-1,2,3-triazol-4-amine hydrochloride
[5] 1-(3,4-dichlorophenyl)-N-(2-morpholinoethyl)-1H-1,2,3-triazol-4-amine hydrochloride
[6] 1-(1-adamantyl)-N-(2-morpholinoethyl)-1H-1,2,3-triazol-4-amine hydrochloride
[7] 1-(3,4-dichlorobenzyl)-N-(2-morpholinoethyl)-1H-1,2,3-triazol-4-amine hydrochloride
[8] 1-benzyl-N-(2-morpholinoethyl)-1H-1,2,3-triazol-4-amine hydrochloride
[9] 1-(3,4-dichlorobenzyl)-N-(2-(piperidin-1-yl)ethyl)-1H-1,2,3-triazol-4-amine hydrochloride
[10] 1-(3,4-dichlorobenzyl)-N-(3-(piperidin-1-yl)propyl)-1H-1,2,3-triazol-4-amine hydrochloride
[11] 1-(3-fluorophenyl)-N-(2-morpholinoethyl)-1H-1,2,3-triazol-4-amine hydrochloride
[12] N-(2-(azepan-1-yl)ethyl)-1-(3,4-dichlorobenzyl)-1H-1,2,3-triazol-4-amine hydrochloride
[13] N-(2-(azepan-1-yl)ethyl)-1-(3-fluorophenyl)-1H-1,2,3-triazol-4-amine hydrochloride
[14] N-(2-(azepan-1-yl)ethyl)-1-(1-adamantyl)-1H-1,2,3-triazol-4-amine hydrochloride
[15] N-(2-(azepan-1-yl)ethyl)-1-benzyl-1H-1,2,3-triazol-4-amine hydrochloride
[16] 1-benzyl-N-(2-(4-methylpiperazin-1-yl)ethyl)-1H-1,2,3-triazol-4-amine hydrochloride
[17] 1-(4-fluorobenzyl)-N-(2-(piperidin-1-yl)ethyl)-1H-1,2,3-triazol-4-amine hydrochloride
[18] 1-(3-fluorobenzyl)-N-(2-(piperidin-1-yl)ethyl)-1H-1,2,3-triazol-4-amine hydrochloride
[19] 1-benzyl-N-(2-(pyrrolidin-1-yl)ethyl)-1H-1,2,3-triazol-4-amine hydrochloride
[20] 1-(3-fluorophenyl)-N-(2-(pyrrolidin-1-yl)ethyl)-1H-1,2,3-triazol-4-amine hydrochloride
[21] N1-(1-benzyl-1H-1,2,3-triazol-4-yl)-N2,N2-diethylethane-1,2-diamine hydrochloride
[22] N-(2-morpholinoethyl)-1-(naphthalen-1-yl)-1H-1,2,3-triazol-4-amine hydrochloride
[23] 1-(3,4-dichlorophenyl)-N-(3-morpholinopropyl)-1H-1,2,3-triazol-4-amine hydrochloride
[24] 1-cyclohexyl-N-(2-morpholinoethyl)-1H-1,2,3-triazol-4-amine hydrochloride
[25] 1-(4-fluorobenzyl)-N-(2-morpholinoethyl)-1H-1,2,3-triazol-4-amine hydrochloride
[26] 1-(3,4-dichlorobenzyl)-N-(3-morpholinopropyl)-1H-1,2,3-triazol-4-amine
[27] 1-(4-fluorobenzyl)-N-(3-morpholinopropyl)-1H-1,2,3-triazol-4-amine
[28] 1-cyclohexyl-N-(3-morpholinopropyl)-1H-1,2,3-triazol-4-amine
[29] 1-cyclohexyl-N-(2-(piperidin-1-yl)ethyl)-1H-1,2,3-triazol-4-amine hydrochloride
[30] 1-cyclohexyl-N-(2-(4-cyclohexylpiperazin-1-yl)ethyl)-1H-1,2,3-triazol-4-amine hydrochloride
[31] N-(2-(4-cyclohexylpiperazin-1-yl)ethyl)-1-(3-fluorophenyl)-1H-1,2,3-triazol-4-amine hydrochloride
[32] N-(2-(1,4-oxazepan-4-yl)ethyl)-1-(3-fluorophenyl)-1H-1,2,3-triazol-4-amine hydrochloride
[33] N-(2-(1,4-oxazepan-4-yl)ethyl)-1-(3,4-dichlorobenzyl)-1H-1,2,3-triazol-4-amine hydrochloride
[34] N-(2-(4-cyclohexylpiperazin-1-yl)ethyl)-1-(4-fluorobenzyl)-1H-1,2,3-triazol-4-amine
[35] 1-(4-chlorophenyl)-N-(2-morpholinoethyl)-1H-1,2,3-triazol-4-amine hydrochloride
[36] 1-(3,4-difluorobenzyl)-N-(2-morpholinoethyl)-1H-1,2,3-triazol-4-amine hydrochloride
[37] 1-(3,4-difluorobenzyl)-N-(2-(piperidin-1-yl)ethyl)-1H-1,2,3-triazol-4-amine hydrochloride
[38] 1-(2,4-difluorophenyl)-N-(2-morpholinoethyl)-1H-1,2,3-triazol-4-amine hydrochloride
[39] 1-(4-chlorophenyl)-N-(2-(piperidin-1-yl)ethyl)-1H-1,2,3-triazol-4-amine hydrochloride
[40] 1-(3,4-difluorobenzyl)-N-(2-(4,4-difluoropiperidin-1-yl)ethyl)-1H-1,2,3-triazol-4-amine hydrochloride

[41] N-(2-(4,4-difluoropiperidin-1-yl)ethyl)-1-(4-fluorobenzyl)-1H-1,2,3-triazol-4-amine hydrochloride
[42] 1-(3,4-difluorophenyl)-N-(2-morpholinoethyl)-1H-1,2,3-triazol-4-amine hydrochloride
[43] 1-(3,4-difluorophenyl)-N-(2-(4,4-difluoropiperidin-1-yl)ethyl)-1H-1,2,3-triazol-4-amine hydrochloride
[44] 1-(4-fluorophenyl)-N-(2-morpholinoethyl)-1H-1,2,3-triazol-4-amine hydrochloride
[45] 1-(3-chloro-4-fluorophenyl)-N-(2-morpholinoethyl)-1H-1,2,3-triazol-4-amine hydrochloride
[46] 1-(3-fluorophenyl)-N-(2-(piperidin-1-yl)ethyl)-1H-1,2,3-triazol-4-amine hydrochloride
[47] 1-(3,4-difluorophenyl)-N-(2-(piperidin-1-yl)ethyl)-1H-1,2,3-triazol-4-amine hydrochloride
[48] 1-(4-fluorophenyl)-N-(2-(piperidin-1-yl)ethyl)-1H-1,2,3-triazol-4-amine hydrochloride
[49] N-(2-((2RS*,6SR*)-2,6-dimethylpiperidin-1-yl)ethyl)-1-(4-fluorobenzyl)-1H-1,2,3-triazol-4-amine
[50] 1-(2,4-difluorophenyl)-N-(2-(piperidin-1-yl)ethyl)-1H-1,2,3-triazol-4-amine
[51] 1-(4-(2-(1-(3,4-dichlorophenyl)-1H-1,2,3-triazol-4-ylamino)ethyl)piperazin-1-yl)ethanone hydrochloride
[52] N-(1-(1-adamantyl)-1H-1,2,3-triazol-4-yl)-N-(2-morpholinoethyl)cyclopropanecarboxamide hydrochloride
[53] N-(1-(1-adamantyl)-1H-1,2,3-triazol-4-yl)-N-(2-morpholinoethyl)cyclohexanecarboxamide hydrochloride
[54] N-(1-(1-adamantyl)-1H-1,2,3-triazol-4-yl)-N-(2-morpholinoethyl)benzamide hydrochloride
[55] N-(1-(1-adamantyl)-1H-1,2,3-triazol-4-yl)-N-(2-morpholinoethyl)pivalamide hydrochloride
[56] N-(1-(3,4-dichlorobenzyl)-1H-1,2,3-triazol-4-yl)-N-(2-morpholinoethyl)acetamide hydrochloride
[57] N-(1-(1-adamantyl)-1H-1,2,3-triazol-4-yl)-N-(2-morpholinoethyl)acetamide hydrochloride
[58] N-(1-(3,4-dichlorophenyl)-1H-1,2,3-triazol-4-yl)-N-(2-morpholinoethyl)acetamide hydrochloride
[59] N-(1-(3,4-dichlorophenyl)-1H-1,2,3-triazol-4-yl)-N-(2-morpholinoethyl)methane sulfonamide hydrochloride
[60] 4-chloro-N-(1-(3,4-dichlorophenyl)-1H-1,2,3-triazol-4-yl)-N-(2-morpholinoethyl)benzenesulfonamide hydrochloride
[61] 1-(3,4-dichlorophenyl)-N-(2-morpholinoethyl)-N-propyl-1H-1,2,3-triazol-4-amine hydrochloride
[62] 1-benzyl-N-(2-chlorobenzyl)-N-(2-(piperidin-1-yl)ethyl)-1H-1,2,3-triazol-4-amine
[63] 1-(3,4-dichlorobenzyl)-N-(3-(piperidin-1-yl)propyl)-N-propyl-1H-1,2,3-triazol-4-amine
[64] 1-(1-adamantyl)-N-ethyl-N-(2-morpholinoethyl)-1H-1,2,3-triazol-4-amine hydrochloride
[65] 1-(3,4-dichlorophenyl)-N-ethyl-N-(2-morpholinoethyl)-1H-1,2,3-triazol-4-amine hydrochloride
[66] 1-(1-adamantyl)-N-(2-morpholinoethyl)-N-propyl-1H-1,2,3-triazol-4-amine hydrochloride
[67] N-(4-chlorobenzyl)-1-(1-adamantyl)-N-(2-morpholinoethyl)-1H-1,2,3-triazol-4-amine hydrochloride
[68] 1-(1-(3,4-dichlorophenyl)-1H-1,2,3-triazol-4-yl)-1-(2-morpholinoethyl)-3-propylthiourea hydrochloride or a pharmaceutically acceptable salt, prodrug or solvate thereof.

Another aspect of the present invention relates to a process for the production of a 1,2,3-triazole-4-amine derivatives of general formula (I).

In a preferred embodiment the 1,2,3-triazole-4-amine derivatives of general formula (I) can be obtained by the following methods:

Method A

A process is described for the preparation of a compound of formula (I):

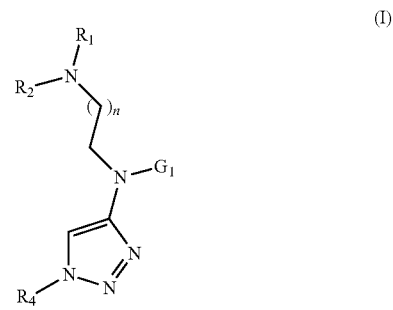

wherein $R_1$, $R_2$, $R_4$ and $G_1$ are as defined herein,
comprising the production of a compound of formula (Ia):

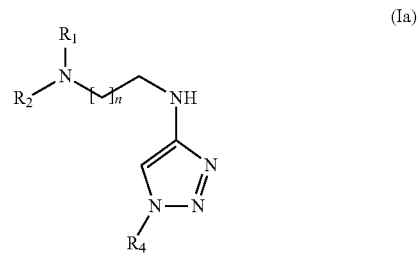

comprising the N-deprotection of a compound of general formula (IX):

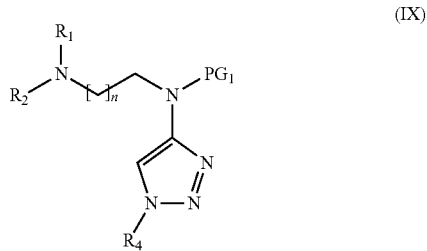

$PG_1$-Deprotection of a compound of formula (IX) is generally carried out by conventional procedures known by those skilled in the art (e.g. Greene, T. W., Wutz P. M. "Protective Groups in Organic Synthesis" Wiley, 1999).

Compounds of formula (IX) are prepared from compounds of formula (VII)

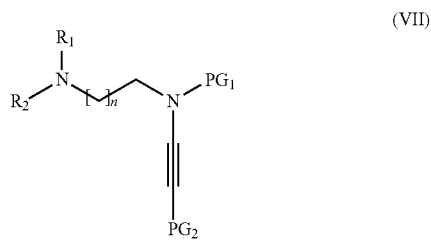

by $PG_2$-deprotection and ulterior reaction with organic azides of formula (VIII):

(VIII)

The PG$_2$-deprotection of compounds of formula (VII) is typically carried out in an aprotic solvent such as THF with an appropriate reagent such as TBAF. The subsequent cycloaddtion reaction is preferably carried out in situ by the addition of an organic azide (VIII), catalytic amounts of a Cu(I) salt such as CuI, and an excess of a base, preferably a tertiary amine such as DIPEA, at ambient temperature to give 1,4-disubstituted 1,2,3-triazoles of formula (IX) (adapted from B. K. Sharpless et al., *Angew. Chem. Int. Ed.* 2002, 41, 2596-2599). The organic azides of formula (VIII) are commercially available or can be prepared by conventional procedures.

Compounds of formula (VII) are prepared from compounds of formula (III):

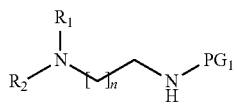
(III)

by reaction with compounds of formula (VI):

(VI)

The reaction of compounds of formula (III) and compounds of formula (VI) is carried out by methods described in the literature (Hsung. et al., *Org Lett.* 2004, 6, 1151-1154) by copper catalyzed alkynylation. PG$_2$ in formula (VI) refers to a protection group such as TMS or TIPS. Compounds of formula (VI) can be prepared by methods described in the literature (M. X. Jiang et al. *J. Am. Chem. Soc.* 2004, 126, 5970-5971).

Compounds of formula (III) can be prepared from compounds of formula (II):

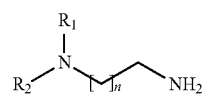
(II)

by N-protection, for instance with a Boc group. Compounds of formula (II) are commercially available or can be prepared by conventional methods.

Otherwise compounds of formula (III) can be prepared from compounds of formula (V):

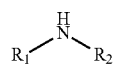
(V)

by reaction with an alkylating agent of formula (IV):

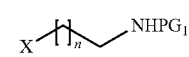
(IV)

wherein X can be Br, Cl . . . .

The N-Alkylation of compounds of formula (V) is preferably carried out in an aprotic solvent such as dichloromethane in the presence of an organic base such as DIPEA with an alkylating agent (IV).

A general synthetic route describing method A is shown in scheme 1:

Scheme 1

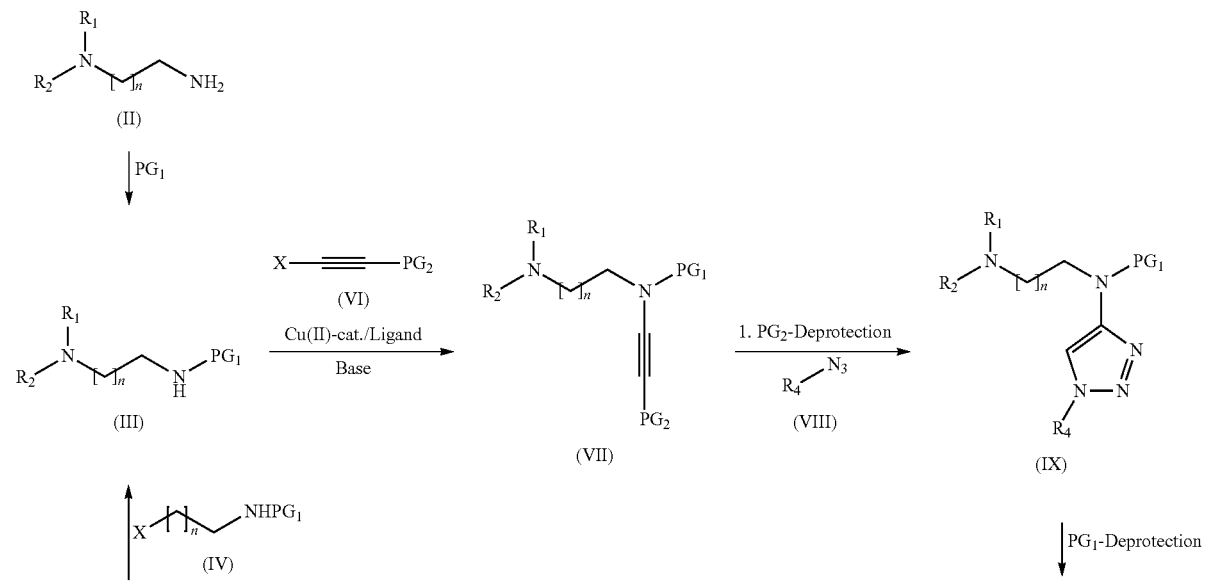

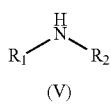

(V)

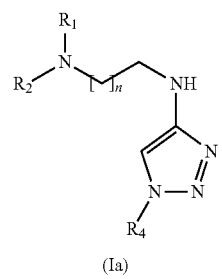

(Ia)

Method B

Another process is described for the preparation of a compound of formula (I)

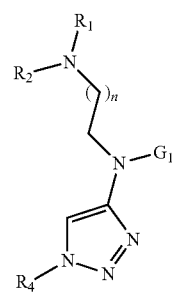

(I)

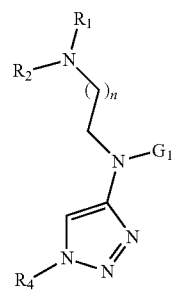

(I)

wherein $R_1$, $R_2$, $R_4$ and $G_1$ are as defined herein, comprising the production of a compound of formula (Ic):

wherein $R_1$, $R_2$, $R_4$ and $G_1$ are as defined herein, comprising the production of a compound of formula (Ib):

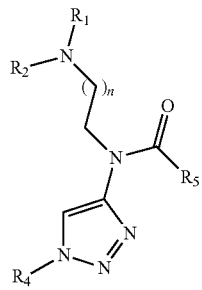

(Ib)

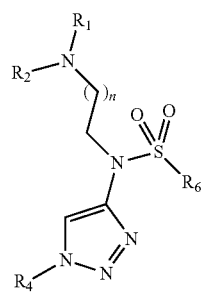

(Ic)

comprises the reaction between compounds of formula (Ia) and an acylating agent of formula (X):

are generally prepared by the reaction of compounds of formula (Ia) with compounds of formula (XI):

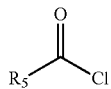

(X)

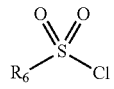

(XI)

wherein $R_5$ is as defined above Compounds of formula (X) are commercially available. Acylation of compounds of formula (Ia) is preferably carried out in an aprotic solvent such as dichloromethane in the presence of an organic base such as DIPEA with an acyl chloride of formula (X) or, alternatively, in neat acetic anhydride.

Method C

Another process is described for the preparation of a compound of formula (I)

wherein $R_6$ is as defined above. Compounds of formula (XI) are commercially available. The reaction of compounds of formula (Ia) and (XI) is preferably carried out at r.t. or solvent reflux in an aprotic solvent such as dichloromethane in the presence of an organic base such as DIPEA.

Method D

Another process is described for the preparation of a compound of formula (I)

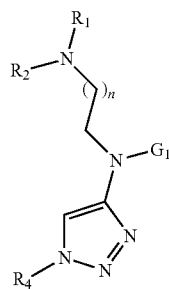

(I)

wherein $R_1$, $R_2$, $R_4$ and $G_1$ are as defined herein, comprising the production of a compound of formula (Id):

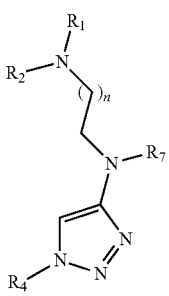

(Id)

wherein $R_7$ is as defined herein;

and which comprises the reaction of compound of formula (Ia) with an aldehyde (XII). Compounds of formula (XII) are commercially available.

Reductive amination is typically carried out in the presence of a reducing agent such as $NaBH(OAc)_3$ or $NaBH_3CN$ in a solvent such as methanol or dichloroethane at reflux temperature or under heated microwave conditions.

Method E

Another process is described for the preparation of a compound of formula (I)

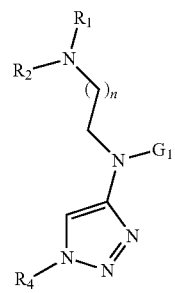

(I)

wherein $R_1$, $R_2$, $R_4$ and $G_1$ are as defined herein, comprising the production of a compound of formula (Ie):

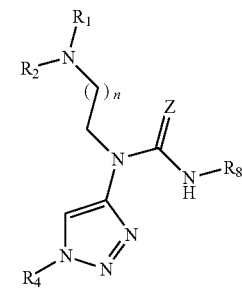

(Ie)

which are generally prepared by the reaction of compounds of formula (Ia) with compounds of formula (XIII):

$$R_8NCZ \quad \text{(XIII)}$$

wherein $R_8$ is as defined above. Compounds of formula (XIII) are commercially available.

The reaction of compounds of formula (Ia) and compounds of formula (XIII) is preferably carried out in an aprotic solvent such as dichloromethane in the presence of an organic base such as TEA or DIPEA preferably at reflux temperature.

A general synthetic route describing method B to E is shown in scheme 2:

Scheme 2

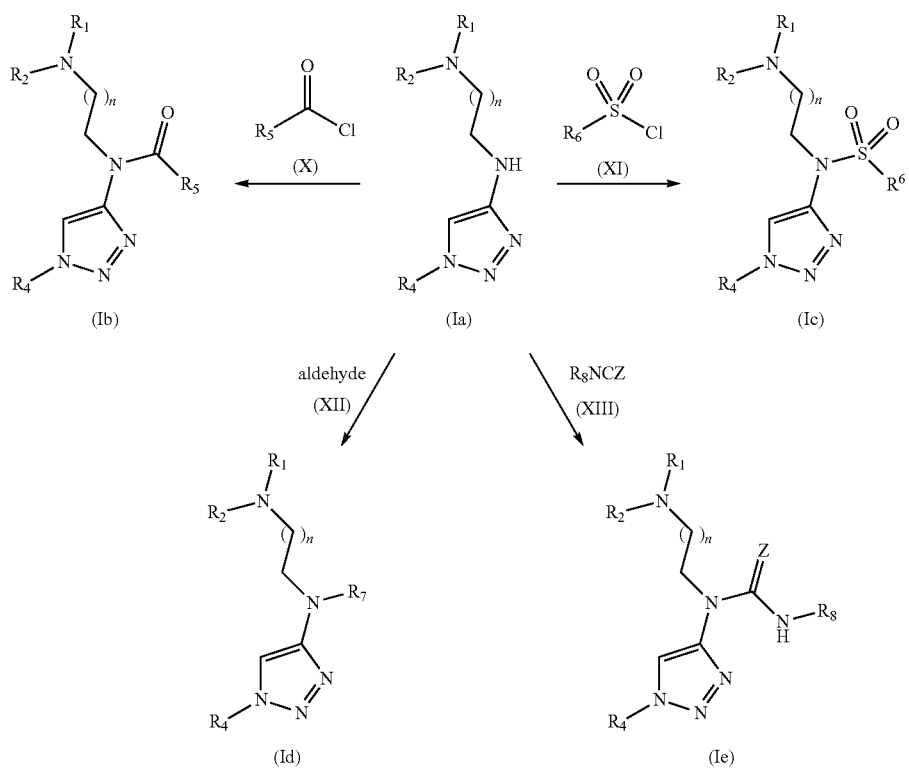

Another aspect of the present invention relates to a process for the production of 1,2,3-triazole-4-amine derivatives of general formula (I)

(I)

wherein $R_1$, $R_2$, $R_4$ and $G_1$ are as defined herein, comprising the production of a compound of formula (Ia):

(Ia)

comprising the N-deprotection of a compound of general formula (IX):

(IX)

and wherein compounds of formula (IX) are prepared from compounds of formula (VII)

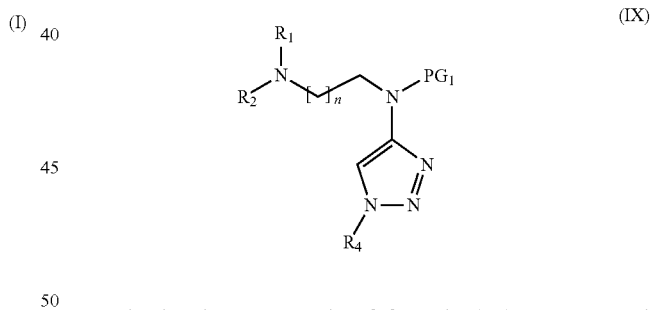

by $PG_2$-deprotection and ulterior reaction with organic azides of formula (VIII):

(VIII)

wherein, the PG$_2$-deprotection of compounds of formula (VII) can optionally be carried out in an aprotic solvent, such as THF, with an appropriate reagent, such as TBAF, and
wherein the subsequent cycloaddtion reaction is optionally carried out in situ by the addition of catalytic amounts of a Cu(I) salt, and an excess of a base, preferably a tertiary amine such as DIPEA,
wherein the compounds of formula (VII) can be prepared from compounds of formula (III):

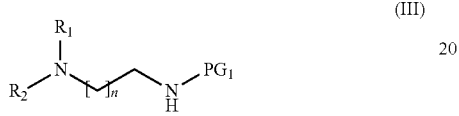
(III)

by reaction with compounds of formula (VI):

(VI)

wherein the reaction comprises copper catalyzed alkynylation.

During the processes described above the protection of sensitive groups or of reagents may be necessary and/or desirable. The introduction of conventional protective groups as well as their removal may be performed by methods well-known to those skilled in the art.

If the compounds of general formula (I) themselves are obtained as a mixture of stereoisomers, particularly enantiomers or diastereomers, said mixtures may be separated by standard procedures known to those skilled in the art, e.g. chromatographic methods or fractionalized crystallization with chiral reagents. If there are chiral centers the compounds may be prepared in racemic form, or individual enantiomers may be prepared either by enantiospecific synthesis or by resolution.

Solvates, preferably hydrates, of the compounds of general formula (I), of corresponding stereoisomers, or of corresponding salts thereof may also be obtained by standard procedures known to those skilled in the art.

The purification and isolation of the inventive compounds of general formula (I), of a corresponding stereoisomer, or salt, or solvate or any intermediate thereof may, if required, be carried out by conventional methods known to those skilled in the art, e.g. chromatographic methods or recrystallization.

If the compounds of general formula (I) themselves are obtained as a mixture of stereoisomers, particularly enantiomers or diastereomers, said mixtures may be separated by standard procedures known to those skilled in the art, e.g. chromatographic methods or fractionalized crystallization with chiral reagents. If there are chiral centers, the compounds may be prepared in racemic form, or individual enantiomers may be prepared either by enantiospecific synthesis or by resolution. Solvates, preferably hydrates, of the compounds of general formula (I), of corresponding stereoisomers, or of corresponding salts thereof may also be obtained by standard procedures known to those skilled in the art.

It has been found that the compounds of general formula (I) and given below, stereoisomers thereof, corresponding salts and corresponding solvates have high affinity to sigma receptors, i.e. they are selective ligands for the sigma receptor and act as modulators, e.g. antagonists, inverse agonists or agonists, on these receptors.

Thus, another aspect of the present invention relates to 1,2,3-triazole-4-amine derivatives of general formula (I):

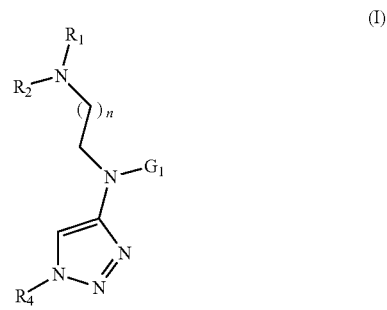
(I)

wherein:
G$_1$ is selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system; a —(C═O)—R$_5$ group; a —(SO)$_2$—R$_6$ group; a —C═Z—NH—R$_8$ group;
R$_1$ and R$_2$, identical or different, are selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;

$R_4$ is selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;

$R_5$ is selected from the group consisting of a linear or branched, saturated, substituted or unsaturated or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;

$R_6$ is selected from the group consisting of a linear or branched, saturated, substituted or unsaturated or unsubstituted aliphatic radical; a substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system;

Z is selected from S or O;

$R_8$ is a linear or branched, saturated or unsaturated, substituted or unsubstituted aliphatic radical;

n is 1, 2, 3, or 4;

optionally as one of the stereoisomers, preferably enantiomers or diastereomers, a racemate or as a mixture of at least two of the stereoisomers, preferably enantiomers and/or diastereomers, in any mixing ratio, or a corresponding salt thereof, or a corresponding solvate or prodrug thereof;

for use as a medicament.

Another aspect of the invention relates to 1,2,3-triazole-4-amine derivatives of general formula (I):

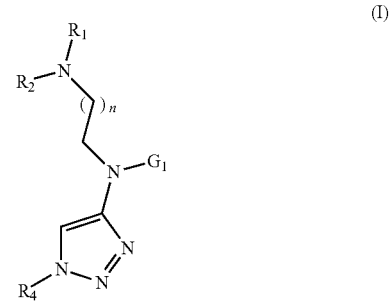

wherein:

$G_1$ is selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system; a —(C=O)—$R_5$ group; a —(SO)$_2$—$R_6$ group; a —C=Z—NH—$R_8$ group;

$R_1$ and $R_2$, identical or different, are selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;
$R_4$ is selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;
$R_5$ is selected from the group consisting of a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;
$R_6$ is selected from the group consisting of a linear or branched, saturated or unsaturated, substituted or unsubstituted aliphatic radical; a substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system;
Z is selected from S or O;
$R_8$ is a linear or branched, saturated or unsaturated, substituted or unsubstituted aliphatic radical;
n is 1, 2, 3, or 4;
optionally as of one of the stereoisomers, preferably enantiomers or diastereomers, a racemate or as a mixture of at least two of the stereoisomers, preferably enantiomers and/or diastereomers, in any mixing ratio, or a corresponding salt thereof, or a corresponding solvate or a prodrug thereof;
for use in the treatment or prophylaxis of sigma receptor mediated diseases or conditions.

The compounds of general formula (I) as described herein, their stereoisomers, corresponding salts thereof and corresponding solvates or prodrugs are toxicologically acceptable and are therefore suitable as pharmaceutical active substances for the preparation of medicaments.

Another preferred embodiment of the invention relates to 1,2,3-triazole-4-amine derivatives of general formula (I):

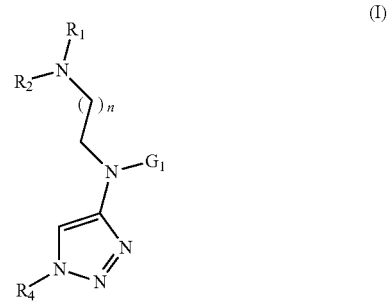

wherein:
$G_1$ is selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system; a —(C=O)—$R_5$ group; a —(SO)$_2$—$R_6$ group; a —C=Z—NH—$R_8$ group;
$R_1$ and $R_2$, identical or different, are selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;
$R_4$ is selected from the group consisting of a hydrogen atom; a linear or branched, saturated or unsaturated, substituted or unsubstituted aliphatic radical; an substituted or unsubstituted cycloalkyl group which is optionally condensed to other, substituted or unsubstituted, mono- or polycyclic ring systems; an substituted or unsubstituted carbonyl group; an substituted or unsubstituted aryl group which is optionally condensed to other, substituted or unsubstituted, mono- or polycyclic ring systems; an substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;
$R_5$ is selected from the group consisting of a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; a branched or unbranched, saturated, substituted or unsubstituted alkyl-heterocyclyl group in which the heterocyclyl group may be substituted or unsubstituted and/or condensed with a mono- or polycyclic ring system;
$R_6$ is selected from the group consisting of a linear or branched, saturated or unsaturated, substituted or unsubstituted aliphatic radical; a substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system;
Z is selected from S or O;
$R_8$ is a linear or branched, saturated or unsaturated, substituted or unsubstituted aliphatic radical;
n is 1, 2, 3, or 4;
optionally as one of the stereoisomers, preferably enantiomers or diastereomers, a racemate or in as a mixture of at least two of the stereoisomers, preferably enantiomers and/or diastereomers, in any mixing ratio, or a corresponding salt thereof, or a corresponding solvate or a prodrug thereof;
for use in the preparation of a medicament for the modulation of sigma receptors, preferably for the treatment or prophylaxis of sigma receptor mediated diseases or conditions. As can be seen above compounds according to general formulae (Ia), (Ib), (Ic), (Id) and (Ie) are compounds falling into the group of compounds according to general formula (I) as defined herein. Therefore, the abovementioned medical uses, methods of prophylaxis and/or treatment, uses in the preparation of a medicament of the present invention relating to compounds of general formula (I) also equally apply to compounds according to general formulae (Ia), (Ib), (Ic), (Id) and (Ie).

In a preferred embodiment of the invention the disease and/or condition is selected from diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, for the treatment and prophylaxis of pain, especially neuropathic pain, inflammatory pain or other pain conditions involving allodynia and/or hyperalgesia.

In a preferred embodiment of the invention the disease and/or condition is selected from the group consisting of pain, preferably neuropathic pain, inflammatory pain or other pain conditions involving allodynia and/or hyperalgesia.

In an even more preferred embodiment of the invention the disease and/or condition is allodynia and/or hyperalgesia.

In a most preferred embodiment of the invention the disease and/or condition is mechanical or thermal allodynia, preferably mechanical allodynia.

Another aspect of the present invention relates to a pharmaceutical composition comprising one or more compounds of general formula (I), or isomers, solvates or prodrugs thereof, and at least one pharmaceutically acceptable excipient.

One preferred pharmaceutically acceptable form of the compounds of the invention is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of the present invention relates to a medicament comprising at least one compound of general formula (I) given above, said compound being optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof; or a prodrug thereof.

Another aspect of the invention is a medicament comprising at least one combination of compounds according to the invention and optionally one or more pharmaceutically acceptable excipients.

Said medicament may also comprise any combination of one or more of the compounds of general formula (I) given above, stereoisomers thereof, physiologically acceptable salts thereof or physiologically acceptable solvates or pro-drugs thereof.

The compounds of the invention, that is, the 1,2,3-triazole-4-amine derivatives of general formula (I) are contemplated for medical uses as described herein, be it in the form of a pharmaceutical composition as described herein, a medicament as described herein or any other pharmaceutically acceptable administration form suitable for administration to a patient.

In the context of the present invention, the term "patient" refers to a mammal, preferably a human.

Another aspect of the invention relates to 1,2,3-triazole-4-amine derivatives of general formula (I) for the use(s) and/or medical use(s) described herein, the 1,2,3-triazole-4-amine derivatives of general formula (I) optionally being in the form of said pharmaceutical composition, said medicament, or said pharmaceutical administration form, wherein the disease or condition is a sigma-1 mediated disease or condition.

Another aspect of the invention relates to 1,2,3-triazole-4-amine derivatives of general formula (I) for the medical use(s) described herein, the 1,2,3-triazole-4-amine derivatives of general formula (I) optionally being in the form of said pharmaceutical composition, said medicament, or said pharmaceutical administration form, wherein the disease and/or condition is selected from diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, for the treatment and prophylaxis of pain, especially neuropathic pain, inflammatory pain or other pain conditions involving allodynia and/or hyperalgesia.

A preferred embodiment of the invention relates to 1,2,3-triazole-4-amine derivatives of general formula (I) for the medical use(s) described herein, the 1,2,3-triazole-4-amine derivatives of general formula (I) optionally being in the form of said pharmaceutical composition, said medicament, or said pharmaceutical administration form, wherein the disease and/or condition is selected from the group consisting of pain, preferably neuropathic pain, inflammatory pain or other pain conditions involving allodynia and/or hyperalgesia.

An even more preferred embodiment of the invention relates to 1,2,3-triazole-4-amine derivatives of general formula (I) for the medical use(s) described herein, the 1,2,3-triazole-4-amine derivatives of general formula (I) optionally being in the form of said pharmaceutical composition, said medicament, or said pharmaceutical administration form, wherein the disease and/or condition is allodynia and/or hyperalgesia.

A most preferred embodiment of the invention relates to 1,2,3-triazole-4-amine derivatives of general formula (I) for the medical use(s) described herein, the 1,2,3-triazole-4-amine derivatives of general formula (I) optionally being in the form of said pharmaceutical composition, said medicament, or said pharmaceutical administration form, wherein the disease and/or condition is mechanical or thermal allodynia, preferably mechanical allodynia.

Another aspect of the present invention refers to a method for the prophylaxis and/or treatment of diarrhea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, for the treatment and prophylaxis of pain, especially neuropathic pain, inflammatory pain or other pain conditions involving allodynia and/or hyperalgesia, the method comprising administering to the subject at least one compound of general formula (I) as described above and optionally at least one further active substance and/or optionally at least one auxiliary substance to the subject.

A preferred embodiment of the invention relates to a method for the prophylaxis and/or treatment of pain, especially neuropathic pain, inflammatory pain or other pain conditions involving allodynia and/or hyperalgesia, the method comprising administering to the subject at least one compound of general formula (I) as described above and optionally at least one further active substance and/or optionally at least one auxiliary substance to the subject.

A most preferred embodiment of the present invention relates to method for the prophylaxis and/or treatment of mechanical or thermal allodynia, preferably mechanical allodynia., the method comprising administering to the subject at least one compound of general formula (I) as described above and optionally at least one further active substance and/or optionally at least one auxiliary substance to the subject.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

Solid oral compositions (which are preferred as are liquid ones) may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to the methods well known in normal pharmaceutical practice, in particular with an enteric coating. The mentioned formulations will be prepared using standard methods such as those described or referred to in the Spanish and US Pharmacopeias and similar reference texts.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The medicament according to the present invention may be in any form suitable for the application to humans and/or animals, preferably humans including infants, children and adults and can be produced by standard procedures known to those skilled in the art. The composition of the medicament may vary depending on the route of administration.

The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously. Solid oral compositions (which are preferred as are liquid ones) may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to the methods well known in normal pharmaceutical practice, in particular with an enteric coating. The mentioned formulations will be prepared using standard methods such as those described or referred to in the Spanish and US Pharmacopeias and similar reference texts.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release. The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount. The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The present invention is illustrated below with the aid of examples. These illustrations are given solely by way of example and do not limit the general spirit of the present invention.

EXAMPLES

Compounds corresponding to preferred embodiments according to general formula (I) can be prepared as follows:

Preparation of Compounds of Formula (Ia)

Example 1

Synthesis of 1-(4-(2-(1-(3,4-dichlorobenzyl)-1H-1,2,3-triazol-4-ylamino)ethyl)piperazin-1-yl)ethanone hydrochloride 1. Synthesis of tert-butyl 2-(4-acetylpiperazin-1-yl)ethylcarbamate

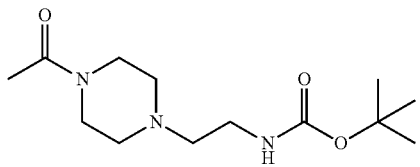 [SMILES: CC(=O)N1CCN(CCNC(=O)OC(C)(C)C)CC1]

To a stirred solution of tert-butyl 2-bromoethylcarbamate (4.37 g, 19.5 mmol) in dry $CH_2Cl_2$ (40 mL) 1-(piperazin-1-yl)ethanone (5 g, 39.0 mmol) was added, followed by TEA (4.07 mL, 29.2 mmol). The reaction mixture was heated under reflux for 16 h. After cooling back to r.t., the reaction was quenched with $H_2O$ and extracted with $CH_2Cl_2$ twice. The combined organic fractions were dried over sodium sulphate and the solvent removed under reduced pressure to give tert-butyl 2-(4-acetylpiperazin-1-yl)ethylcarbamate 5.39 g (quant.) as a red oil. The product was used without further purification in the next step. $^1$H NMR ($CD_3OD$) δ ppm: 3.68-3.48 (m, 4H), 3.20 (t, J=6.6 Hz, 2H), 2.56-2.37 (m, 6H), 2.09 (s, 3H), 1.44 (s, 9H).

2. Synthesis of tert-butyl 2-(4-acetylpiperazin-1-yl) ethyl((triisopropylsilyl) ethynyl)carbamate

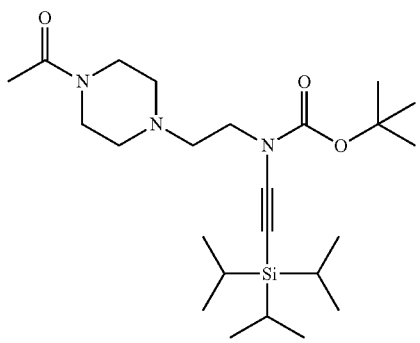 [SMILES: CC(=O)N1CCN(CCN(C#C[Si](C(C)C)(C(C)C)C(C)C)C(=O)OC(C)(C)C)CC1]

A schlenk tube was charged with tert-butyl 2-(4-acetylpiperazin-1-yl)ethylcarbamate (5.39 g, 19.9 mmol, 1 equiv.), $CuSO_4.5H_2O$ (532 mg, 1.98 mmol, 0.1 equiv.), $K_3PO_4$ (8.43 g, 40 mmol, 2 equiv.) and 1,10-phenanthroline (715 mg, 4 mmol, 0.2 equiv.), evacuated and backfilled with argon. Then a solution of (bromoethynyl)triisopropylsilane (5.71 g, 21.8 mmol, 1.1 equiv.) dissolved in dry toluene (80 mL) was added and the reaction solution was heated at 110° C. for 2 days. The solvent was removed under reduced pressure and the crude product was taken up in AcOEt and partitioned between $H_2O$ and AcOEt. The aqueous phase was additionally extracted with AcOEt twice. The combined organic fractions were dried over sodium sulphate and the solvent removed under reduced pressure after filtration. The residue was purified by combiflash chromatography (SiO$_2$, c-Hexane/AcOEt up to 10%) to give tert-butyl 2-(4-acetylpiperazin-1-yl)ethyl((triisopropylsilyl)ethynyl)carbamate as a yellow oil (3.83 g, 43%). $^1$H NMR (CDCl$_3$) δ ppm: 3.69-3.50 (m, 4H), 3.44 (t, J=5.0 Hz, 2H), 2.67 (t, J=6.5 Hz, 2H), 2.60-2.38 (m, 4H), 2.07 (s, 3H), 1.48 (s, 9H), 1.23-0.92 (m, 21H).

3. Synthesis of tert-butyl 2-(4-acetylpiperazin-1-yl)ethyl(1-(3,4-dichlorobenzyl)-1H-1,2,3-triazol-4-yl)carbamate

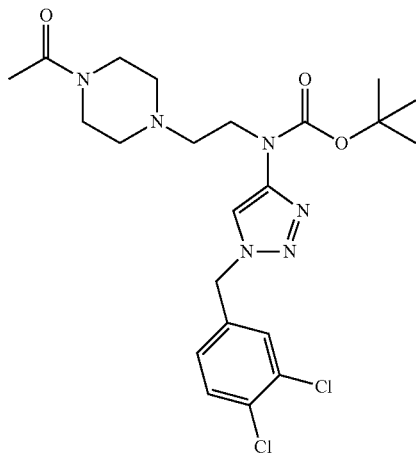 [SMILES: CC(=O)N1CCN(CCN(C(=O)OC(C)(C)C)c2cn(Cc3ccc(Cl)c(Cl)c3)nn2)CC1]

A stirred solution of tert-butyl 2-(4-acetylpiperazin-1-yl)ethyl(ethynyl)carbamate (261 mg, 0.884 mmol) in dry THF (15 mL) was cooled to 0° C. under an argon atmosphere, and TBAF (1 M in THF, 0.884 mmol) was added dropwise. The reaction mixture was stirred at 0° C. for 30 min. and additionally at r.t. for 10 min, after which the TIPS deprotection had been completed as judged by TLC. At this point CuI (84.1 mg 0.442 mmol) and 4-(azidomethyl)-1,2-dichlorobenzene (214 mg, 1.06 mmol) were added followed by DIPEA (151 µL, 0.884 mmol) and the reaction mixture stirred at r.t. overnight. The solvent was removed under reduced pressure and the crude product taken up in AcOEt. Saturated aq. NaHCO$_3$ was added and the phases were separated. The aqueous phase was additionally extracted with AcOEt. The combined organic fractions were dried over MgSO$_4$ and the solvent removed under reduced pressure after filtration. The residue was purified by combiflash column chromatography (SiO$_2$, c-Hexane/AcOEt up to 40%) to give tert-butyl 2-(4-acetylpiperazin-1-yl)ethyl(1-(3,4-dichlorobenzyl)-1H-1,2,3-triazol-4-yl)carbamate (323 mg, 73%) as a yellow solid. $^1$H NMR (CDCl$_3$) δ ppm: 7.85 (s, 1H), 7.44 (d, J=8.3 Hz, 1H), 7.37 (d, J=2.1 Hz, 1H), 7.12 (dd, J=8.3, 2.1 Hz, 1H), 5.39 (s, 2H), 4.28-4.10 (m, 2H), 3.74-3.33 (m, 4H), 2.88-2.41 (m, 4H), 2.08 (s, 3H), 1.51 (s, 9H).

4. Synthesis of 1-(4-(2-(1-(3,4-dichlorobenzyl)-1H-1,2,3-triazol-4-ylamino)ethyl)piperazin-1-yl)ethanone hydrochloride

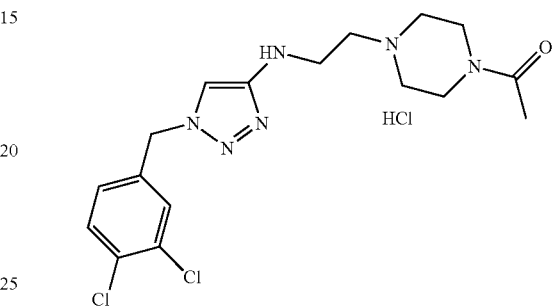

tert-Butyl 2-(4-acetylpiperazin-1-yl)ethyl(1-(3,4-dichlorobenzyl)-1H-1,2,3-triazol-4-yl)carbamate (250 mg, 0.503 mmol) was dissolved in CH$_2$Cl$_2$ (10 mL) and TFA (1 mL, 13.46 mmol) was added dropwise. The reaction mixture was stirred at r.t. until the deprotection process had been completed as judged by TLC. The reaction mixture was quenched with saturated aq. NaHCO$_3$ and the product extracted with CH$_2$Cl$_2$ twice. The combined organic fractions were dried over sodium sulphate and the solvent was removed under reduced pressure to give 1-(4-(2-(1-(3,4-dichlorobenzyl)-1H-1,2,3-triazol-4-ylamino)ethyl)piperazin-1-yl)ethanone as yellow oil (184 mg, 92%). This compound (184 mg, 0.463 mmol) was dissolved in acetone (2 mL) and a HCl solution (2 M in ether, 254 µL, 0.509 mmol) was added dropwise. After stirring for 30 min. at r.t., the white solid formed was filtered off and dried in vacuo to give 1-(4-(2-(1-(3,4-dichlorobenzyl)-1H-1,2,3-triazol-4-ylamino)ethyl)piperazin-1-yl)ethanone hydrochloride (119 mg, 59%) as white solid. $^1$H NMR (CD$_3$OD) δ ppm: 7.54 (d, J=8.3 Hz, 1H), 7.50 (d, J=2.1 Hz, 1H), 7.38 (s, 1H), 7.27 (dd, J=8.3, 2.1 Hz, 1H), 5.48 (s, 2H), 4.11-3.22 (m, 8H), 3.59 (t, J=5.7 Hz, 2H), 3.42 (t, J=5.7 Hz, 2H), 2.15 (s, 3H).

Examples 2-51 were prepared following the same method as described in example 1:

| Ex. | Structure | Chem. name | 1 H NMR |
|---|---|---|---|
| 2 | ![structure] | 1-(3,4-dichlorophenyl)-N-(2-(piperidin-1-yl)ethyl)-1H-1,2,3-triazol-4-amine hydrochloride | $^1$H NMR (CDCl$_3$) δ ppm: 11.62 (bs, 2H), 7.71 (s, 1H), 7.60 (d, J = 2.2 Hz, 1H), 7.52 (d, J = 8.5 Hz, 1H), 7.42 (dd, J = 8.5, 2.2 Hz, 1H), 4.02 (t, J = 5.4 Hz, 2H), 3.74-3.56 (m, 2H), 3.45-3.25 (m, 2H), 2.85-2.66 (m, 2H), 2.43-2.20 (m, 2H), 2.00-1.77 (m, 3H), 1.58-1.33 (m, 1H). |

-continued

| Ex. | Structure | Chem. name | 1 H NMR |
|---|---|---|---|
| 3 | (structure) | 1-(2,4-dichlorophenyl)-N-(2-(piperidin-1-yl)ethyl)-1H-1,2,3-triazol-4-amine hydrochloride | $^1$H NMR (CDCl$_3$) δ ppm: 11.68 (bs, 2H), 8.13 (s, 1H), 7.96 (s, 1H), 7.73-7.53 (m, 2H), 4.01 (t, J = 5.7 Hz, 2H), 3.69-3.51 (m, 2H), 3.37-3.20 (m, 2H), 2.89-2.60 (m, 2H), 2.48-2.20 (m, 2H), 2.03-1.69 (m, 3H), 1.59-1.30 (m, 1H). |
| 4 | (structure) | 1-benzyl-N-(2-(piperidin-1-yl)ethyl)-1H-1,2,3-triazol-4-amine hydrochloride | $^1$H NMR (CDCl$_3$) δ ppm: 11.53 (bs, 2H), 7.40-7.27 (m, 5H), 7.08 (s, 1H), 5.37 (s, 2H), 3.83 (t, J = 5.5 Hz, 2H), 3.68-3.52 (m, 2H), 3.25 (t, J = 5.3 Hz, 2H), 2.85-2.53 (m, 2H), 2.47-2.12 (m, 2H), 2.01-1.66 (m, 3H), 1.54-1.14 (m, 1H). |
| 5 | (structure) | 1-(3,4-dichlorophenyl)-N-(2-morpholinoethyl)-1H-1,2,3-triazol-4-amine hydrochloride | $^1$H NMR (CD$_3$OD) δ ppm: 8.07 (d, J = 2.4 Hz, 1H), 7.94 (s, 1H), 7.81 (dd, J = 8.8, 2.5 Hz, 1H), 7.73 (d, J = 8.9 Hz, 1H), 4.13-4.02 (m, 2H), 3.91-3.79 (m, 2H), 3.66 (t, J = 5.9 Hz, 2H), 3.66-3.58 (m, 2H), 3.47 (t, J = 5.9 Hz, 2H), 3.31-3.20 (m, 2H). |
| 6 | (structure) | 1-(1-adamantyl)-N-(2-morpholinoethyl)-1H-1,2,3-triazol-4-amine hydrochloride | $^1$H NMR (CDCl$_3$) δ ppm: 7.36 (s, 1H), 4.45-4.13 (m, 2H), 4.11-3.96 (m, 2H), 3.92 (t, J = 5.6 Hz, 2H), 3.66-3.45 (m, 2H), 3.37 (t, J = 5.6 Hz, 2H), 3.15-2.87 (m, 3H), 2.33-2.23 (m, 3H), 2.23-2.14 (m, 6H), 1.87-1.63 (m, 6H). |
| 7 | (structure) | 1-(3,4-dichlorobenzyl)-N-(2-morpholinoethyl)-1H-1,2,3-triazol-4-amine hydrochloride | $^1$H NMR (CD$_3$OD) δ ppm: 7.55 (d, J = 8.4 Hz, 1H), 7.53 (d, J = 1.9 Hz, 1H), 7.48 (s, 1H), 7.30 (dd, J = 8.3, 2.2 Hz, 1H), 5.52 (s, 2H), 4.10-3.98 (m, 2H), 3.91-3.77 (m, 2H), 3.59 (t, J = 5.8 Hz, 2H), 3.58-3.50 (m, 2H), 3.41 (t, J = 5.9 Hz, 2H), 3.28-3.15 (m, 2H). |
| 8 | (structure) | 1-benzyl-N-(2-morpholinoethyl)-1H-1,2,3-triazol-4-amine hydrochloride | $^1$H NMR (CDCl$_3$) δ ppm: 7.44-7.29 (m, 5H), 7.00 (s, 1H), 5.38 (s, 2H), 4.31 (t, J = 12.4 Hz, 2H), 4.02-3.90 (m, 2H), 3.90-3.78 (m, 2H), 3.65-3.44 (m, 2H), 3.42-3.22 (m, 2H), 3.07-2.75 (m, 2H). |

| Ex. | Chem. name | 1 H NMR |
|---|---|---|
| 9 | 1-(3,4-dichlorobenzyl)-N-(2-(piperidin-1-yl)ethyl)-1H-1,2,3-triazol-4-amine hydrochloride | $^1$H NMR (CDCl$_3$) δ ppm: 11.27 (bs, 1H), 7.61 (s, 1H), 7.49 (d, J = 8.3 Hz, 1H), 7.45 (d, J = 1.2 Hz, 1H), 7.21 (dd, J = 9.0, 1.2 Hz, 1H), 5.39 (s, 2H), 4.12-3.84 (m, 2H), 3.72-3.47 (m, 2H), 3.41-3.12 (m, 2H), 2.89-2.64 (m, 2H), 2.32-2.11 (m, 2H), 2.02-1.80 (m, 3H), 1.61-1.31 (m, 1H). |
| 10 | 1-(3,4-dichlorobenzyl)-N-(3-(piperidin-1-yl)propyl)-1H-1,2,3-triazol-4-amine hydrochloride | $^1$H NMR (CD$_3$OD) δ ppm: 7.68 (s, 1H), 7.61 (d, J = 2.1 Hz, 1H), 7.58 (d, J = 8.3 Hz, 1H), 7.35 (dd, J = 8.3, 2.1 Hz, 1H), 3.53 (d, J = 11.9 Hz, 2H), 3.39-3.24 (m, 2H), 3.24-3.13 (m, 2H), 2.93 (td, J = 12.2, 3.2 Hz, 2H), 2.14-1.74 (m, 6H), 1.63-1.23 (m, 2H). |
| 11 | 1-(3-fluorophenyl)-N-(2-morpholinoethyl)-1H-1,2,3-triazol-4-amine hydrochloride | $^1$H NMR (CD$_3$OD) δ ppm: 7.98 (s, 1H), 7.72-7.52 (m, 3H), 7.24 (tdd, J = 8.4, 2.5, 1.1 Hz, 1H), 4.17-4.02 (m, 2H), 3.97-3.78 (m, 2H), 3.68 (t, J = 5.9 Hz, 2H), 3.65-3.55 (m, 2H), 3.47 (t, J = 5.9 Hz, 2H), 3.32-3.17 (m, 2H). |
| 12 | N-(2-(azepan-1-yl)ethyl)-1-(3,4-dichlorobenzyl)-1H-1,2,3-triazol-4-amine hydrochloride | $^1$H NMR (CD$_3$OD) δ ppm: 7.59-7.47 (m, 3H), 7.30 (dd, J = 8.2, 2.2 Hz, 1H), 5.52 (s, 2H), 3.63-3.47 (m, 4H), 3.39 (t, J = 5.9 Hz, 2H), 3.30-3.19 (m, 2H), 2.00-1.86 (m, 4H), 1.85-1.67 (m, 4H). |
| 13 | N-(2-(azepan-1-yl)ethyl)-1-(3-fluorophenyl)-1H-1,2,3-triazol-4-amine hydrochloride | $^1$H NMR (CD$_3$OD) δ ppm: 7.94 (s, 1H), 7.75-7.50 (m, 3H), 7.23 (td, J = 8.2, 1.9 Hz, 1H), 3.69-3.51 (m, 4H), 3.50-3.40 (m, 2H), 3.31-3.25 (m, 2H), 2.05-1.89 (m, 4H), 1.86-1.68 (m, 4H). |

-continued

| Ex. | Structure | Chem. name | 1 H NMR |
|---|---|---|---|
| 14 | 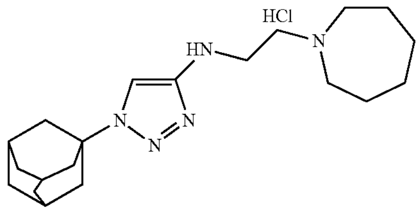 [SMILES: c1c(NCCN2CCCCCC2)nnn1C12CC3CC(CC(C3)C1)C2 ; Cl] | N-(2-(azepan-1-yl)ethyl)-1-(1-adamantyl)-1H-1,2,3-triazol-4-amine hydrochloride | $^1$H NMR (CD$_3$OD) δ ppm: 7.95 (s, 1H), 3.63 (t, J = 6.2 Hz, 2H), 3.61-3.50 (m, 2H), 3.42 (t, J = 6.2 Hz, 2H), 3.32-3.22 (m, 2H), 2.32-2.25 (m, 9H), 2.01-1.91 (m, 4H), 1.91-1.81 (m, 6H), 1.81-1.68 (m, 4H). |
| 15 | 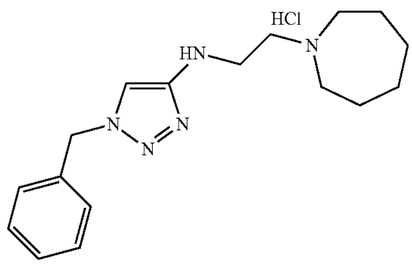 [SMILES: c1ccc(Cn2cc(NCCN3CCCCCC3)nn2)cc1 ; Cl] | N-(2-(azepan-1-yl)ethyl)-1-benzyl-1H-1,2,3-triazol-4-amine hydrochloride | $^1$H NMR (CD$_3$OD) δ ppm: 7.46-7.31 (m, 6H), 5.51 (s, 2H), 3.54 (t, J = 5.8 Hz, 2H), 3.52-3.47 (m, 2H), 3.38 (t, J = 5.9 Hz, 2H), 3.35-3.17 (m, 2H), 2.02-1.84 (m, 4H), 1.85-1.66 (m, 4H). |
| 16 | 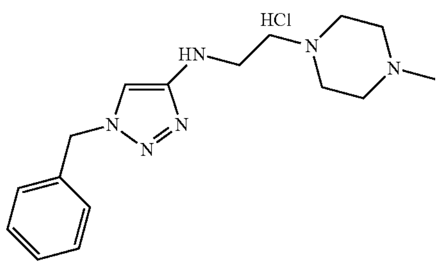 [SMILES: CN1CCN(CCNc2cn(Cc3ccccc3)nn2)CC1 ; Cl] | 1-benzyl-N-(2-(4-methylpiperazin-1-yl)ethyl)-1H-1,2,3-triazol-4-amine hydrochloride | $^1$H NMR (CD$_3$OD) δ ppm: 7.42 (s, 1H), 7.41-7.29 (m, 5H), 5.50 (s, 2H), 3.76-3.45 (m, 8H), 3.61-3.50 (m, 2H), 3.43-3.33 (m, 2H), 2.99 (s, 3H). |
| 17 | 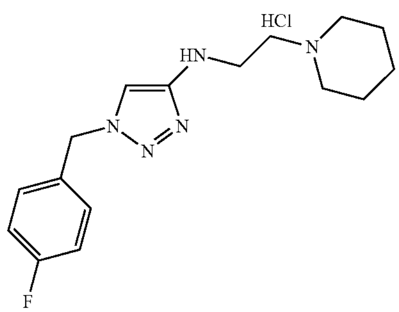 [SMILES: Fc1ccc(Cn2cc(NCCN3CCCCC3)nn2)cc1 ; Cl] | 1-(4-fluorobenzyl)-N-(2-(piperidin-1-yl)ethyl)-1H-1,2,3-triazol-4-amine hydrochloride | $^1$H NMR (CD$_3$OD) δ ppm: 7.57 (s, 1H), 7.44 (dd, J = 8.7, 5.3 Hz, 2H), 7.13 (t, J = 8.7 Hz, 2H), 5.54 (s, 2H), 3.64-3.59 (m, 2H), 3.58 (t, J = 6.1 Hz, 2H), 3.32 (t, J = 6.3 Hz, 2H), 3.00 (td, J = 12.4, 3.2 Hz, 2H), 1.99-1.74 (m, 5H), 1.63-1.46 (m, 1H). |
| 18 | 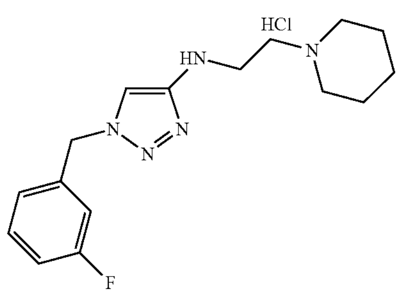 [SMILES: Fc1cccc(Cn2cc(NCCN3CCCCC3)nn2)c1 ; Cl] | 1-(3-fluorobenzyl)-N-(2-(piperidin-1-yl)ethyl)-1H-1,2,3-triazol-4-amine hydrochloride | $^1$H NMR (CD$_3$OD) δ ppm: 7.40 (td, J = 8.0, 5.8 Hz, 2H), 7.36 (s, 1H), 7.15 (dt, J = 8.3, 1.1 Hz, 1H), 7.14-7.01 (m, 2H), 5.50 (s, 2H), 3.65-3.55 (m, 2H), 3.55 (t, J = 5.9 Hz, 2H), 3.33 (t, J = 6.2 Hz, 2H), 3.00 (td, J = 12.3, 3.3 Hz, 2H), 2.03-1.89 (m, 2H), 1.89-1.78 (m, 3H), 1.62-1.47 (m, 1H). |
| 19 | 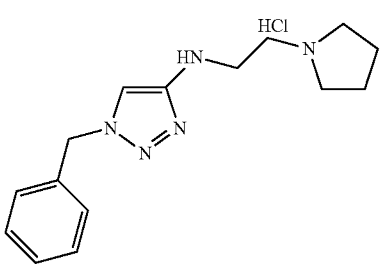 [SMILES: c1ccc(Cn2cc(NCCN3CCCC3)nn2)cc1 ; Cl] | 1-benzyl-N-(2-(pyrrolidin-1-yl)ethyl)-1H-1,2,3-triazol-4-amine hydrochloride | $^1$H NMR (CD$_3$OD) δ ppm: 7.80 (s, 1H), 7.48-7.35 (m, 5H), 5.62 (s, 2H), 3.79-3.66 (m, 2H), 3.59 (t, J = 6.0 Hz, 2H), 3.44 (t, J = 6.0 Hz, 2H), 3.20-3.05 (m, 2H), 2.22-2.11 (m, 2H), 2.11-1.96 (m, 2H). |

| Ex. | Structure | Chem. name | 1 H NMR |
| --- | --- | --- | --- |
| 20 | 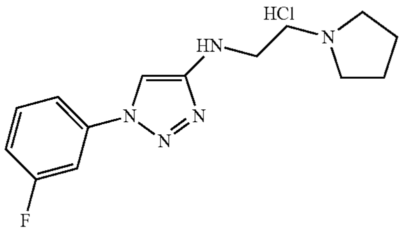 [SMILES: Fc1cccc(-n2cc(NCCN3CCCC3)nn2)c1 ; Cl] | 1-(3-fluorophenyl)-N-(2-(pyrrolidin-1-yl)ethyl)-1H-1,2,3-triazol-4-amine hydrochloride | $^1$H NMR (CD$_3$OD) δ ppm: 7.91 (s, 1H), 7.72-7.51 (m, 3H), 7.22 (tdd, J = 8.5, 2.6, 1.1 Hz, 1H), 3.82-3.68 (m, 2H), 3.61 (t, J = 5.7 Hz, 2H), 3.49 (t, J = 5.5 Hz, 2H), 3.27-3.09 (m, 2H), 2.27-2.08 (m, 2H), 2.12-1.98 (m, 2H). |
| 21 | 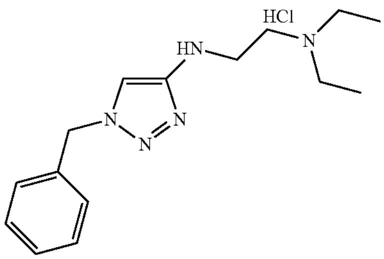 [SMILES: CCN(CC)CCNc1cn(Cc2ccccc2)nn1 ; Cl] | N1-(1-benzyl-1H-1,2,3-triazol-4-yl)-N2,N2-diethylethane-1,2-diamine hydrochloride | $^1$H NMR (CD$_3$OD) δ ppm: 7.41 (s, 1H), 7.39-7.26 (m, 5H), 5.50 (s, 2H), 3.52 (t, J = 5.7 Hz, 2H), 3.38 (t, J = 5.5 Hz, 2H), 3.32-3.22 (m, 4H), 1.32 (t, J = 6.8 Hz, 6H). |
| 22 | 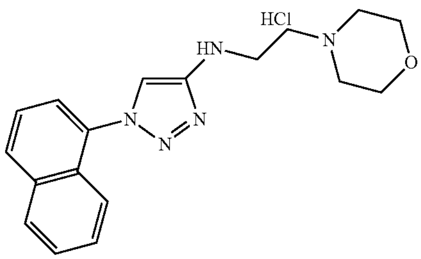 [SMILES: c1ccc2c(-n3cc(NCCN4CCOCC4)nn3)cccc2c1 ; Cl] | N-(2-morpholinoethyl)-1-(naphthalen-1-yl)-1H-1,2,3-triazol-4-amine hydrochloride | $^1$H NMR (CD$_3$OD) δ ppm: 8.31 (d, J = 2.3 Hz, 1H), 8.12 (s, 1H), 8.09 (d, J = 8.8 Hz, 1H), 8.04-7.94 (m, 3H), 7.66-7.55 (m, 2H), 4.14-4.03 (m, 2H), 3.93-3.81 (m, 2H), 3.71 (t, J = 5.9 Hz, 2H), 3.67-3.59 (m, 2H), 3.50 (t, J = 5.9 Hz, 2H), 3.30-3.22 (m, 2H). |
| 23 | 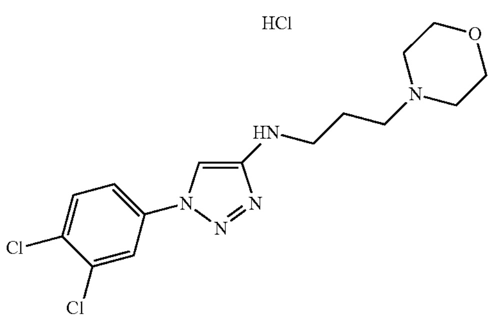 [SMILES: Cl ; Clc1ccc(-n2cc(NCCCN3CCOCC3)nn2)cc1Cl] | 1-(3,4-dichlorophenyl)-N-(3-morpholinopropyl)-1H-1,2,3-triazol-4-amine hydrochloride | $^1$H NMR (CD$_3$OD) δ ppm: 8.08 (d, J = 2.4 Hz, 1H), 7.88 (s, 1H), 7.81 (dd, J = 8.8, 2.5 Hz, 1H), 7.73 (d, J = 8.9 Hz, 1H), 4.08 (dd, J = 13.2, 3.3 Hz, 2H), 3.84-3.74 (m, 2H), 3.56-3.48 (m, 2H), 3.35 (t, J = 6.3 Hz, 2H), 3.31-3.29 (m, 2H), 3.17 (td, J = 12.2, 3.4 Hz, 2H), 2.17-2.05 (m, 2H). |
| 24 | 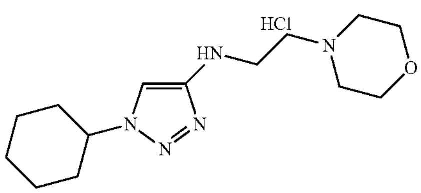 [SMILES: c1c(NCCN2CCOCC2)nnn1C1CCCCC1 ; Cl] | 1-cyclohexyl-N-(2-morpholinoethyl)-1H-1,2,3-triazol-4-amine hydrochloride | $^1$H NMR (CD$_3$OD) δ ppm: 7.45 (s, 1H), 4.39 (tt, J = 11.7, 3.9 Hz, 1H), 4.09-3.79 (m, 4H), 3.58-3.15 (m, 4H), 3.58 (dd, J = 6.3, 5.2 Hz, 2H), 3.41 (dd, J = 6.4, 5.2 Hz, 2H), 2.18-2.09 (m, 2H), 1.97-1.87 (m, 2H), 1.87-1.68 (m, 3H), 1.50 (qt, J = 12.9, 3.4 Hz, 2H), 1.32 (qt, J = 12.7, 3.6 Hz, 1H). |

| Ex. | Structure | Chem. name | 1 H NMR |
|---|---|---|---|
| 25 | 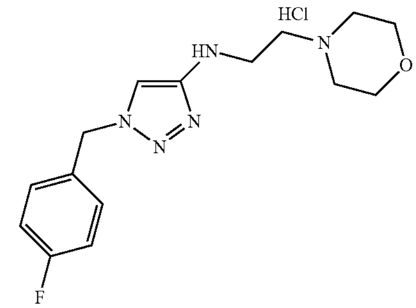 [SMILES: Fc1ccc(Cn2cc(NCCN3CCOCC3)nn2)cc1 ; Cl] | 1-(4-fluorobenzyl)-N-(2-morpholinoethyl)-1H-1,2,3-triazol-4-amine hydrochloride | $^1$H NMR (CD$_3$OD) δ ppm: 7.61 (s, 1H), 7.45 (dd, J = 8.7, 5.3 Hz, 2H), 7.14 (t, J = 8.8 Hz, 2H), 5.55 (s, 2H), 4.12-3.96 (m, 2H), 3.96-3.78 (m, 2H), 3.61 (t, J = 5.9 Hz, 2H), 3.58-3.48 (m, 2H), 3.40 (t, J = 5.9 Hz, 2H), 3.28-3.15 (m, 2H). |
| 26 | 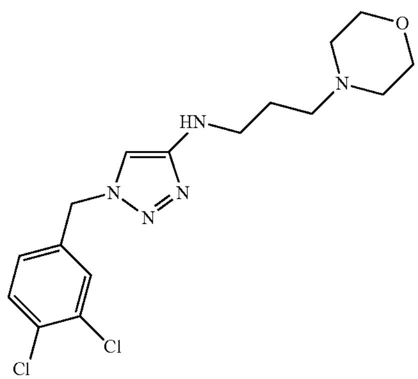 [SMILES: Clc1ccc(Cn2cc(NCCCN3CCOCC3)nn2)cc1Cl] | 1-(3,4-dichlorobenzyl)-N-(3-morpholinopropyl)-1H-1,2,3-triazol-4-amine | $^1$H NMR (CD$_3$OD) δ ppm: 7.52 (d, J = 8.3 Hz, 1H), 7.47 (d, J = 2.0 Hz, 1H), 7.22 (dd, J = 8.3, 2.0 Hz, 1H), 7.21 (s, 1H), 5.45 (s, 2H), 3.72-3.63 (m, 4H), 3.13 (t, J = 6.7 Hz, 2H), 2.51-2.39 (m, 6H), 1.85-1.70 (m, 2H). |
| 27 | 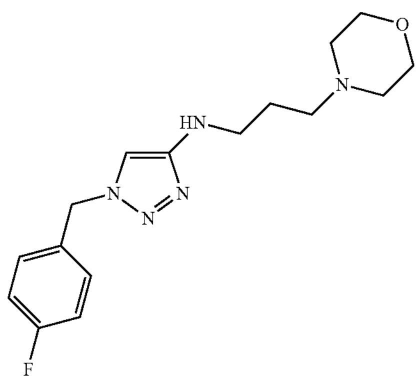 [SMILES: Fc1ccc(Cn2cc(NCCCN3CCOCC3)nn2)cc1] | 1-(4-fluorobenzyl)-N-(3-morpholinopropyl)-1H-1,2,3-triazol-4-amine | $^1$H NMR (CDCl$_3$) δ ppm: 7.26-7.21 (m, 2H), 7.05 (t, J = 8.6 Hz, 2H), 6.71 (s, 1H), 5.37 (s, 2H), 3.77 (t, J = 4.7 Hz, 4H), 3.16 (t, J = 6.4 Hz, 2H), 2.58 (s, 6H), 1.84 (p, J = 6.6 Hz, 2H). |
| 28 | 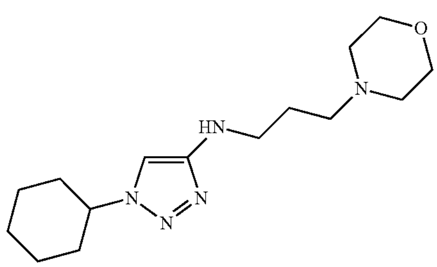 [SMILES: c1c(NCCCN2CCOCC2)nnn1C1CCCCC1] | 1-cyclohexyl-N-(3-morpholinopropyl)-1H-1,2,3-triazol-4-amine | $^1$H NMR (CD$_3$OD) δ ppm: 7.24 (s, 1H), 4.33 (tt, J = 11.7, 3.9 Hz, 1H), 3.76-3.64 (m, 4H), 3.15 (t, J = 6.7 Hz, 2H), 2.60-2.47 (m, 6H), 2.16-2.04 (m, 2H), 1.96-1.86 (m, 2H), 1.86-1.69 (m, 5H), 1.49 (qt, J = 12.9, 3.4 Hz, 2H), 1.32 (qt, J = 12.9, 3.6 Hz, 1H). |
| 29 | 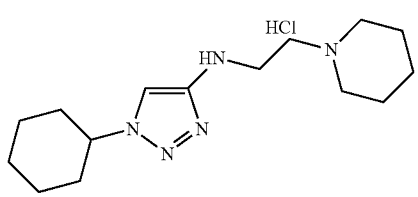 [SMILES: c1c(NCCN2CCCCC2)nnn1C1CCCCC1 ; Cl] | 1-cyclohexyl-N-(2-(piperidin-1-yl)ethyl)-1H-1,2,3-triazol-4-amine hydrochloride | $^1$H NMR (CD$_3$OD) δ ppm: 7.72 (s, 1H), 4.47 (tt, J = 11.6, 3.9 Hz, 1H), 3.65-3.62 (m, 2H), 3.60 (t, J = 6.1 Hz, 2H), 3.34 (t, J = 6.1 Hz, 2H), 3.02 (td, J = 12.5, 3.5 Hz, 2H), 2.18 (dd, J = 12.4, 3.9 Hz, 2H), 2.02-1.72 (m, 10H), 1.52 (qt, J = 12.9, 3.4 Hz, 3H), 1.34 (qt, J = 12.9, 3.7 Hz, 1H). |

| Ex. | Structure | Chem. name | 1 H NMR |
|---|---|---|---|
| 30 | 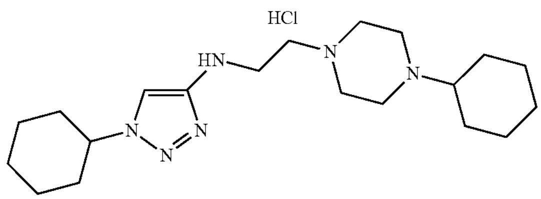 [SMILES: Cl ; c1c(NCCN2CCN(C3CCCCC3)CC2)nnn1C1CCCCC1] | 1-cyclohexyl-N-(2-(4-cyclohexylpiperazin-1-yl)ethyl)-1H-1,2,3-triazol-4-amine hydrochloride | $^1$H NMR (CD$_3$OD) δ ppm: 7.47 (s, 1H), 4.40 (tt, J = 11.6, 3.9 Hz, 1H), 3.87-3.40 (m, 8H), 3.51 (t, J = 5.8 Hz, 2H), 3.30-3.28 (m, 1H), 3.26 (t, J = 5.8 Hz, 2H), 2.24-2.08 (m, 4H), 2.01-1.87 (m, 4H), 1.87-1.68 (m, 4H), 1.59-1.16 (m, 8H). |
| 31 | 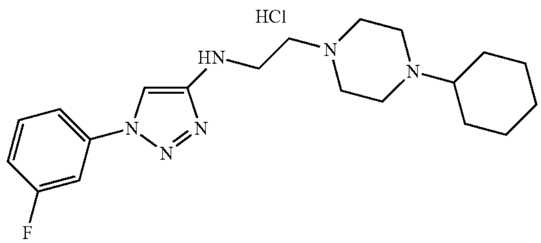 [SMILES: Cl ; Fc1cccc(-n2cc(NCCN3CCN(C4CCCCC4)CC3)nn2)c1] | N-(2-(4-cyclohexylpiperazin-1-yl)ethyl)-1-(3-fluorophenyl)-1H-1,2,3-triazol-4-amine hydrochloride | $^1$H NMR (CD$_3$OD) δ ppm: 7.93 (s, 1H), 7.69-7.63 (m, 2H), 7.58 (td, J = 8.3, 5.9 Hz, 1H), 7.22 (tdd, J = 8.5, 2.3, 1.0 Hz, 1H), 4.00-3.70 (m, 4H), 3.64 (t, J = 5.8 Hz, 2H), 3.61-3.41 (m, 4H), 3.45 (t, J = 5.8 Hz, 2H), 3.38-3.32 (m, 1H), 2.25-2.15 (m, 2H), 2.03-1.92 (m, 2H), 1.77-1.69 (m, 1H), 1.59-1.34 (m, 4H), 1.24 (qt, J = 13.2, 3.7 Hz, 1H). |
| 32 | 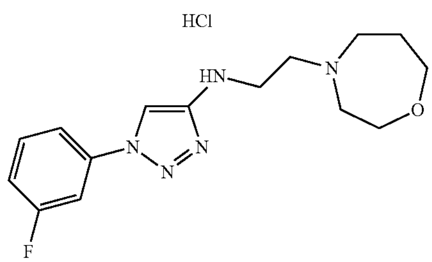 [SMILES: Cl ; Fc1cccc(-n2cc(NCCN3CCCOCC3)nn2)c1] | N-(2-(1,4-oxazepan-4-yl)ethyl)-1-(3-fluorophenyl)-1H-1,2,3-triazol-4-amine hydrochloride | $^1$H NMR (CD$_3$OD) δ ppm: 7.92 (s, 1H), 7.71-7.61 (m, 2H), 7.58 (td, J = 8.3, 5.9 Hz, 1H), 7.22 (tdd, J = 8.6, 2.5, 1.0 Hz, 1H), 3.98-3.93 (m, 2H), 3.93-3.78 (m, 2H), 3.77-3.65 (m, 2H), 3.65 (t, J = 5.6 Hz, 2H), 3.53 (t, J = 5.6 Hz, 2H), 3.54-3.36 (m, 2H), 2.35-2.07 (m, 2H). |
| 33 | 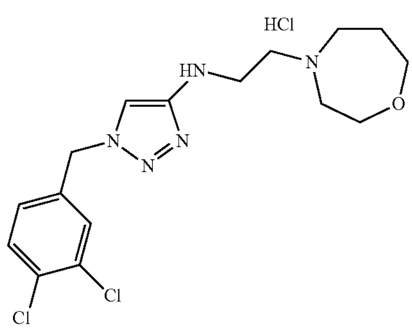 [SMILES: Cl ; Clc1ccc(Cn2cc(NCCN3CCCOCC3)nn2)cc1Cl] | N-(2-(1,4-oxazepan-4-yl)ethyl)-1-(3,4-dichlorobenzyl)-1H-1,2,3-triazol-4-amine hydrochloride | $^1$H NMR (CD$_3$OD) δ ppm: 7.55 (d, J = 8.3 Hz, 1H), 7.53 (d, J = 2.1 Hz, 1H), 7.47 (s, 1H), 7.29 (dd, J = 8.3, 2.2 Hz, 1H), 5.51 (s, 2H), 3.97-3.89 (m, 2H), 3.89-3.78 (m, 2H), 3.69-3.60 (m, 2H), 3.58 (t, J = 6.2 Hz, 2H), 3.46 (t, J = 6.2 Hz, 2H), 3.42-3.34 (m, 2H), 2.30-2.09 (m, 2H). |
| 34 | 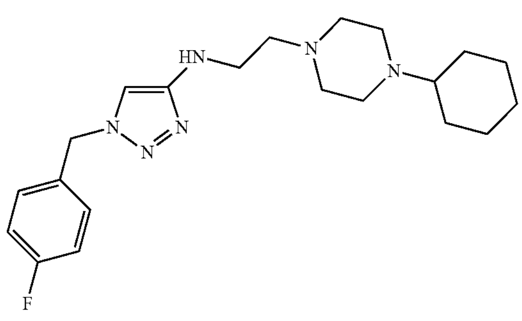 [SMILES: Fc1ccc(Cn2cc(NCCN3CCN(C4CCCCC4)CC3)nn2)cc1] | N-(2-(4-cyclohexylpiperazin-1-yl)ethyl)-1-(4-fluorobenzyl)-1H-1,2,3-triazol-4-amine | $^1$H NMR (CD$_3$OD) δ ppm: 7.35 (dd, J = 8.5, 5.3 Hz, 2H), 7.18 (s, 1H), 7.10 (t, J = 8.7 Hz, 2H), 5.43 (s, 2H), 3.20 (t, J = 6.5 Hz, 2H), 2.72-2.62 (m, 4H), 2.61-2.46 (m, 4H), 2.57 (t, J = 6.5 Hz, 2H), 2.34-2.22 (m, 1H), 2.00-1.90 (m, 2H), 1.87-1.76 (m, 2H), 1.71-1.60 (m, 1H), 1.43-1.08 (m, 5H). |
| 35 | 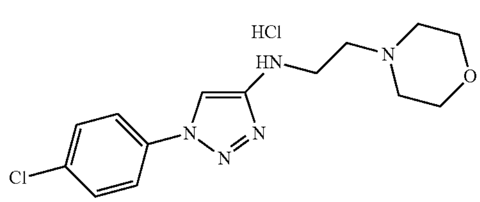 [SMILES: Clc1ccc(-n2cc(NCCN3CCOCC3)nn2)cc1 ; Cl] | 1-(4-chlorophenyl)-N-(2-morpholinoethyl)-1H-1,2,3-triazol-4-amine hydrochloride | $^1$H NMR (CD$_3$OD) δ ppm: 7.87 (s, 1H), 7.82 (d, J = 8.9 Hz, 2H), 7.57 (d, J = 8.8 Hz, 2H), 4.14-4.00 (m, 2H), 3.93-3.78 (m, 2H), 3.66 (t, J = 5.8 Hz, 2H), 3.67-3.55 (m, 2H), 3.47 (t, J = 5.8 Hz, 2H), 3.30-3.17 (m, 2H). |

-continued

| Ex. | Structure | Chem. name | 1 H NMR |
|---|---|---|---|
| 36 | 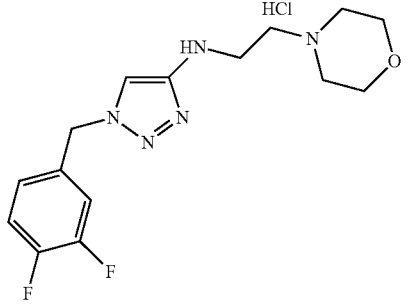 [SMILES: Cl ; Fc1ccc(Cn2cc(NCCN3CCOCC3)nn2)cc1F] | 1-(3,4-difluorobenzyl)-N-(2-morpholinoethyl)-1H-1,2,3-triazol-4-amine hydrochloride | $^1$H NMR (CD$_3$OD) δ ppm: 7.67 (s, 1H), 7.42-7.19 (m, 3H), 5.57 (s, 2H), 4.12-3.76 (m, 4H), 3.62 (t, J = 6.0 Hz, 2H), 3.60-3.48 (m, 2H), 3.41 (t, J = 6.0 Hz, 2H), 3.30-3.15 (m, 2H). |
| 37 | 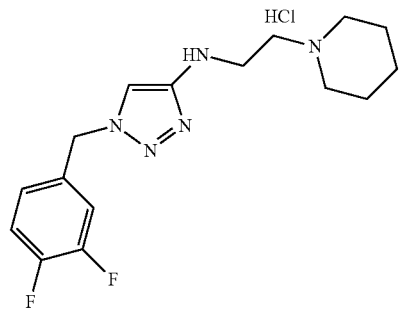 [SMILES: Cl ; Fc1ccc(Cn2cc(NCCN3CCCCC3)nn2)cc1F] | 1-(3,4-difluorobenzyl)-N-(2-(piperidin-1-yl)ethyl)-1H-1,2,3-triazol-4-amine hydrochloride | $^1$H NMR (CD$_3$OD) δ ppm: 7.43 (s, 1H), 7.36-7.11 (m, 3H), 5.50 (s, 2H), 3.68-3.50 (m, 4H), 3.36-3.29 (m, 2H), 3.00 (td, J = 11.9, 3.0 Hz, 2H), 2.04-1.70 (m, 5H), 1.66-1.44 (m, 1H). |
| 38 | 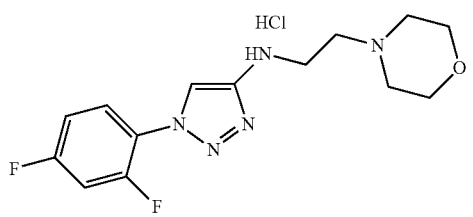 [SMILES: Fc1ccc(-n2cc(NCCN3CCOCC3)nn2)c(F)c1 ; Cl] | 1-(2,4-difluorophenyl)-N-(2-morpholinoethyl)-1H-1,2,3-triazol-4-amine hydrochloride | $^1$H NMR (CD$_3$OD) δ ppm: 7.91-7.76 (m, 1H), 7.70 (s, 1H), 7.40-7.27 (m, 1H), 7.27-7.14 (m, 1H), 4.16-3.98 (m, 2H), 3.94-3.77 (m, 2H), 3.72-3.57 (m, 4H), 3.48 (t, J = 5.1 Hz, 2H), 3.30-3.16 (m, 2H). |
| 39 | 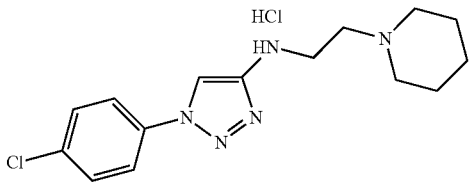 [SMILES: Clc1ccc(-n2cc(NCCN3CCCCC3)nn2)cc1 ; Cl] | 1-(4-chlorophenyl)-N-(2-(piperidin-1-yl)ethyl)-1H-1,2,3-triazol-4-amine hydrochloride | $^1$H NMR (CD$_3$OD) δ ppm: 7.90 (s, 1H), 7.83 (d, J = 8.7 Hz, 2H), 7.58 (d, J = 8.7 Hz, 2H), 3.68-3.59 (m, 4H), 3.38 (t, J = 6.1 Hz, 2H), 3.04 (td, J = 11.9, 2.7 Hz, 2H), 2.04-1.72 (m, 5H), 1.66-1.48 (m, 1H). |
| 40 | 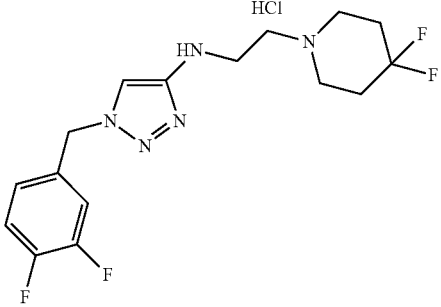 [SMILES: Cl ; Fc1ccc(Cn2cc(NCCN3CCC(F)(F)CC3)nn2)cc1F] | 1-(3,4-difluorobenzyl)-N-(2-(4,4-difluoropiperidin-1-yl)ethyl)-1H-1,2,3-triazol-4-amine hydrochloride | $^1$H NMR (CD$_3$OD) δ ppm: 7.64 (s, 1H), 7.42-7.17 (m, 3H), 5.56 (s, 2H), 3.62 (t, J = 5.9 Hz, 2H), 3.73-3.38 (m, 4H), 3.45 (t, J = 5.9 Hz, 2H), 2.60-2.23 (m, 4H). |

| Ex. | Structure | Chem. name | 1 H NMR |
|---|---|---|---|
| 41 | 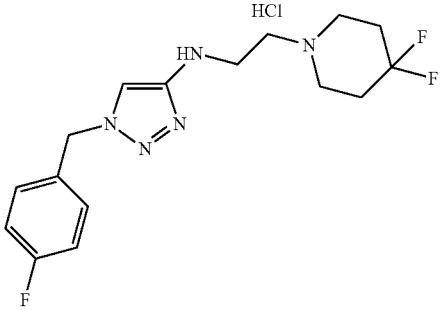 [SMILES: Cl ; Fc1ccc(Cn2cc(NCCN3CCC(F)(F)CC3)nn2)cc1] | N-(2-(4,4-difluoropiperidin-1-yl)ethyl)-1-(4-fluorobenzyl)-1H-1,2,3-triazol-4-amine hydrochloride | $^1$H NMR (CD$_3$OD) δ ppm: 7.62 (s, 1H), 7.45 (dd, J = 8.5, 5.4 Hz, 2H), 7.14 (t, J = 8.8 Hz, 2H), 5.55 (s, 2H), 3.61 (t, J = 5.9 Hz, 2H), 3.71-3.40 (m, 4H), 3.44 (t, J = 5.9 Hz, 2H), 2.53-2.30 (m, 4H). |
| 42 | 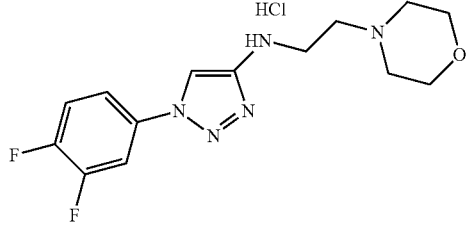 [SMILES: Fc1ccc(-n2cc(NCCN3CCOCC3)nn2)cc1F ; Cl] | 1-(3,4-difluorophenyl)-N-(2-morpholinoethyl)-1H-1,2,3-triazol-4-amine hydrochloride | $^1$H NMR (CD$_3$OD) δ ppm: 7.89 (s, 1H), 7.84 (ddd, J = 11.3, 6.9, 2.7 Hz, 1H), 7.70-7.62 (m, 1H), 7.49 (dt, J = 10.1, 8.7 Hz, 1H), 4.07 (d, J = 13.0 Hz, 2H), 3.84 (t, J = 12.5 Hz, 2H), 3.66 (t, J = 5.9 Hz, 2H), 3.61 (d, J = 12.7 Hz, 2H), 3.46 (t, J = 5.9 Hz, 2H), 3.25 (t, J = 11.6 Hz, 2H). |
| 43 | 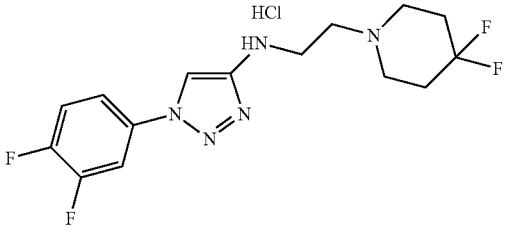 [SMILES: Fc1ccc(-n2cc(NCCN3CCC(F)(F)CC3)nn2)cc1F ; Cl] | 1-(3,4-difluorophenyl)-N-(2-(4,4-difluoropiperidin-1-yl)ethyl)-1H-1,2,3-triazol-4-amine hydrochloride | $^1$H NMR (CD$_3$OD) δ ppm: 7.89 (s, 1H), 7.84 (ddd, J = 11.3, 6.9, 2.7 Hz, 1H), 7.71-7.63 (m, 1H), 7.49 (dt, J = 10.1, 8.7 Hz, 1H), 3.88-3.73 (m, 2H), 3.66 (t, J = 5.8 Hz, 2H), 3.51 (t, J = 5.8 Hz, 2H), 3.43-3.34 (m, 2H), 2.50-2.32 (m, 4H). |
| 44 | 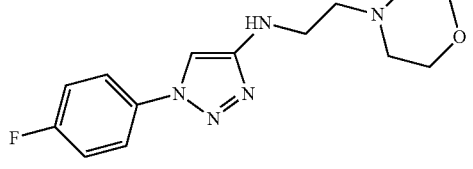 | 1-(4-fluorophenyl)-N-(2-morpholinoethyl)-1H-1,2,3-triazol-4-amine hydrochloride | $^1$H NMR (CD$_3$OD) δ ppm: 7.88 (s, 1H), 7.84 (dd, J = 9.2, 4.7 Hz, 2H), 7.32 (t, J = 8.7 Hz, 2H), 4.08 (d, J = 13.1 Hz, 2H), 3.86 (t, J = 12.5 Hz, 2H), 3.67 (t, J = 5.9 Hz, 2H), 3.63 (d, J = 12.9 Hz, 2H), 3.47 (t, J = 5.9 Hz, 2H), 3.26 (t, J = 11.9 Hz, 2H). |
| 45 | 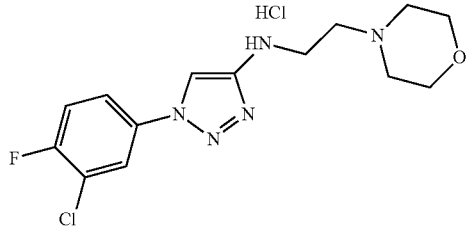 [SMILES: Fc1ccc(-n2cc(NCCN3CCOCC3)nn2)cc1Cl ; Cl] | 1-(3-chloro-4-fluorophenyl)-N-(2-morpholinoethyl)-1H-1,2,3-triazol-4-amine hydrochloride | $^1$H NMR (CD$_3$OD) δ ppm: 8.02 (dd, J = 6.3, 2.7 Hz, 1H), 7.90 (s, 1H), 7.82 (ddd, J = 9.0, 3.9, 2.7 Hz, 1H), 7.47 (t, J = 8.9 Hz, 1H), 4.08 (d, J = 13.0 Hz, 2H), 3.84 (t, J = 12.5 Hz, 2H), 3.66 (t, J = 5.9 Hz, 2H), 3.62 (d, J = 12.9 Hz, 2H), 3.47 (t, J = 5.9 Hz, 2H), 3.26 (td, J = 13.1, 12.5, 3.4 Hz, 2H). |
| 46 | 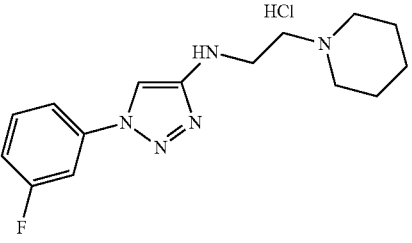 [SMILES: Cl ; Fc1cccc(-n2cc(NCCN3CCCCC3)nn2)c1] | 1-(3-fluorophenyl)-N-(2-(piperidin-1-yl)ethyl)-1H-1,2,3-triazol-4-amine hydrochloride | $^1$H NMR (CD$_3$OD) δ ppm: 7.93 (s, 1H), 7.72-7.50 (m, 3H), 7.23 (td, J = 8.3, 2.6 Hz, 1H), 3.73-3.58 (m, 4H), 3.39 (t, J = 6.1 Hz, 2H), 3.04 (td, J = 12.3, 3.3 Hz, 2H), 2.08-1.72 (m, 5H), 1.58 (t, J = 12.7 Hz, 1H). |

| Ex. | Structure | Chem. name | 1 H NMR |
|---|---|---|---|
| 47 | 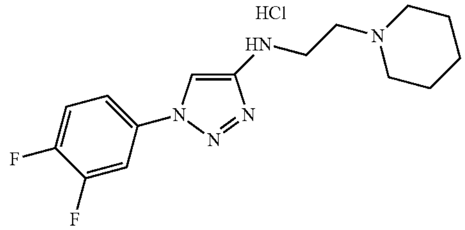 [SMILES: Fc1ccc(-n2cc(NCCN3CCCCC3)nn2)cc1F ; Cl] | 1-(3,4-difluorophenyl)-N-(2-(piperidin-1-yl)ethyl)-1H-1,2,3-triazol-4-amine hydrochloride | $^1$H NMR (CD$_3$OD) δ ppm: 7.93 (s, 1H), 7.86 (ddd, J = 11.2, 6.9, 2.7 Hz, 1H), 7.74-7.62 (m, 1H), 7.50 (dt, J = 10.1, 8.6 Hz, 1H), 3.72-3.58 (m, 4H), 3.39 (t, J = 6.0 Hz, 2H), 3.04 (td, J = 12.3, 3.5 Hz, 2H), 2.05-1.74 (m, 5H), 1.65-1.48 (m, 1H). |
| 48 | 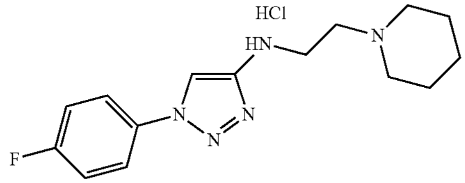 [SMILES: Fc1ccc(-n2cc(NCCN3CCCCC3)nn2)cc1 ; Cl] | 1-(4-fluorophenyl)-N-(2-(piperidin-1-yl)ethyl)-1H-1,2,3-triazol-4-amine hydrochloride | $^1$H NMR (DMSO) δ ppm: 10.36 (s, 1H), 8.13 (s, 1H), 7.89 (dd, J = 9.1, 4.8 Hz, 2H), 7.43 (t, J = 8.8 Hz, 2H), 3.60-3.37 (m, 4H), 3.28-3.14 (m, 2H), 3.05-2.80 (m, 2H), 1.99-1.58 (m, 5H), 1.52-1.22 (m, 1H). |
| 49 | 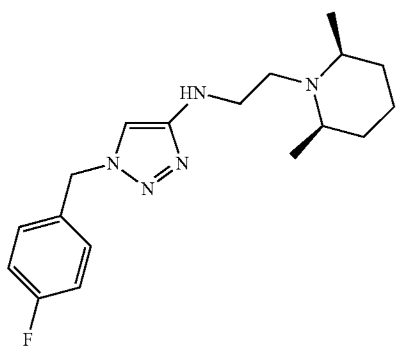 [SMILES: C[C@@H]1CCC[C@H](C)N1CCNc1cn(Cc2ccc(F)cc2)nn1] | N-(2-((2RS*,6SR*)-2,6-dimethylpiperidin-1-yl)ethyl)-1-(4-fluorobenzyl)-1H-1,2,3-triazol-4-amine | $^1$H NMR (CD$_3$OD) δ ppm: 7.34 (dd, J = 8.5, 5.4 Hz, 2H), 7.16 (s, 1H), 7.10 (t, J = 8.7 Hz, 2H), 5.43 (s, 2H), 3.19 (dd, J = 8.7, 6.6 Hz, 2H), 2.90 (dd, J = 8.7, 6.6 Hz, 2H), 2.68-2.49 (m, 2H), 1.77-1.17 (m, 6H), 1.13 (d, J = 6.3 Hz, 6H). |
| 50 | 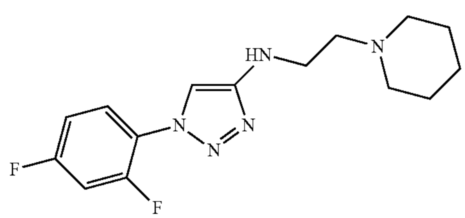 [SMILES: Fc1ccc(-n2cc(NCCN3CCCCC3)nn2)c(F)c1] | 1-(2,4-difluorophenyl)-N-(2-(piperidin-1-yl)ethyl)-1H-1,2,3-triazol-4-amine | $^1$H NMR (CDCl$_3$) δ ppm: 7.95-7.81 (m, 1H), 7.35 (d, J = 3.0 Hz, 1H), 7.10-6.94 (m, 2H), 5.01-4.77 (m, 1H), 3.58-3.29 (m, 2H), 2.87-2.74 (m, 2H), 2.73-2.44 (m, 4H), 1.91-1.62 (m, 5H), 1.60-1.37 (m, 1H). |
| 51 | 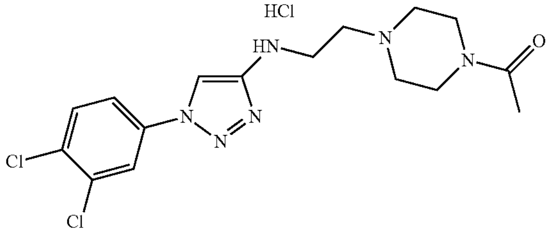 [SMILES: CC(=O)N1CCN(CCNc2cn(-c3ccc(Cl)c(Cl)c3)nn2)CC1 ; Cl] | 1-(4-(2-(1-(3,4-dichlorophenyl)-1H-1,2,3-triazol-4-ylamino)ethyl)piperazin-1-yl)ethanone hydrochloride | $^1$H NMR (CD$_3$OD) δ ppm: 8.07 (d, J = 2.5 Hz, 1H), 7.93 (s, 1H), 7.81 (dd, J = 8.8, 2.5 Hz, 1H), 7.73 (d, J = 8.7 Hz, 1H), 4.76-4.50 (m, 1H), 4.31-4.00 (m, 1H), 3.82-3.58 (m, 2H), 3.67 (t, J = 5.8 Hz, 2H), 3.49 (t, J = 5.8 Hz, 2H), 3.30-3.00 (m, 4H), 2.16 (s, 3H). |

Preparation of Compounds of Formula (Ib)

Example 52

Synthesis of N-(1-(1-adamantyl)-1H-1,2,3-triazol-4-yl)-N-(2-morpholinoethyl)cyclopropanecarboxamide hydrochloride

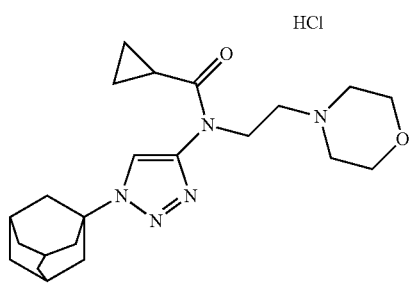 [SMILES: Cl ; O=C(C1CC1)N(CCN1CCOCC1)c1cn(C23CC4CC(CC(C4)C2)C3)nn1]

To a stirred solution of 1-(1-adamantyl)-N-(2-morpholinoethyl)-1H-1,2,3-triazol-4-amine (base of example 6) (100 mg, 0.302 mmol) in dry $CH_2Cl_2$ (8 mL) was added DIPEA (77.5 µL, 0.453 mmol) under an argon atmosphere. After 10 min. stirring at r.t., the reaction mixture was cooled down to 0° C. and cyclopropanecarbonyl chloride (30.1 µL, 0.332 mmol) was added, after which the reaction solution was allowed to reach r.t. and stirred overnight. The reaction mixture was then diluted with $CH_2Cl_2$, washed with 3% aq. HCl (three times), saturated aq. $NaHCO_3$ (three times) and finally with saturated aq. NaCl. The combined organic fractions were dried over $MgSO_4$ and the solvent removed under reduced pressure after filtration to afford N-(1-(1-adamantyl)-1H-1,2,3-triazol-4-yl)-N-(2-morpholinoethyl)cyclopropanecarboxamide (101 mg, 83%) as a colourless oil. The compound was prepared as hydrochloride salt following the method described in example 1. $^1$H NMR ($CD_3OD$) δ ppm: 8.33 (s, 1H), 4.15-4.03 (m, 4H), 3.81 (t, J=12.5 Hz, 2H), 3.66 (d, J=12.4 Hz, 2H), 3.43 (t, J=6.0 Hz, 2H), 3.21 (t, J=11.0 Hz, 2H), 2.37-2.23 (m, 9H), 1.92-1.78 (m, 6H), 1.54-1.44 (m, 1H), 1.04-0.96 (m, 2H), 0.87-0.74 (m, 2H).

Examples (53-55) were prepared following the above described method:

| Ex. | Structure | Chem. name | 1 H NMR |
| --- | --- | --- | --- |
| 53 | 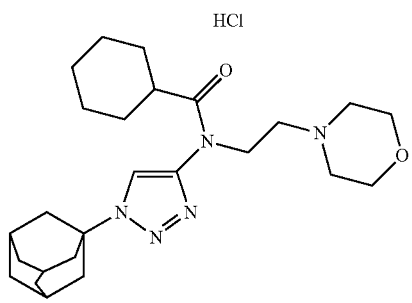 [SMILES: Cl ; O=C(C1CCCCC1)N(CCN1CCOCC1)c1cn(C23CC4CC(CC(C4)C2)C3)nn1] | N-(1-(1-adamantyl)-1H-1,2,3-triazol-4-yl)-N-(2-morpholino-ethyl)cyclohexanecarboxamide hydrochloride | $^1$H NMR ($CD_3OD$) δ ppm: 8.37 (s, 1H), 4.04 (t, J = 6.4 Hz, 2H), 4.09-3.74 (m, 4H), 3.65-3.16 (m, 4H), 3.38 (t, J = 6.3 Hz, 2H), 2.18 (tt, J = 11.8, 3.2 Hz, 1H), 1.96-1.82 (m, 9H), 1.82-1.57 (m, 7H), 1.52-1.13 (m, 7H), 1.12-0.97 (m, 2H). |
| 54 | 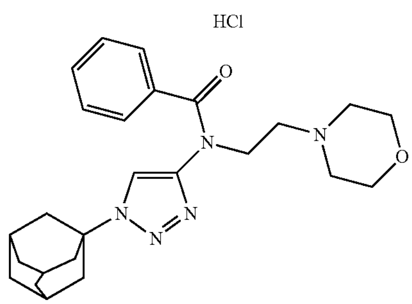 [SMILES: Cl ; O=C(c1ccccc1)N(CCN1CCOCC1)c1cn(C23CC4CC(CC(C4)C2)C3)nn1] | N-(1-(1-adamantyl)-1H-1,2,3-triazol-4-yl)-N-(2-morpholino-ethyl)benzamide hydrochloride | $^1$H NMR ($CD_3OD$) δ ppm: 8.21-7.94 (m, 1H), 7.62-7.21 (m, 5H), 4.42-4.26 (m, 2H), 4.17-4.03 (m, 2H), 3.95-3.80 (m, 2H), 3.80-3.66 (m, 2H), 3.62-3.50 (m, 2H), 3.26-3.11 (m, 2H), 2.23-2.12 (m, 3H), 2.11-1.98 (m, 6H), 1.85-1.66 (m, 6H). |
| 55 | 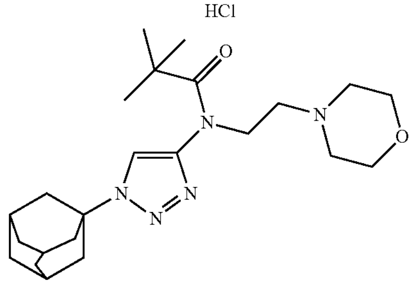 [SMILES: Cl ; CC(C)(C)C(=O)N(CCN1CCOCC1)c1cn(C23CC4CC(CC(C4)C2)C3)nn1] | N-(1-(1-adamantyl)-1H-1,2,3-triazol-4-yl)-N-(2-morpholino-ethyl)pivalamide hydrochloride | $^1$H NMR ($CD_3OD$) δ ppm: 8.35 (s, 1H), 4.08 (d, J = 11.5 Hz, 2H), 3.96 (t, J = 6.5 Hz, 2H), 3.78 (t, J = 11.5 Hz, 2H), 3.60 (d, J = 8.1 Hz, 2H), 3.38 (t, J = 6.5 Hz, 2H), 3.27-3.13 (m, 2H), 2.33-2.25 (m, 9H), 1.96-1.78 (m, 6H), 1.04 (s, 9H). |

Example 56

Synthesis of N-(1-(3,4-dichlorobenzyl)-1H-1,2,3-triazol-4-yl)-N-(2-morpholinoethyl)acetamide hydrochloride

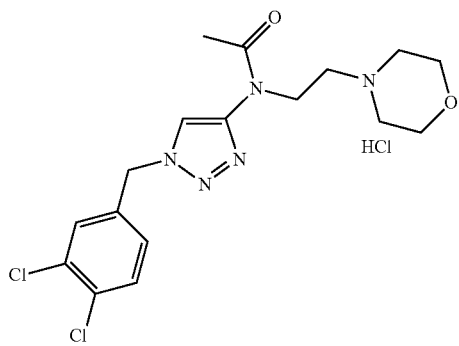 [SMILES: CC(=O)N(CCN1CCOCC1)c1cn(Cc2ccc(Cl)c(Cl)c2)nn1 ; Cl]

A mixture of 1-(3,4-dichlorobenzyl)-N-(2-morpholinoethyl)-1H-1,2,3-triazol-4-amine (base of example 7) (70 mg, 0.196 mmol) and acetic anhydride (0.5 mL, excess) was heated using microwave heating at 120° C. for 10 min. After cooling back to r.t., the reaction mixture was quenched with H$_2$O and extracted with AcOEt twice. The combined organic fractions were dried over sodium sulphate and the solvent removed under reduced pressure to give N-(1-(3,4-dichlorobenzyl)-1H-1,2,3-triazol-4-yl)-N-(2-morpholinoethyl)acetamide as a colourless oil (60 mg, 76%). The compound was prepared as hydrochloride salt following the method described in example 1. $^1$H NMR (CD$_3$OD) δ ppm: 8.26 (s, 1H), 7.60 (d, J=2.0 Hz, 1H), 7.57 (d, J=8.3 Hz, 1H), 7.34 (dd, J=8.4, 2.1 Hz, 1H), 5.64 (s, 2H), 4.14-4.08 (m, 2H), 4.07 (t, J=5.7 Hz, 2H), 3.82 (t, J=12.5 Hz, 2H), 3.68 (d, J=12.4 Hz, 2H), 3.43 (t, J=5.8 Hz, 2H), 3.20 (t, J=12.1 Hz, 2H), 1.98 (s, 3H).

Examples 57-58 were prepared following the method of example 56:

| Ex. | Structure | Chem. name | 1 H NMR |
|---|---|---|---|
| 57 | HCl (structure) | N-(1-(1-adamantyl)-1H-1,2,3-triazol-4-yl)-N-(2-morpholinoethyl)acetamide hydrochloride | $^1$H NMR (CD$_3$OD) δ ppm: 8.33 (s, 1H), 4.14-4.03 (m, 4H), 3.85 (td, J = 13.5, 12.7, 2.1 Hz, 2H), 3.71 (dd, J = 12.3, 1.8 Hz, 2H), 3.44 (t, J = 5.8 Hz, 2H), 3.22 (td, J = 12.2, 3.6 Hz, 2H), 2.35-2.24 (m, 9H), 1.98 (s, 3H), 1.92-1.80 (m, 6H). |
| 58 | HCl (structure) | N-(1-(3,4-dichlorophenyl)-1H-1,2,3-triazol-4-yl)-N-(2-morpholinoethyl)acetamide hydrochloride | $^1$H NMR (CD$_3$OD) δ ppm: 8.83 (s, 1H), 8.19 (d, J = 2.5 Hz, 1H), 7.91 (dd, J = 8.8, 2.5 Hz, 1H), 7.80 (d, J = 8.7 Hz, 1H), 4.16 (t, J = 5.7 Hz, 2H), 4.11 (d, J = 12.7 Hz, 2H), 3.85 (t, J = 11.7 Hz, 2H), 3.73 (d, J = 11.9 Hz, 2H), 3.49 (t, J = 5.6 Hz, 2H), 3.29-3.15 (m, 2H), 2.09 (s, 3H). |

Preparation of Compounds of Formula (Ic)

Example 59

Synthesis of N-(1-(3,4-dichlorophenyl)-1H-1,2,3-triazol-4-yl)-N-(2-morpholinoethyl)methanesulfonamide hydrochloride

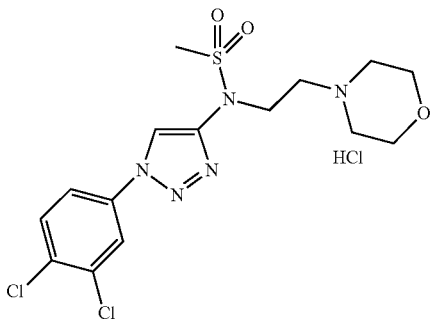 [SMILES: CS(=O)(=O)N(CCN1CCOCC1)c1cn(-c2ccc(Cl)c(Cl)c2)nn1 ; Cl]

To a stirred solution of 1-(3,4-dichlorophenyl)-N-(2-morpholinoethyl)-1H-1,2,3-triazol-4-amine (base of example 5) (100 mg, 0.292 mmol) in dry CH$_2$Cl$_2$ (10 mL), DIPEA (110 µL, 0.643 mmol) was added under an argon atmosphere and the reaction mixture stirred for 10 min. at r.t. The mixture was cooled down to 0° C. and methanesulfonyl chloride (24.9 µL, 0.321 mmol) was added dropwise. The reaction mixture stirred overnight at r.t., after which one additional equivalent of reactants was added. The reaction was stirred at r.t. until full conversion was reached and the resulting mixture was diluted with CH$_2$Cl$_2$, washed with 3% aq. HCl (three times) and with saturated aq. NaHCO$_3$ (three times) followed by saturated aq. NaCl. The combined organic fractions were dried over MgSO$_4$ and the solvent removed under reduced pressure to give N-(1-(3,4-dichlorophenyl)-1H-1,2,3-triazol-4-yl)-N-(2-morpholinoethyl)methanesulfonamide (102 mg, 83%) as a yellow solid. $^1$H NMR (CD$_3$OD) δ ppm: 8.51 (s, 1H), 8.07 (d, J=2.1 Hz, 1H), 7.78 (dd, J=8.5, 2.1 Hz, 1H), 7.67 (d, J=8.5 Hz, 1H), 3.91 (t, J=6.2 Hz, 2H), 3.65-3.50 (m, 4H), 3.08 (s, 3H), 2.67-2.54 (m, 2H), 2.54-2.39 (m, 4H).

Example 60 was prepared following the above described method

Preparation of Compound of Formula (Id)

Example 61

Synthesis of 1-(3,4-dichlorophenyl)-N-(2-morpholinoethyl)-N-propyl-1H-1,2,3-triazol-4-amine hydrochloride

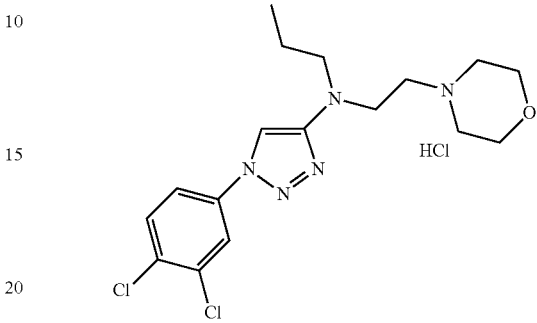

To a solution of 1-(3,4-dichlorophenyl)-N-(2-morpholinoethyl)-1H-1,2,3-triazol-4-amine (base of example 5) (85 mg, 0.248 mmol) in DCE (2.5 mL) in a microwave vial under argon atmosphere, propionaldehyde (49 µL, 0.671 mmol) was added followed by NaBH(OAc)$_3$ (105.2 mg, 0.487). The reaction mixture was heated under microwave radiation at 120° C. for 10 min. After cooling back to r.t., the reaction mixture was quenched with saturated aq. NaHCO$_3$ and extracted with CH$_2$Cl$_2$ twice. The combined organic fractions were washed with saturated aq. NaCl and dried over MgSO$_4$. The solvent was removed under reduced pressure after filtration. The residue was purified by Combiflash chromatography (SiO$_2$, c-Hexane/AcOEt up to 100%) to give 1-(3,4-dichlorophenyl)-N-(2-morpholinoethyl)-N-propyl-1H-1,2,3-triazol-4-amine (60.8 mg, 63%) as a red oil. The compound was prepared as hydrochloride salt following the method described in example 1. $^1$H NMR (CD$_3$OD) δ ppm: 8.11 (d, J=2.5 Hz, 1H), 8.04 (s, 1H), 7.84 (dd, J=8.8, 2.5 Hz, 1H), 7.73 (d, J=8.8 Hz, 1H), 4.09 (d, J=12.9 Hz, 2H), 3.90-3.83 (m, 2H), 3.81 (t, J=6.3 Hz, 2H), 3.67 (d, J=12.5 Hz, 2H), 3.47 (t, J=6.3 Hz, 2H), 3.30-3.19 (m, 4H), 1.68 (h, J=7.4 Hz, 2H), 0.99 (t, J=7.4 Hz, 3H).

Examples (62-67) were prepared following the above described method:

| Ex. | Structure | Chem. name | 1 H NMR |
|---|---|---|---|
| 60 | (structure shown: 4-chlorobenzenesulfonamide derivative with HCl) | 4-chloro-N-(1-(3,4-dichlorophenyl)-1H-1,2,3-triazol-4-yl)-N-(2-morpholinoethyl)benzenesulfonamide hydrochloride | $^1$H NMR (CD$_3$OD) δ ppm: 8.77 (s, 1H), 8.19 (d, J = 2.6 Hz, 1H), 7.90 (dd, J = 8.8, 2.6 Hz, 1H), 7.79 (d, J = 8.7 Hz, 1H), 7.80 (d, J = 8.7 Hz, 2H), 7.63 (d, J = 8.6 Hz, 2H), 4.22 (t, J = 6.0 Hz, 2H), 4.16-3.98 (m, 2H), 3.98-3.79 (m, 2H), 3.74-3.53 (m, 2H), 3.46 (t, J = 6.0 Hz, 2H), 3.31-3.20 (m, 2H). |

| Ex. | Structure | Chem. name | 1 H NMR |
|---|---|---|---|
| 62 | 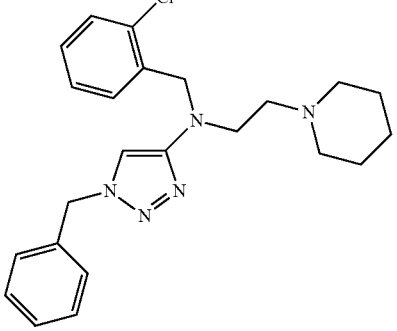 | 1-benzyl-N-(2-chlorobenzyl)-N-(2-(piperidin-1-yl)ethyl)-1H-1,2,3-triazol-4-amine | $^1$H NMR (CDCl$_3$) δ ppm: 7.39-7.27 (m, 5H), 7.25-7.19 (m, 2H), 7.19-7.10 (m, 2H), 6.56 (s, 1H), 5.36 (s, 2H), 4.54 (s, 2H), 3.52 (t, J = 7.2 Hz, 2H), 2.52 (t, J = 7.2 Hz, 2H), 2.37 (t, J = 5.1 Hz, 4H), 1.60-1.45 (m, 4H), 1.45-1.33 (m, 2H). |
| 63 | 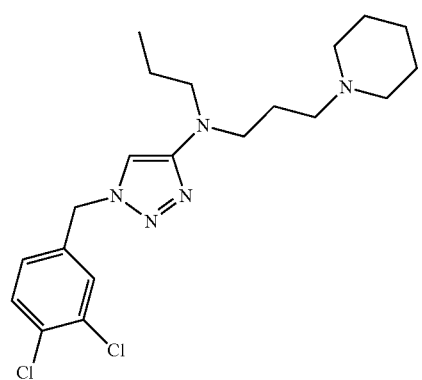 [SMILES: CCCN(CCCN1CCCCC1)c1cn(Cc2ccc(Cl)c(Cl)c2)nn1] | 1-(3,4-dichlorobenzyl)-N-(3-(piperidin-1-yl)propyl)-N-propyl-1H-1,2,3-triazol-4-amine | $^1$H NMR (CDCl$_3$) δ ppm: 7.43 (d, J = 8.2 Hz, 1H), 7.36 (d, J = 2.2 Hz, 1H), 7.09 (dd, J = 8.3, 2.1 Hz, 1H), 6.65 (s, 1H), 5.34 (s, 2H), 3.24 (t, J = 7.2 Hz, 2H), 3.20-3.09 (m, 2H), 2.40 (dd, J = 17.2, 9.3 Hz, 6H), 2.35-1.92 (m, 2H), 1.79 (p, J = 7.4 Hz, 2H), 1.68-1.51 (m, 6H), 1.50-1.36 (m, 2H), 0.89 (t, J = 7.4 Hz, 3H). |
| 64 | 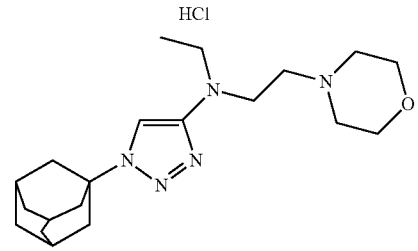 [SMILES: Cl ; CCN(CCN1CCOCC1)c1cn(C23CC4CC(CC(C4)C2)C3)nn1] | 1-(1-adamantyl)-N-ethyl-N-(2-morpholinoethyl)-1H-1,2,3-triazol-4-amine hydrochloride | $^1$H NMR (CD$_3$OD) δ ppm: 7.64 (s, 1H), 4.17-3.76 (m, 4H), 3.68 (t, J = 6.1 Hz, 2H), 3.73-3.45 (m, 2H), 3.42 (t, J = 6.1 Hz, 2H), 3.34 (t, J = 7.1 Hz, 2H), 3.38-3.16 (m, 2H), 2.31-2.22 (m, 9H), 1.92-1.77 (m, 6H), 1.15 (t, J = 7.0 Hz, 3H). |
| 65 | 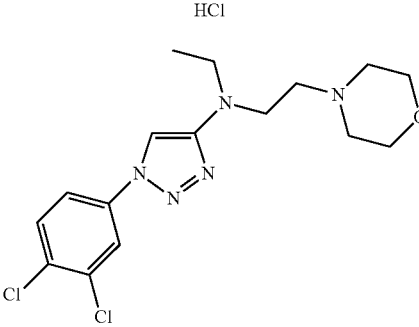 | 1-(3,4-dichlorophenyl)-N-ethyl-N-(2-morpholinoethyl)-1H-1,2,3-triazol-4-amine hydrochloride | $^1$H NMR (CD$_3$OD) δ ppm: 8.10 (d, J = 2.5 Hz, 1H), 8.05 (s, 1H), 7.83 (dd, J = 8.8, 2.6 Hz, 1H), 7.73 (d, J = 8.7 Hz, 1H), 4.09 (d, J = 13.3 Hz, 2H), 3.89-3.82 (m, 2H), 3.78 (t, J = 6.1 Hz, 2H), 3.68 (d, J = 12.6 Hz, 2H), 3.49 (t, J = 6.1 Hz, 2H), 3.40 (q, J = 7.2 Hz, 2H), 3.29-3.19 (m, 2H), 1.21 (t, J = 7.0 Hz, 3H). |
| 66 | 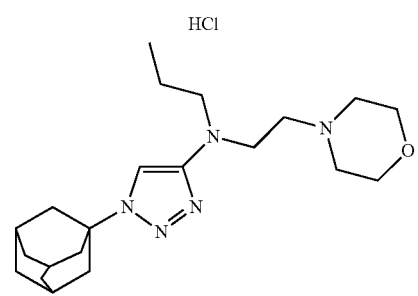 [SMILES: Cl ; CCCN(CCN1CCOCC1)c1cn(C23CC4CC(CC(C4)C2)C3)nn1] | 1-(1-adamantyl)-N-(2-morpholinoethyl)-N-propyl-1H-1,2,3-triazol-4-amine hydrochloride | $^1$H NMR (CD$_3$OD) δ ppm: 7.90 (s, 1H), 4.06-3.88 (m, 4H), 3.76 (t, J = 6.6 Hz, 2H), 3.40 (t, J = 6.6 Hz, 2H), 3.36-3.25 (m, 6H), 2.37-2.19 (m, 9H), 2.00-1.76 (m, 6H), 1.63 (h, J = 7.4 Hz, 2H), 0.97 (t, J = 7.4 Hz, 3H). |

-continued

| Ex. | Structure | Chem. name | 1 H NMR |
|---|---|---|---|
| 67 | (structure shown) | N-(4-chlorobenzyl)-1-(1-adamantyl)-N-(2-morpholinoethyl)-1H-1,2,3-triazol-4-amine hydrochloride | $^1$H NMR (CD$_3$OD) δ ppm: 7.71 (s, 1H), 7.37 (d, J = 8.6 Hz, 2H), 7.31 (d, J = 8.5 Hz, 2H), 4.47 (s, 2H), 4.10-3.79 (m, 4H), 3.71 (t, J = 6.3 Hz, 2H), 3.37 (t, J = 6.4 Hz, 2H), 3.59-3.03 (m, 4H), 2.34-2.15 (m, 9H), 1.93-1.75 (m, 6H). |

Preparation of Compounds of Formula (Ie)

Example 68

Synthesis of 1-(1-(3,4-dichlorophenyl)-1H-1,2,3-triazol-4-yl)-1-(2-morpholinoethyl)-3-propylthiourea hydrochloride

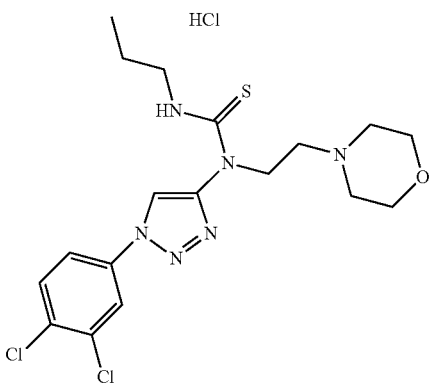 [SMILES: CCCNC(=S)N(CCN1CCOCC1)c1cn(-c2ccc(Cl)c(Cl)c2)nn1 ; Cl]

To a stirred solution of 1-(3,4-dichlorophenyl)-N-(2-morpholinoethyl)-1H-1,2,3-triazol-4-amine (base of example 5) (100 mg, 0.292 mmol, 1 equiv.) in CH$_2$Cl$_2$ (8 mL), TEA (130 μL, 0.936 mmol, 3.2 equiv.) was added and the resulting reaction mixture stirred for 10 min at r.t. The mixture was cooled down to 0° C. and 1-isothiocyanatopropane (79.8 μL, 0.760 mmol, 2.6 equiv.) was added, after which it was allowed to reach room temperature and slowly heated to 50° C. for 16 h. After cooling back to r.t., the resulting mixture was diluted with CH$_2$Cl$_2$, washed with 3% aq. HCl (three times) and with saturated aq. NaHCO$_3$ (three times) followed by saturated aq. NaCl. The combined organic fractions were dried over MgSO$_4$ and the solvent removed under reduced pressure to give 1-(1-(3,4-dichlorophenyl)-1H-1,2,3-triazol-4-yl)-1-(2-morpholinoethyl)-3-propylthiourea as an orange-red oil (83 mg, 64%). The compound was prepared as hydrochloride salt following the method described in example 1. $^1$H NMR (CD$_3$OD) δ ppm: 8.81 (s, 1H), 8.19 (d, J=2.6 Hz, 1H), 7.91 (dd, J=8.7, 2.4 Hz, 1H), 7.81 (d, J=8.7 Hz, 1H), 4.72 (t, J=6.2 Hz, 2H), 4.14-4.05 (m, 2H), 3.88-3.76 (m, 2H), 3.73 (d, J=12.6 Hz, 2H), 3.59-3.49 (m, 4H), 3.32-3.23 (m, 2H), 1.62 (h, J=7.5 Hz, 2H), 0.90 (t, J=7.5 Hz, 3H).

BIOLOGICAL ACTIVITY

Some representative compounds of the invention are tested for their activity as sigma (sigma-1 and sigma-2) inhibitors. The following protocols are followed:

Sigma-1

Brain membrane preparation and binding assays for the sigma1-receptor are performed as described (DeHaven-Hudkins et al., 1992) with some modifications. In brief, guinea pig brains are homogenized in 10 vols. (w/v) of Tris-HCl 50 mM 0.32 M sucrose, pH 7.4, with a Kinematica Polytron PT 3000 at 15000 r.p.m. for 30 s. The homogenate is centrifuged at 1000 g for 10 min at 4 Degrees C and the supernatants collected and centrifuged again at 48000 g for 15 min at 4 Degrees C. The pellet is resuspended in 10 volumes of Tris-HCl buffer (50 mM, pH 7.4), incubated at 37 Degrees C for 30 min, and centrifuged at 48000 g for 20 min at 4 Degrees C. Following this, the pellet is resuspended in fresh Tris-HCl buffer (50 mM, pH 7.4) and stored on ice until use.

Each assay tube contains 10 μL of [$^3$H](+)-pentazocine (final concentration of 0.5 nM), 900 μL of the tissue suspension to a final assay volume of 1 mL and a final tissue concentration of approximately 30 mg tissue net weight/mL. Non-specific binding is defined by addition of a final concentration of 1 μM haloperidol. All tubes are incubated at 37 Degrees C for 150 min before termination of the reaction by rapid filtration over Schleicher and Schuell GF 3362 glass fibre filters [previously soaked in a solution of 0.5 percent polyethylenimine for at least 1 h]. Filters are then washed four times with 4 mL of cold Tris-HCl buffer (50 mM, pH 7.4). Following addition of scintillation cocktail, the samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

Sigma-2

Binding studies for sigma2-receptor are performed as described (et al., 1991) with some modifications. In brief, brains from sigma receptor type I (sigma1) knockout mice are homogenized in a volume of 10 mUg tissue net weight of ice-cold 10 mM Tris-HCl, pH 7.4, containing 320 mM sucrose (Tris-sucrose buffer) with a Potter-Elvehjem homogenizer (10 strokes at 500 r.p.m.) The homogenates are then centrifuged at 1000 g for 10 min at 4 degrees centigrade, and the supernatants are saved. The pellets are resuspended by vortexing in 2 mUg ice-cold Tris-sucrose buffer and centrifuged again at 1000 g for 10 min. The combined 1000 g supernatants are centrifuged at 31000 g for 15 min at 4 Degrees C. The pellets are resuspended by vortexing in 3 mUg 10 mM Tris-HCl, pH 7.4, and the suspension is kept at 25 Degrees C for 15 min. Following centrifugation at 31000 g for 15 min, the pellets are resuspended by gentle Potter Elvehjem homogenization to a volume of 1.53 mUg in 10 mM Tris-HCl pH 7.4.

The assay tubes contain 10, pt of [$^3$H]-DTG (final concentration of 3 nM), 400 μL of the tissue suspension (5.3 mUg in 50 mM Tris-HCl, pH 8.0) to a final assay volume of 0.5 mL. Non-specific binding is defined by addition of a final concentration of 1 μM haloperidol. All tubes are incubated at 25 Degrees C for 120 min before termination of the reaction by rapid filtration over Schleicher and Schuell GF 3362 glass fibre filters [previously soaked in a solution of 0.5 percent polyethylenimine for at least 1 h]. Filters are washed three times with 5 mL volumes of cold Tris-HCl buffer (10 mM, pH 8.0). Following addition of scintillation cocktail samples are allowed to equilibrate overnight. The amount of bound radioactivity is determined by liquid scintillation spectrometry using a Wallac Winspectral 1414 liquid scintillation counter. Protein concentrations are determined by the method of Lowry et al. (1951).

Pharmacological Studies

Brain membrane preparation and binding assays for the 61-receptor were performed as described (DeHaven-Hudkins, D. L., L. C. Fleissner, and F. Y. Ford-Rice, 1992, Characterization of the binding of [$^3$H](+)pentazocine to a recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was re-suspended in fresh Tris-HCl buffer (50 mM, pH 7.4) and stored on ice until use.

The radioligand used was [$^3$H]-(+)-pentazocine at 5.0 nM and the final volume was 200 μl. The incubation was initiated with the addition of 100 μl of membrane at a final tissue concentration of approximately 5 mg tissue net weight/mL and the incubation time was 150 m. at 37° C. After incubation, the membranes were collected onto pre-treated glass fiber filterplate (MultiScreen-FC, Millipore), with polyethylenimine 0.1%. The filters were washed two times with 200 μl of washing buffer (50 mM Tris Cl, pH=7.4) and then 25 μl of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

Some of the results obtained are shown in table (I).

TABLE (I)

| Example | Ki (σ1) [nM] |
|---------|--------------|
| 2 | 4.8 |
| 3 | 31.1 |
| 4 | 48.5 |
| 5 | 45.8 |
| 6 | 97.4 |
| 7 | 61.1 |
| 9 | 10.3 |
| 10 | 34.8 |
| 12 | 8.7 |

TABLE (I)-continued

| Example | Ki (σ1) [nM] |
|---------|--------------|
| 13 | 11.7 |
| 14 | 10.8 |
| 15 | 23.3 |
| 17 | 51.7 |
| 18 | 35.4 |
| 19 | 214.4 |
| 20 | 34.6 |
| 23 | 194.0 |
| 29 | 68.7 |
| 30 | 62.5 |
| 31 | 56.4 |
| 32 | 36.3 |
| 33 | 13.4 |
| 34 | 132.6 |
| 37 | 32.7 |
| 39 | 61.5 |
| 40 | 45.5 |
| 41 | 105.1 |
| 43 | 70.2 |
| 46 | 57.7 |
| 47 | 31.4 |
| 48 | 143.8 |
| 49 | 99.4 |
| 50 | 273.4 |
| 51 | 274.9 |
| 57 | 71.5 |
| 63 | 42.5 |
| 64 | 110.7 |
| 65 | 216.2 |
| 68 | 240.6 |

The invention claimed is:

1. A 1,2,3-triazole-4-amine derivative of general formula (I):

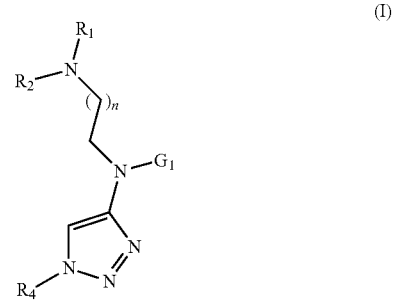

wherein:

$G_1$ is selected from the group consisting of a hydrogen atom; a linear or branched, saturated or unsaturated, substituted or unsubstituted aliphatic radical; a substituted or unsubstituted aryl group which is optionally condensed to other, substituted or unsubstituted, mono- or polycyclic ring systems; a —(C═O)—$R_5$ group; a —(SO)$_2$—$R_6$ group; and a —C═Z—NH—$R_8$ group;

$R_1$ and $R_2$, which may be identical or different, are selected from the group consisting of a hydrogen atom; and a linear or branched, saturated or unsaturated, substituted or unsubstituted aliphatic radical;

or $R_1$ and $R_2$ together with the bridging nitrogen atom to which they are attached form an at least mono-cyclic, substituted or unsubstituted, at least one heteroatom containing heterocyclyl group which is optionally condensed with a substituted or unsubstituted mono- or polycyclic ring system;

$R_4$ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; and a branched or unbranched, saturated, substituted or unsubstituted alkyl-aryl group in which the aryl group may be substituted or unsubstituted and/or condensed with a mono- or polycyclic ring system;

$R_5$ is selected from the group consisting of a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; and a branched or unbranched, saturated, substituted or unsubstituted alkyl-heterocyclyl group in which the heterocyclyl group may be substituted or unsubstituted and/or condensed with a mono- or polycyclic ring system;

$R_6$ is selected from the group consisting of a linear or branched, saturated or unsaturated, substituted or unsubstituted aliphatic radical; a substituted or unsubstituted aryl group which is optionally condensed to other, substituted or unsubstituted, mono- or polycyclic ring systems; and a branched or unbranched, saturated or unsaturated, substituted or unsubstituted alkyl-cycloalkyl group in which the cycloalkyl group may be substituted or unsubstituted and/or condensed with a mono- or polycyclic ring system;

Z is S or O;

$R_8$ is a linear or branched, saturated or unsaturated, substituted or unsubstituted aliphatic radical;

n is 1, 2, 3, or 4;

optionally as a stereoisomer, including enantiomers and diastereomers, a racemate or as of a mixture of at least two stereoisomers, including enantiomers and/or diastereomers, in any mixing ratio, or a salt thereof, or a solvate thereof.

2. The 1,2,3-triazole-4-amine derivative according to claim 1, wherein $G_1$ is selected from the group consisting of a hydrogen atom; a linear or branched, saturated or unsaturated, substituted or unsubstituted $C_{1-4}$ alkyl radical; an substituted or unsubstituted, at least six membered aryl group; a —(C=O)—$R_5$ group; a —(SO)$_2$—$R_6$ group; and a —C=Z—NH—$R_8$ group.

3. The 1,2,3-triazole-4-amine derivative according to claim 2, wherein $R_5$ is selected from the group consisting of a linear or branched, saturated or unsaturated, substituted or unsubstituted $C_{1-4}$ alkyl radical; an substituted or unsubstituted, $C_3$-$C_6$ cycloalkyl group; and an substituted or unsubstituted, at least six-membered aryl group;

$R_6$ is selected from the group consisting of a linear or branched, saturated or unsaturated, substituted or unsubstituted $C_{1-4}$ alkyl radical; and an substituted or unsubstituted, at least six-membered aryl group;

Z is S or O; and $R_8$ is a linear or branched, saturated or unsaturated, substituted or unsubstituted $C_{1-4}$ alkyl radical.

4. The 1,2,3-triazole-4-amine derivative according to claim 3, wherein $G_1$ is selected from the group consisting of a hydrogen atom; a substituted or unsubstituted ethyl group; a substituted or unsubstituted propyl group; a substituted or unsubstituted benzyl group; a —(C=O)—$R_5$ group; a —(SO)$_2$—$R_6$ group; and a —C=Z—NH—$R_8$ group; and $R_5$ is selected from the group consisting of a substituted or unsubstituted methyl group; a substituted or unsubstituted tert-butyl group; a substituted or unsubstituted cyclopropane group; a substituted or unsubstituted cyclohexyl group; and a substituted or unsubstituted phenyl group, wherein the substituents are selected from halogen;

$R_6$ is selected from the group consisting of a substituted or unsubstituted methyl group; and a substituted or unsubstituted phenyl group, wherein the substituents are selected from halogen;

Z is S or O; and $R_8$ is a linear or branched, saturated or unsaturated, substituted or unsubstituted $C_{1-4}$ alkyl radical.

5. The 1,2,3-triazole-4-amine derivative according to claim 1 wherein $R_1$ and $R_2$, which may be identical or different, are selected from the group consisting of a hydrogen atom; and a linear or branched, saturated or unsaturated, substituted or unsubstituted $C_{1-4}$ alkyl radical;

or $R_1$ and $R_2$ together with the bridging nitrogen atom to which they are attached form a mono-cyclic, substituted or unsubstituted, at least one heteroatom containing $C_5$-$C_7$ heterocyclyl group, which is optionally condensed with an substituted or unsubstituted mono- or polycyclic ring system; wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, and $C_3$-$C_6$ cycloalkyl.

6. The 1,2,3-triazole-4-amine derivative according to claim 5, wherein $R_1$ and $R_2$, which may be identical or different, are selected from the group consisting of a hydrogen atom; and a linear or branched, substituted or unsubstituted ethyl group;

or $R_1$ and $R_2$ together with the bridging nitrogen atom to which they are attached form a substituted or unsubstituted heterocyclyl group, selected from the group consisting of a pyrrolidine group, a piperazine group, a piperidine group, a morpholine group, an azepane group or an oxazepane group; the heterocyclyl group being unsubstituted or substituted, wherein the substituents are selected from the group consisting of a methyl group, an ethanone group, a fluoro group, a chloro group and a cyclohexyl group.

7. The 1,2,3-triazole-4-amine derivative according to claim 1, wherein
$R_4$ is selected from the group consisting of an substituted or unsubstituted $C_6$-$C_{10}$ cycloalkyl group, which is optionally condensed to other, substituted or unsubstituted, mono- or polycyclic ring systems; a substituted or unsubstituted at least six membered aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group is at least six membered and may be substituted or unsubstituted and/or condensed with a mono- or polycyclic ring system; and a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted; wherein the substituents are selected from halogen.

8. The 1,2,3-triazole-4-amine derivative according to claim 7, wherein
$R_4$ is selected from the group consisting of a substituted or unsubstituted cyclohexyl group; a substituted or unsubstituted adamantyl group; a substituted or unsubstituted phenyl group; a substituted or unsubstituted benzyl group; and a substituted or unsubstituted naphtalene group, wherein the substituents are selected from fluoro and chloro.

9. The 1,2,3-triazole-4-amine derivative according to claim 1, wherein
n is 1 or 2.

10. The 1,2,3-triazole-4-amine derivative according to claim 1, wherein
$G_1$ is selected from the group consisting of a hydrogen atom; a linear or branched, saturated or unsaturated, substituted or unsubstituted $C_{1-4}$ alkyl radical; a substituted or unsubstituted, at least six membered aryl group; a —(C=O)—$R_5$ group; a —(SO)$_2$—Re group; and a —C=Z—NH—$R_8$ group;
$R_1$ and $R_2$, which may be identical or different, are selected from the group consisting of a hydrogen atom; and a linear or branched, saturated or unsaturated, substituted or unsubstituted $C_{1-4}$ alkyl radical;
or
$R_1$ and $R_2$ together with the bridging nitrogen atom to which they are attached form a mono-cyclic, substituted or unsubstituted, at least one heteroatom containing $C_5$-$C_7$ heterocyclyl group, which is optionally condensed with a substituted or unsubstituted mono- or polycyclic ring system; wherein the heteroatom is selected from the group consisting of N, S, O; the heterocyclyl group and/or mono- or polycyclic ring system being unsubstituted or substituted, wherein the substituents are selected from the group consisting of $C_1$-$C_4$ alkyl, $C_1$-$C_4$ alkoxy, halogen, and $C_3$-$C_6$ cycloalkyl;

$R_4$ is selected from the group consisting of an substituted or unsubstituted $C_6$-$C_{10}$ cycloalkyl group, which is optionally condensed to other, substituted or unsubstituted, mono- or polycyclic ring systems; a substituted or unsubstituted, at least six membered aryl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group is at least six membered and may be substituted or unsubstituted and/or condensed with a mono- or polycyclic ring system; and a branched or unbranched, saturated, substituted or unsubstituted alkyl-aryl group in which the aryl group is at least six membered and/or condensed with a mono- or polycyclic ring system; the heterocyclyl group and/or mono- or polycyclic ring system being unsubstituted or substituted, wherein the substituents are selected from halogen;
$R_5$ is selected from the group consisting of a linear or branched, saturated or unsaturated, substituted or unsubstituted $C_{1-4}$ alkyl radical; a substituted or unsubstituted, $C_3$-$C_6$ cycloalkyl group; and an substituted or unsubstituted, at least six-membered aryl group;
$R_6$ is selected from the group consisting of a linear or branched, saturated or unsaturated, substituted or unsubstituted $C_{1-4}$ alkyl radical; and a substituted or unsubstituted, at least six-membered aryl group;
Z is S or O; and
$R_8$ is a linear or branched, saturated or unsaturated, substituted or unsubstituted $C_{1-4}$ alkyl radical.

11. The 1,2,3-triazole-4-amine derivative according to claim 1, wherein
$G_1$ is selected from the group consisting of a hydrogen atom; an ethyl group; a propyl group; a substituted or unsubstituted benzyl group; a —(C=O)—$R_5$ group; a —(SO)$_2$—$R_6$ group; and a —C=Z—NH—$R_8$ group, wherein the substituents are chloro;
$R_1$ and $R_2$, each represent an ethyl group;
or
$R_1$ and $R_2$ together with the bridging nitrogen atom to which they are attached form a heterocyclyl group selected from the group consisting of a pyrrolidine group, a piperazine group, a piperidine group, a morpholine group, an azepane group, and an oxazepane group; the heterocyclyl group being unsubstituted or substituted, wherein the substituents are selected from the group consisting of a methyl group, an ethanone group, a fluoro, a chloro and a cyclohexyl group;
$R_4$ is selected from the group consisting of a cyclohexyl group; an adamantyl group; a substituted or unsubstituted phenyl group, a substituted or unsubstituted benzyl group, and a naphtalene group; wherein the substituents are selected from fluoro and chloro;
$R_5$ is selected from the group consisting of a methyl group; a tert-butyl group; a cyclopropane group; a cyclohexyl group; and a phenyl group;
$R_6$ is selected from the group consisting of a methyl group; and a substituted phenyl group, wherein the substituent is chloro;
Z is S;
$R_8$ is propyl; and
n is 1 or 2.

12. The 1,2,3-triazole-4-amine derivative according to claim 1, which is selected from the group consisting of:
1-(4-(2-(1-(3,4-dichlorobenzyl)-1H-1,2,3-triazol-4-ylamino)ethyl)piperazin-1-yl)ethanone hydrochloride;

1-(3,4-dichlorophenyl)-N-(2-(piperidin-1-yl)ethyl)-1H-1,2,3-triazol-4-amine hydrochloride;
1-(2,4-dichlorophenyl)-N-(2-(piperidin-1-yl)ethyl)-1H-1,2,3-triazol-4-amine hydrochloride;
1-benzyl-N-(2-(piperidin-1-yl)ethyl)-1H-1,2,3-triazol-4-amine hydrochloride;
1-(3,4-dichlorophenyl)-N-(2-morpholinoethyl)-i H-1,2,3-triazol-4-amine hydrochloride;
1-(1-adamantyl)-N-(2-morpholinoethyl)-1H-1,2,3-triazol-4-amine hydrochloride;
1-(3,4-dichlorobenzyl)-N-(2-morpholinoethyl)-H-1,2,3-triazol-4-amine hydrochloride;
1-benzyl-N-(2-morpholinoethyl)-1H-1,2,3-triazol-4-amine hydrochloride;
1-(3,4-dichlorobenzyl)-N-(2-(piperidin-1-yl)ethyl)-1H-1,2,3-triazol-4-amine hydrochloride;
1-(3,4-dichlorobenzyl)-N-(3-(piperidin-1-yl)propyl)-1H-1,2,3-triazol-4-amine hydrochloride;
1-(3-fluorophenyl)-N-(2-morpholinoethyl)-1H-1,2,3-triazol-4-amine hydrochloride;
N-(2-(azepan-1-yl)ethyl)-1-(3,4-dichlorobenzyl)-1H-1,2,3-triazol-4-amine hydrochloride;
N-(2-(azepan-1-yl)ethyl)-1-(3-fluorophenyl)-1H-1,2,3-triazol-4-amine hydrochloride;
N-(2-(azepan-1-yl)ethyl)-1-(1-adamantyl)-1H-1,2,3-triazol-4-amine hydrochloride;
N-(2-(azepan-1-yl)ethyl)-1-benzyl-1H-1,2,3-triazol-4-amine hydrochloride;
1-benzyl-N-(2-(4-methylpiperazin-1-yl)ethyl)-1H-1,2,3-triazol-4-amine hydrochloride;
1-(4-fluorobenzyl)-N-(2-(piperidin-1-yl)ethyl)-1H-1,2,3-triazol-4-amine hydrochloride;
1-(3-fluorobenzyl)-N-(2-(piperidin-1-yl)ethyl)-1H-1,2,3-triazol-4-amine hydrochloride;
1-benzyl-N-(2-(pyrrolidin-1-yl)ethyl)-1H-1,2,3-triazol-4-amine hydrochloride;
1-(3-fluorophenyl)-N-(2-(pyrrolidin-1-yl)ethyl)-1H-1,2,3-triazol-4-amine hydrochloride;
N1-(1-benzyl-1H-1,2,3-triazol-4-yl)-N2,N2-diethylethane-1,2-diamine hydrochloride;
N-(2-morpholinoethyl)-1-(naphthalen-1-yl)-1H-1,2,3-triazol-4-amine hydrochloride;
1-(3,4-dichlorophenyl)-N-(3-morpholinopropyl)-1H-1,2,3-triazol-4-amine hydrochloride;
1-cyclohexyl-N-(2-morpholinoethyl)-1H-1,2,3-triazol-4-amine hydrochloride;
1-(4-fluorobenzyl)-N-(2-morpholinoethyl)-1H-1,2,3-triazol-4-amine hydrochloride;
1-(3,4-dichlorobenzyl)-N-(3-morpholinopropyl)-1H-1,2,3-triazol-4-amine;
1-(4-fluorobenzyl)-N-(3-morpholinopropyl)-1H-1,2,3-triazol-4-amine;
1-cyclohexyl-N-(3-morpholinopropyl)-1H-1,2,3-triazol-4-amine;
1-cyclohexyl-N-(2-(piperidin-1-yl)ethyl)-1H-1,2,3-triazol-4-amine hydrochloride;
1-cyclohexyl-N-(2-(4-cyclohexylpiperazin-1-yl)ethyl)-1H-1,2,3-triazol-4-amine hydrochloride;
N-(2-(4-cyclohexylpiperazin-1-yl)ethyl)-1-(3-fluorophenyl)-1H-1,2,3-triazol-4-amine hydrochloride;
N-(2-(1,4-oxazepan-4-yl)ethyl)-1-(3-fluorophenyl)-1H-1,2,3-triazol-4-amine hydrochloride;
N-(2-(1,4-oxazepan-4-yl)ethyl)-1-(3,4-dichlorobenzyl)-1H-1,2,3-triazol-4-amine hydrochloride;
N-(2-(4-cyclohexylpiperazin-1-yl)ethyl)-1-(4-fluorobenzyl)-1H-1,2,3-triazol-4-amine;
1-(4-chlorophenyl)-N-(2-morpholinoethyl)-1H-1,2,3-triazol-4-amine hydrochloride;
1-(3,4-difluorobenzyl)-N-(2-morpholinoethyl)-1H-1,2,3-triazol-4-amine hydrochloride;
1-(3,4-difluorobenzyl)-N-(2-(piperidin-1-yl)ethyl)-1H-1,2,3-triazol-4-amine hydrochloride;
1-(2,4-difluorophenyl)-N-(2-morpholinoethyl)-1H-1,2,3-triazol-4-amine hydrochloride;
1-(4-chlorophenyl)-N-(2-(piperidin-1-yl)ethyl)-1H-1,2,3-triazol-4-amine hydrochloride;
1-(3,4-difluorobenzyl)-N-(2-(4,4-difluoropiperidin-1-yl)ethyl)-1H-1,2,3-triazol-4-amine hydrochloride;
N-(2-(4,4-difluoropiperidin-1-yl)ethyl)-1-(4-fluorobenzyl)-1H-1,2,3-triazol-4-amine hydrochloride;
1-(3,4-difluorophenyl)-N-(2-morpholinoethyl)-1H-1,2,3-triazol-4-amine hydrochloride;
1-(3,4-difluorophenyl)-N-(2-(4,4-difluoropiperidin-1-yl)ethyl)-1H-1,2,3-triazol-4-amine hydrochloride;
1-(4-fluorophenyl)-N-(2-morpholinoethyl)-1H-1,2,3-triazol-4-amine hydrochloride;
1-(3-chloro-4-fluorophenyl)-N-(2-morpholinoethyl)-1H-1,2,3-triazol-4-amine hydrochloride;
1-(3-fluorophenyl)-N-(2-(piperidin-1-yl)ethyl)-1H-1,2,3-triazol-4-amine hydrochloride;
1-(3,4-difluorophenyl)-N-(2-(piperidin-1-yl)ethyl)-1H-1,2,3-triazol-4-amine hydrochloride;
1-(4-fluorophenyl)-N-(2-(piperidin-1-yl)ethyl)-1H-1,2,3-triazol-4-amine hydrochloride;
N-(2-((2RS*,6SR*)-2,6-dimethylpiperidin-1-yl)ethyl)-1-(4-fluorobenzyl)-1H-1,2,3-triazol-4-amine;
1-(2,4-difluorophenyl)-N-(2-(piperidin-1-yl)ethyl)-1H-1,2,3-triazol-4-amine;
1-(4-(2-(1-(3,4-dichlorophenyl)-1H-1,2,3-triazol-4-ylamino)ethyl)piperazin-1-yl)ethanone hydrochloride;
N-(1-(1-adamantyl)-1H-1,2,3-triazol-4-yl)-N-(2-morpholinoethyl)cyclopropanecarboxamide hydrochloride;
N-(1-(1-adamantyl)-1H-1,2,3-triazol-4-yl)-N-(2-morpholinoethyl)cyclohexanecarboxamide hydrochloride;
N-(1-(1-adamantyl)-1H-1,2,3-triazol-4-yl)-N-(2-morpholinoethyl)benzamide hydrochloride;
N-(1-(1-adamantyl)-1H-1,2,3-triazol-4-yl)-N-(2-morpholinoethyl)pivalamide hydrochloride;
N-(1-(3,4-dichlorobenzyl)-1H-1,2,3-triazol-4-yl)-N-(2-morpholinoethyl)acetamide hydrochloride;
N-(1-(1-adamantyl)-1H-1,2,3-triazol-4-yl)-N-(2-morpholinoethyl)acetamide hydrochloride;
N-(1-(3,4-dichlorophenyl)-1H-1,2,3-triazol-4-yl)-N-(2-morpholinoethyl)acetamide hydrochloride;
N-(1-(3,4-dichlorophenyl)-1H-1,2,3-triazol-4-yl)-N-(2-morpholinoethyl)methane sulfonamide hydrochloride;
4-chloro-N-(1-(3,4-dichlorophenyl)-1H-1,2,3-triazol-4-yl)-N-(2-morpholinoethyl) benzenesulfonamide hydrochloride;
1-(3,4-dichlorophenyl)-N-(2-morpholinoethyl)-N-propyl-1H-1,2,3-triazol-4-amine hydrochloride;
1-benzyl-N-(2-chlorobenzyl)-N-(2-(piperidin-1-yl)ethyl)-1H-1,2,3-triazol-4-amine;
1-(3,4-dichlorobenzyl)-N-(3-(piperidin-1-yl)propyl)-N-propyl-1H-1,2,3-triazol-4-amine;
1-(1-adamantyl)-N-ethyl-N-(2-morpholinoethyl)-1H-1,2,3-triazol-4-amine hydrochloride;
1-(3,4-dichlorophenyl)-N-ethyl-N-(2-morpholinoethyl)-1H-1,2,3-triazol-4-amine hydrochloride;
1-(1-adamantyl)-N-(2-morpholinoethyl)-N-propyl-1H-1,2,3-triazol-4-amine hydrochloride;

N-(4-chlorobenzyl)-1-(1-adamantyl)-N-(2-morpholino-ethyl)-1H-1,2,3-triazol-4-amine hydrochloride; and 1-(1-(3,4-dichlorophenyl)-1H-1,2,3-triazol-4-yl)-1-(2-morpholinoethyl)-3-propylthiourea hydrochloride or a pharmaceutically acceptable salt, prodrug or solvate thereof.

13. A process for the production of a 1,2,3-triazole-4-amine derivative of general formula (I):

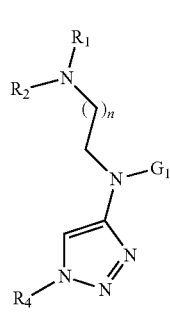

(I)

wherein

G₁ is selected from the group consisting of a hydrogen atom; a linear or branched, saturated or unsaturated, substituted or unsubstituted aliphatic radical; a substituted or unsubstituted aryl group which is optionally condensed to other, substituted or unsubstituted, mono- or polycyclic ring systems; a —(C=O)—R₅ group; a —(SO)₂—R₆ group; and a —C=Z—NH—R₈ group;

R₁ and R₂, which may be identical or different, are selected from the group consisting of a hydrogen atom; and a linear or branched, saturated or unsaturated, substituted or unsubstituted aliphatic radical; or R₁ and R₂ together with the bridging nitrogen atom to which they are attached form an at least mono-cyclic, substituted or unsubstituted, at least one heteroatom containing heterocyclyl group which is optionally condensed with a substituted or unsubstituted mono- or polycyclic ring system; and R₄ is selected from the group consisting of a hydrogen atom; a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; and a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system;

R₅ is selected from the group consisting of a linear or branched, saturated or unsaturated, substituted or unsubstituted aliphatic radical; a substituted or unsubstituted cycloalkyl group which is optionally condensed to other, substituted or unsubstituted, mono- or polycyclic ring systems; a substituted or unsubstituted aryl group which is optionally condensed to other, substituted or unsubstituted, mono- or polycyclic ring systems; a substituted or unsubstituted heterocyclyl group which is optionally condensed to other, substituted or unsubstituted, mono- or polycyclic ring systems; a branched or unbranched, saturated or unsaturated, substituted or unsubstituted alkyl-cycloalkyl group in which the cycloalkyl group may be substituted or unsubstituted and/or condensed with a mono- or polycyclic ring system; a branched or unbranched, saturated, substituted or unsubstituted alkyl-aryl group in which the aryl group may be substituted or unsubstituted and/or condensed with a mono- or polycyclic ring system; and a branched or unbranched, saturated, substituted or unsubstituted alkyl-heterocyclyl group in which the heterocyclyl group may be substituted or unsubstituted and/or condensed with a mono- or polycyclic ring system;

R₆ is selected from the group consisting of a linear or branched, saturated or unsaturated, substituted or unsubstituted aliphatic radical; a substituted or unsubstituted aryl group which is optionally condensed to other, substituted or unsubstituted, mono- or polycyclic ring systems; and a branched or unbranched, saturated or unsaturated, substituted or unsubstituted alkyl-cycloalkyl group in which the cycloalkyl group may be substituted or unsubstituted and/or condensed with a mono- or polycyclic ring system;

Z is S or O;

R₈ is a linear or branched, saturated or unsaturated, substituted or unsubstituted aliphatic radical; and n is 1, 2, 3, or 4, wherein a compound of formula (III):

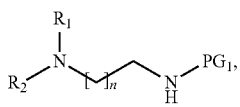

(III)

wherein PG₁ represents a nitrogen-protecting group, is reacted with a compound of formula (VI):

(VI)

wherein X represents chloro, bromo or iodo and PG₂ represents a nitrogen-protecting group, under copper catalyzed alkynylation conditions, to yield a compound of formula (VII):

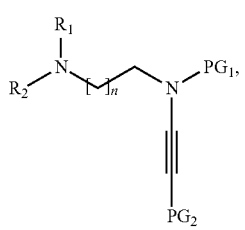

(VII)

which compound of formula (VII) is subjected to deprotection conditions to selectively remove the PG₂ protecting group, wherein the deprotection reaction is optionally carried out in an aprotic solvent, including THF, with an appropriate reagent, including TBAF, followed by a cycloaddition reaction with an organic azide of formula (VIII):

(VIII)

wherein the cycloaddition reaction is optionally carried out in situ by the addition of catalytic amounts of a Cu(I) salt, and an excess of a base, including a tertiary amine including DIPEA, to yield a compound of formula (IX):

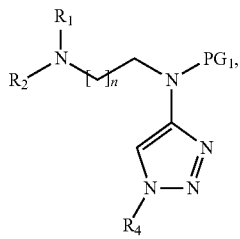

(IX)

which compound of formula (IX) is subjected to N-deprotection conditions to yield a compound of formula (Ia):

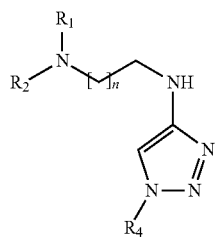

(Ia)

(i.e., the compound of formula (I) wherein $G_1$ represents a hydrogen atom), which compound of formula (Ia) may be further reacted with an acylating agent of formula (X):

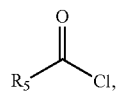

(X)

to yield a compound of formula (I) wherein $G_1$ represents a —(C=O)—$R_5$ group;

or the compound of formula (Ia) may be further reacted with a compound of formula (XI):

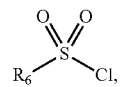

(XI)

to yield a compound of formula (I), wherein $G_1$ represents an —(SO)$_2$—$R_6$ group;

or the compound of formula (Ia) may be further reacted with an aldehyde under reductive amination conditions to yield a compound of formula (I), wherein $G_1$ represents a linear or branched, saturated or unsaturated, substituted or unsubstituted aliphatic radical; a substituted or unsubstituted aryl group which is optionally condensed to other, substituted or unsubstituted, mono- or polycyclic ring systems;

or the compound of formula (Ia) may be further reacted with a compound of formula (XIII):

$R_8NCZ$, (XIII)

to yield a compound of formula (I), wherein $G_1$ represents a —C=Z—NH—$R_8$ group.

14. A pharmaceutical composition comprising one or more 1,2,3-triazole-4-amine derivatives of general formula (I) according to claim 1, or solvates or prodrugs thereof, and at least one pharmaceutically acceptable excipient.

* * * * *

UNITED STATES PATENT AND TRADEMARK OFFICE
CERTIFICATE OF CORRECTION

PATENT NO. : 9,611,229 B2  
APPLICATION NO. : 14/759280  
DATED : April 4, 2017  
INVENTOR(S) : Antoni Torrens-Jover et al.

Page 1 of 1

It is certified that error appears in the above-identified patent and that said Letters Patent is hereby corrected as shown below:

On the Title Page

Column 2, References Cited: "Jagerovc" should be --Jagerovic--.

In the Claims

Column 93, Line 49 Claim 11: "$R_e$" should be --$R_6$--.

Column 95, Line 7 Claim 12: "i H" should be --1H--.

Signed and Sealed this  
Seventeenth Day of April, 2018

Andrei Iancu  
*Director of the United States Patent and Trademark Office*